(12) United States Patent
Zhou et al.

(10) Patent No.: US 9,512,155 B2
(45) Date of Patent: Dec. 6, 2016

(54) CHIRAL PHOSPHINES FOR PALLADIUM-CATALYZED ASYMMETRIC α-ARYLATION OF ESTER ENOLATES TO PRODUCE TERTIARY STEREOCENTERS IN HIGH ENANTIOSELECTIVITY

(75) Inventors: Steve Jianrong Zhou, Singapore (SG); Zhiyan Huang, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/239,541

(22) PCT Filed: Aug. 17, 2012

(86) PCT No.: PCT/SG2012/000292
§ 371 (c)(1),
(2), (4) Date: Apr. 15, 2014

(87) PCT Pub. No.: WO2013/028132
PCT Pub. Date: Feb. 28, 2013

(65) Prior Publication Data
US 2015/0166586 A1    Jun. 18, 2015

Related U.S. Application Data

(60) Provisional application No. 61/525,388, filed on Aug. 19, 2011.

(51) Int. Cl.
| | |
|---|---|
| *C07C 69/95* | (2006.01) |
| *C07F 9/50* | (2006.01) |
| *C07D 215/14* | (2006.01) |
| *C07D 333/38* | (2006.01) |
| *C07F 9/53* | (2006.01) |
| *C07C 253/30* | (2006.01) |
| *C07C 67/00* | (2006.01) |
| *C07C 51/09* | (2006.01) |
| *C07C 51/00* | (2006.01) |
| *C07C 69/612* | (2006.01) |
| *C07C 69/616* | (2006.01) |

(52) U.S. Cl.
CPC ............. *C07F 9/5022* (2013.01); *C07C 51/00* (2013.01); *C07C 51/09* (2013.01); *C07C 67/00* (2013.01); *C07C 69/612* (2013.01); *C07C 69/616* (2013.01); *C07C 253/30* (2013.01); *C07D 215/14* (2013.01); *C07D 333/38* (2013.01); *C07F 9/509* (2013.01); *C07F 9/5325* (2013.01); *C07B 2200/07* (2013.01); *C07C 2101/14* (2013.01)

(58) Field of Classification Search
CPC ..... C07C 67/00; C07C 253/30; C07C 51/09; C07C 69/616; C07C 255/57; C07C 59/64; C07C 69/608; C07C 69/734; C07C 69/738; C07C 69/76; C07C 2101/14; C07C 51/00; C07C 69/612; C07B 2200/07; C07D 215/14; C07D 333/38; C07F 9/5022; C07F 9/509; C07F 9/5325

See application file for complete search history.

(56) References Cited

PUBLICATIONS

Xiaoxiang Liu(Palladium-Catalyzed Arylation of Trimethylsilyl Enolates of Esters and Imides. High Functional Group Tolerance and Stereoselective Synthesis of r-Aryl Carboxylic Acid, . AM. Chem. Soc. 2004, 126, 5182-5191).*

Liu et al. (Palladium-Catalyzed Arylation of Trimethylsilyl Enolates of Esters and Imides. High Functional Group Tolerance and Stereoselective Synthesis of r-Aryl Carboxylic Acid, . AM. Chem. Soc. 2004, 126, 5182-5191).*

International Search Report for PCT/SG2012/000292 mailed on Dec. 3, 2012.

Written Opinion of the International Searching Authority mailed on Dec. 3, 2012.

International Preliminary Report on Patentability Chapter 1 mailed on Dec. 3, 2012.

Hong, J. et al, "Application of Bulky and Electron-Rich MOP-Type Phosphine Ligands in Palladium-Catalyzed α-Arylation of 1,3-Dicarbonyl Compounds." Chinese Journal of Organic Chemistry, 2008, 28(8), 1410-1415.

Hamada, T. et al, "An Improved Catalyst for the Asymmetric Arylation of Ketone Enolates." Journal of the American Chemical Society, 2002, 124(7), 1261-1268.

Lee, S. et al, "Improved Catalysts for the Palladium-Catalyzed Synthesis of Oxindoles by Amide α-Arylation. Rate Acceleration, Use of Aryl Chloride Substrates, and a New Carbene Ligand for Asymmetric Transformations." Journal of Organic Chemistry. 2001, 66(10), 3402-3415.

Higham, L. et al, "P-chirogenic Phosphines. MOP/diPAMP hybrids, Their Oxide Crystal Structures, Reduction Studies and Alternative Syntheses." Journal of Organometallic Chemistry, 2005, 690(1), 211-219.

(Continued)

*Primary Examiner* — Yevegeny Valenrod
*Assistant Examiner* — Blaine G Doletski
(74) *Attorney, Agent, or Firm* — Ladas & Parry, LLP

(57) ABSTRACT

The disclosure provides new and improved methods for the Pd-catalyzed asymmetric α-arylation of ester compounds, which produce the corresponding α-aryl moiety in high enantioselectivity (generally >90% ee). The present methods utilize a palladium catalyst supported by new (R)—H$_8$-BINOL-derived monophosphine ligands. The method is applicable to a wide variety of aryl triflate substrates having variations in both electronic and steric properties. These aryl triflate substrates react with various α-alkyl (Z)- and/or (E)-0-trimethylsilyl ketene acetals in the presence of a Pd catalyst, (R)—H$_8$-BINOL-derived monophosphine ligand, and a mild activator, for example, LiOAC, to provide the asymmetric α-arylation of ester compounds in high ee.

9 Claims, No Drawings

(56) References Cited

PUBLICATIONS

Bayardon, J. et al, "Chiral Fluorous Phosphorus Ligands Based on the Binaphthyl Skeleton: Synthesis and Applications in Asymmetric Catalysis." Tetrahedron: Asymmetry, 2003, 14(15), 2215-2224.

Kerrigan, N. et al, "Studies in the Preparation of Novel P-chirogenic Binaphthyl Monophosphanes (MOPs)." Tetrahedron Letters, 2003, 44(46), 8461-8465. Abstract; compound 3, p. 8461; compounds 12a and 12b; Scheme 3; Table 1.

Martin, R. et at, "A General Method for the Direct α-Arylation of Aldehydes with Aryl Bromides and Chlorides." Angewandte Chemie, International Edition, 2007, 46(38), 7236-7239.

Dotta, P. et al. "3,5-Dialkyl Effect on Enantioselectivity in Pd Chemistry: Applications Involving both Bidentate and Monodentate Auxiliaries." Organometallics, 2004, 23(10), 2295-2304.

Shi, M. et al, "Chiral Bifunctional Organocatalysts in Asymmetric Aza-Morita-Baylis-Hillman Reactions of Ethyl (Arylimino)acetates with Methyl Vinyl Ketone and Ethyl Vinyl Ketone." Journal of Organic Chemistry, 2007, 72(25), 9779-9781.

Lei, Z-Y et al, "Bifunctional Chiral Phosphine-containing Lewis Base Catalyzed Asymmetric Morita-Baylis-Hillman Reaction of Aldehydes with activated Alkenes." Tetrahedron: Asymmetry, 2008, 19(17) 2058-2062.

Huang, Z. et al, "An Enantioselective, Intermolecular α-Arylation of Ester Enolates to Form Tertiary Stereocenters." Journal of the American Chemical Society, 2011, 133 (40), 15882-15885. Whole document.

Ma, F. et al, "Palladium-Catalyzed Coupling Reaction of Amino Acids (Esters) With Aryl Bromides and Chlorides." Tetrahedron, 2011, 67(48), 9405-9410. Abstract: compounds L1 and L2, Table 1.

\* cited by examiner

CHIRAL PHOSPHINES FOR PALLADIUM-CATALYZED ASYMMETRIC α-ARYLATION OF ESTER ENOLATES TO PRODUCE TERTIARY STEREOCENTERS IN HIGH ENANTIOSELECTIVITY

CROSS-REFERENCE TO RELATED APPLICATIONS

This application is the U.S. National Stage of PCT/SG2012/00292 filed on Aug. 17, 2012 which claims the benefit of priority under 35 U.S.C. §119(e) to U.S. Provisional Patent Application No. 61/525,388, titled "CHIRAL PHOSPHINES FOR PALLADIUM-CATALYZED ASYMMETRIC ALPHA-ARYLATION OF ESTER ENOLATES TO PRODUCE TERTIARY STEROCENTERS IN HIGH ENANTIONSELECTIVITY," filed on Aug. 19, 2011, the entire disclosures of which are hereby incorporated by reference in their entireties for all purposes.

FIELD OF THE INVENTION

The present invention is in the field of synthetic organic chemistry, and in particular in the field of transition-metal catalyzed, asymmetric α-arylation of carbonyl compounds to produce α-aryl carbonyl compounds having tertiary centers with high enantioselectivity.

BACKGROUND OF THE DISCLOSURE

Chiral α-arylalkanoic acids and derivatives are core structures in many drug molecules. For example, the profen family of nonsteroidal anti-inflammatory drugs are all α-arylpropionic acids, including blockbusters such as Ibuprofen, Naproxen, and Ketoprofen. The enantiomers of these compounds are known to display substantially different pharmacological profiles and Naproxen is sold in its optically pure (S)-form. To achieve convergent and efficient synthesis, aryl groups are best introduced with concomitant establishment of chirality. However, asymmetric α-arylation of esters using either aryl-metal reagents or aryl electrophiles has met only with limited success. One example was recently reported by Fu et al., in which arylsilanes were used as equivalent of "aryl-metal" reagents. These compounds underwent Ni-catalyzed coupling with racemic α-bromoester to give products containing tertiary centers in high enantiomeric excess (ee). A more straightforward disconnection involves C—C bond formation between aryl halides/sulfonates and enolate anions. Successful examples of this kind with excellent ee are surprisingly scarce. In the work by Buchwald and coworkers, aryl chlorides were used to couple with enolates generated in situ from γ-butyrolactone and a strong base. Although a high level of ee was achieved, the method was limited to the formation of quaternary stereocenters. In fact, all of metal-catalyzed, enantioselective arylations of carbonyl compounds (including ketones, aldehydes, oxindoles and α-methylacetoacetates) suffered from the same limitation. The challenge in producing alpha asymmetric tertiary centers lies in the increased acidity of the α-hydrogen of the monoarylation product than the starting material and therefore, these products can be readily deprotonated under basic conditions. The deprotonation can eventually lead to racemization and in some cases, double arylation. Thus, there remains a need in the art for new and improved methods and reagents for the efficient α-arylation of ester anions to produce tertiary centers with high ee.

SUMMARY OF THE INVENTION

The present invention addresses these needs by providing new and improved methods for the Pd-catalyzed asymmetric α-arylation of ester compounds, which produce the corresponding α-aryl moiety in high enantioselectivity (generally >90% ee). The present methods utilize a palladium catalyst supported by new (R)—$H_8$-BINOL-derived monophosphine ligands. The method is applicable to various aryl triflate substrates, with variations in both electronic and steric properties. The reaction partners are various α-alkyl (Z)- and/or (E)-O-trimethylsilyl ketene acetals derived from bulky esters such as t-butyl esters and the like.

It has been discovered that several important experimental parameters ensure the realization of the highly asymmetric process. First, the (E) geometry of the ketene acetals is important for the stereochemical outcome. Next, weakly basic activators including LiOAc and the like, may be used to activate the silyl ketene acetals and to produce the synthetic equivalent of ester anions under almost neutral conditions. In this way, racemization and double arylation of the enantioenriched monoarylation producted may be avoided. Finally, new chiral monophosphines derived from (R)—$H_8$-BINOL have been discovered, which are selective in inducing the excellent enantioselection during the coupling process.

Many α-arylcarbonxylic acids belong to the profen family of nonsteroidal anti-inflammatory drugs, which are blockbusters on the market. The methods described herein provide a general and efficient way to access these chiral compounds in high enantioselectivity. In addition, the ee of the chiral α-arylcarboxylic acids can be further improved by simple crystallization.

Thus, in one embodiment the disclosure provides methods for asymmetrically synthesizing an α-aryl compound of Formula I:

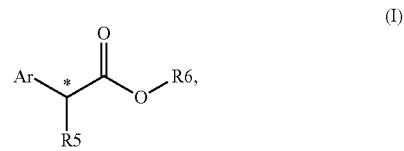

or a pharmaceutically acceptable salt thereof, the method comprising the step of reacting a compound of Formula II with a compound of Formula III in the presence of a palladium catalyst, an activator, a compound of Formula IV, and optionally a solvent, to produce the asymmetric α-aryl compound of Formula I:

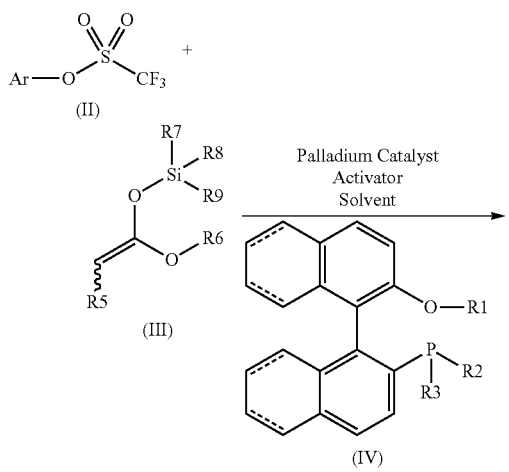

-continued

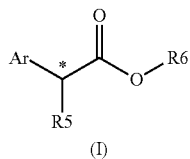

wherein:
* is an asymmetric carbon atom;
the compound of Formula III is the (E)- or (Z)—OSiR$^7$R$^8$R$^9$ isomer;
the palladium catalyst is selected from PdMe$_2$(TMEDA), Pd(dba)$_2$, and Pd(OAc)$_2$;
the solvent is an aromatic solvent
Ar is a substituted or unsubstituted aryl or substituted or unsubstituted heteroaryl group, which is optionally independently substituted with 1, 2 or 3 R$^4$ groups;
⫶ is a single or double bond, wherein either all of the ⫶ are single bonds or all of the ⫶ are double bonds;
R$^1$ is independently selected from hydrogen, alkyl, aryl, and arylalkyl;
R$^2$ and R$^3$ are each independently selected from alkyl, cycloalkyl, aryl and arylalkyl;
each R$^4$ is independently selected from hydrogen, amino, halogen, hydroxyl, nitro, cyano, alkyl, alkenyl, alkynyl, perfluoroalkyl, cycloalkyl, alkoxy, heterocycloalkyl, aryl, arylalkyl, heteroaryl, heteroarylalkyl, (CH$_2$)$_j$OR$^{11}$, (CH$_2$)$_j$C(O)R$^{11}$, (CH$_2$)$_j$C(O)OR$^{11}$, (CH$_2$)$_j$OC(O)R$^{11}$, (CH$_2$)$_j$NR$^{12}$R$^{13}$, (CH$_2$)$_j$C(O)NR$^{12}$R$^{13}$, (CH$_2$)$_j$OC(O)NR$^{12}$R$^{13}$, (CH$_2$)$_j$NR$^{14}$C(O)R$^{11}$, (CH$_2$)$_j$NR$^{14}$C(O)OR$^{11}$, (CH$_2$)$_j$NR$^{14}$C(O)NR$^{12}$R$^{13}$, (CH$_2$)$_j$S(O)$_m$R$^{11}$, and (CH$_2$)$_j$S(O)$_m$NR$^{12}$R$^{13}$, wherein each j is independently an integer selected from 0 to 6, and each m is independently an integer selected from 0 to 2;
R$^5$ is independently selected from substituted or unsubstituted alkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, which is optionally independently substituted with 1, 2 or 3 R$^{10}$ groups;
R$^6$ is independently selected from hydrogen, substituted or unsubstituted alkyl, substituted or unsubstituted cycloalkyl, substituted or unsubstituted aryl, and substituted or unsubstituted arylalkyl, which is optionally independently substituted with 1, 2 or 3 R$^{10}$ groups;
R$^7$, R$^8$ and R$^9$ are each independently selected from alkyl, aryl and arylalkyl;
each R$^{10}$ is independently selected from hydrogen, amino, halogen, hydroxyl, nitro, cyano, alkyl, alkenyl, alkynyl, perfluoroalkyl, cycloalkyl, alkoxy, heterocycloalkyl, aryl, arylalkyl, heteroaryl, heteroarylalkyl, (CH$_2$)$_j$OR$^{11}$, (CH$_2$)$_j$C(O)R$^{11}$, (CH$_2$)$_j$C(O)OR$^{11}$, (CH$_2$)$_j$OC(O)R$^{11}$, (CH$_2$)$_j$NR$^{12}$R$^{13}$, (CH$_2$)$_j$C(O)NR$^{12}$R$^{13}$, (CH$_2$)$_j$OC(O)NR$^{12}$R$^{13}$, (CH$_2$)$_j$NR$^{14}$C(O)R$^{11}$, (CH$_2$)$_j$NR$^{14}$C(O)OR$^{11}$, (CH$_2$)$_j$NR$^{14}$C(O)NR$^{12}$R$^{13}$, (CH$_2$)$_j$S(O)$_m$R$^{11}$, and (CH$_2$)$_j$S(O)$_m$NR$^{12}$R$^{13}$, wherein each j is independently an integer selected from 0 to 6, and each m is independently an integer selected from 0 to 2;
R$^{11}$ is independently selected from hydrogen, alkyl, alkenyl, alkynyl, perfluoroalkyl, cycloalkyl, heterocycloalkyl, aryl, arylalkyl, heteroaryl, and heteroarylalkyl; and
R$^{12}$, R$^{13}$, R$^{14}$ are each independently selected from hydrogen, alkyl, alkenyl, alkynyl, perfluoroalkyl, cycloalkyl, heterocycloalkyl, aryl, arylalkyl, heteroaryl, and heteroarylalkyl, or R$^{14}$ is as described above, and R$^{12}$ and R$^{13}$ are joined together with the nitrogen atom to which they are attached, to form a substituted or unsubstituted 3- to 7-membered hetercycloalkyl or substituted or unsubstituted 5-membered heteroaryl, wherein the 3- to 7-membered hetercycloalkyl is selected from aziridine, azetidine, pyrrolidinyl, pyrazolidinyl, imidazolidinyl, piperidinyl, piperazinyl, morpholinyl, thiomorpholinyl, and azepanyl; and the 5-membered heteroaryl is selected from pyrrolyl, pyrazolyl, imidazolyl, pyridinyl, pyrazinyl, pyrimidinyl, indolyl, purinyl, benzimidazolyl, quinolinyl, and isoquinolinyl.

In another embodiment the disclosure provides a compound of Formula I:

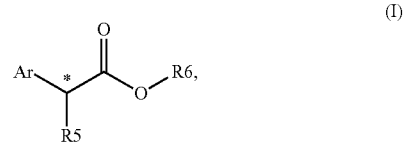

or a pharmaceutically acceptable salt thereof, prepared by the disclosed methods.

In another embodiment the disclosure provides a compound having Formula IV:

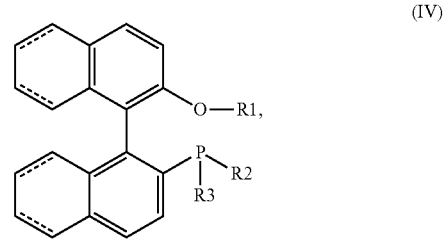

or a pharmaceutically acceptable salt thereof, wherein:
⫶ is a single or double bond, wherein either all of the ⫶ are single bonds or all of the ⫶ are double bonds;
R$^1$ is independently selected from hydrogen, alkyl, aryl, and arylalkyl; and
R$^2$ and R$^3$ are each independently selected from alkyl, cycloalkyl, aryl and arylalkyl.

In another embodiment the disclosure provides methods for preparing a compound of Formula IV:

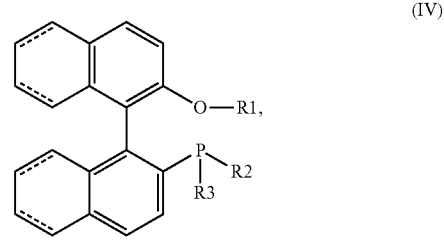

or a pharmaceutically acceptable salt thereof, the method comprising the steps of:
a) reacting a compound of Formula V with a compound R—X in the presence of a base to provide a compound of Formula VI

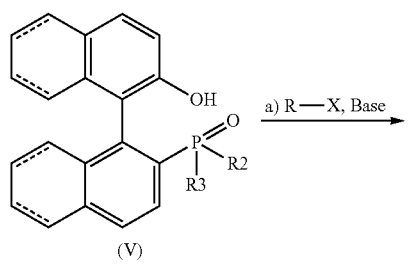

(V)

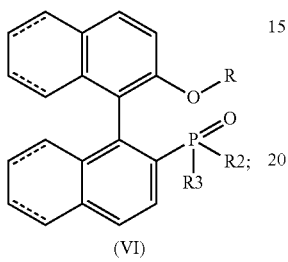

(VI)

and b) reducing the compound of Formula VI with a reducing agent to provide the compound of Formula IV:

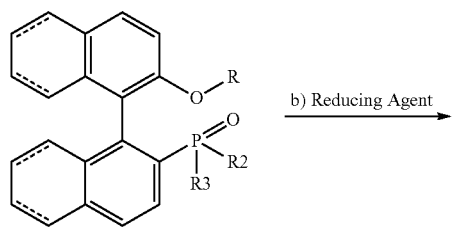

(IV)

wherein:

R is selected from alkyl, cycloalkyl, aryl, and arylalkyl;

⟋ is a single or double bond, wherein either all of the

⟋ are single bonds or all of the ⟋ are double bonds;

$R^1$ is independently selected from hydrogen, alkyl, aryl, and arylalkyl; and $R^2$ and $R^3$ are each independently selected from alkyl, cycloalkyl, aryl and arylalkyl.

In another embodiment the disclosure provides a compound of Formula IV:

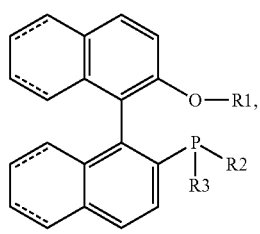

(IV)

or a pharmaceutically acceptable salt thereof, prepared by the disclosed methods.

DETAILED DESCRIPTION OF THE EMBODIMENTS

Definitions

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, definitions and abbreviations further apply:

The term "alkyl," by itself or as part of another substituent, means, unless otherwise stated, a straight (i.e. Unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, pentadienyl), ethynyl, 1- and 3-propynyl, 3-butynyl, and the higher homologs and isomers. Alkyl groups which are limited to hydrocarbon groups are termed "homoalkyl."

Specific values listed herein for groups, substituents, and ranges, are for illustration; they do not exclude other defined values or other values within defined ranges for the groups and substituents. For example, "alkyl" can be methyl, ethyl, propyl, isopropyl, butyl isobutyl, sec-butyl, pentyl, 3-pentyl, or hexyl; cycloalkyl can be cyclopropyl, cyclobutyl, cyclopentyl, or cyclohexyl; "—O($C_1$-$C_6$)alkyl (alkoxy)" can be methoxy, ethoxy, propoxy, isopropoxy, butoxy, iso-butoxy, sec-butoxy, pentoxy, 3-pentoxy, or hexyloxy.

The term "alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2CH$=$CCH_2$—, —$CH_2CH_2CH(CH_2CH_2CH_3)CH_2$—. Typically, an alkyl (or alkylene) group will have from 1 to 24 carbon atoms, which includes those groups having 10 or fewer carbon atoms. A "lower alkyl" or "lower alkylene" is a shorter chain alkyl or alkylene group, generally having eight or fewer carbon atoms.

The terms "alkyl, alkoxy, alkenyl, alkynyl," etc. Denote both straight and branched groups; but reference to an individual group such as "propyl" embraces the straight chain group, a branched chain isomer such as "isopropyl" being specifically referred to.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— includes both —C(O)OR'— and —R'OC(O)—. As described above, heteroalkyl groups, as used herein, include those groups that are attached to the remainder of the molecule through a heteroatom, such as —C(O)R', —C(O)NR', —NR'R', —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, re, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

More specifically, the term "alkyl" refers to a branched or unbranched saturated hydrocarbon group of 1 to 6 carbon atoms, such as methyl, ethyl, n-propyl, isopropyl, n-butyl, isobutyl, t-butyl, pentyl, and the like. Alkyl groups herein contain 1 to 6 carbon atoms, such as, for example, methyl, ethyl, and the like. As used herein the term "alkyl" also includes the term "cycloalkyl," which refers to a cyclic alkyl group of three to eight, including three, five or six, carbon atoms. The term "cycloalkylene" as used herein refers to a divalent cyclic alkylene group, typically a 3-, 5-, 6-, or 8-membered ring.

The term "alkoxy" as used herein refers to an alkyl group bound through a single, terminal ether linkage, i.e., an "alkoxy" group may be defined as —OR, where R is alkyl as defined herein. A "lower alkoxy" group refers to an alkoxy group containing 1 to 6, carbon atoms.

The term "aryl" means, unless otherwise stated, a polyunsaturated, aromatic, hydrocarbon substituent which can be a single ring or multiple rings (from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pynolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover aryls substituted with one or more halogens.

The term "aryl" as used herein refers to an aromatic carbocyclic ring, typically 6- or 10-membered, wherein at least one ring is aromatic. For example, "aryl" denotes a phenyl group or an ortho-fused bicyclic carbocyclic group having about nine to ten ring atoms in which at least one ring is aromatic.

"Heteroaryl" encompasses a group attached via a ring carbon of a monocyclic aromatic ring containing five or six ring atoms consisting of carbon and one to four heteroatoms each independently may be non-peroxide oxygen, sulfur, and N(X), where X is absent or is H, O, ($C_1$-$C_4$)alkyl, phenyl or benzyl, as well as a group of an ortho-fused bicyclic-heterocycle of about eight to ten ring atoms derived therefrom, particularly a benz-derivative or one derived by fusing a propylene, trimethylene, or tetramethylene digroup thereto.

Where a heteroalkyl, heterocycloalkyl, or heteroaryl includes a specific number of members (e.g. "3 to 7 membered"), the term. "member" referrers to a carbon or heteroatom.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. The term "halo" also refers to fluoro, chloro, bromo, or iodo.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —C(O)NR'R", —OC(O)NR'R", —NR" C(O)R', —NR' —C(O)NR"R'", —NR" C(O)OR', —NR—C(NR' R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R'" and R"" groups when more than one of these groups is. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH—, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR' R", —OC(O)NR'R", —NR" C(O)R', —NR'—C(O)NR"R'", —NR" C(O)OR', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro ($C_1$-$C_4$)alkyl, in a number ranging from zero to the total number of open valences on aromatic ring system; and where R', R", R'" and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R' group, for example, each of the R groups is independently selected as are each R', R", R'" and R"" groups when more than one of these groups is.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$), —B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the disclosure may exist as salts. The disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, mono-hydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methane-sulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The neutral forms of the compounds are regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure and are intended to be within the scope of the disclosure.

Certain compounds of the disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-somers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the compounds are within the scope of the disclosure.

Unless otherwise stated, structures depicted herein are also meant to include compounds which differ in the presence of one or more isotopically enriched atoms. For example, compounds having the structures except for the replacement of a hydrogen by a deuterium or tritium, or the replacement of a carbon by $^{13}$C- or $^{14}$C-enriched carbon are within the scope of this disclosure.

The compounds of the disclosure may also contain unnatural proportions of atomic isotopes at one or more of atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the disclosure, whether radioactive or not, are encompassed within the scope of the disclosure.

Throughout the present disclosure the term "about" a certain value means that a range of value ±25%, and preferably a range of value ±10%, and more preferably a range of value ±5%, is contemplated. Thus, for example, about 20 mol % of a certain reagent includes the reagent being present between 15% and 25%, preferably between 18% and 22%, and more preferably between 19% and 73.5%.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

It will be appreciated by those skilled in the art that compounds of the disclosure having a chiral center may exist in and be isolated in optically active and racemic forms. Some compounds may exhibit polymorphism. It is to be understood that the disclosure encompasses any racemic, optically active, polymorphic, or stereoisomeric form, or mixtures thereof, of a compound of the disclosure, which possesses the useful properties described herein. Also, if the named compound comprises a chiral center, the scope of the disclosure also includes compositions comprising the racemic mixture of the two enantiomers, as well as compositions comprising each enantiomer individually, substantially free of the other enantiomer. Thus, for example, contemplated herein is a composition comprising the S enantiomer substantially free of the R enantiomer, or a composition comprising the R enantiomer substantially free of the S enantiomer.

By "substantially free" it is meant that the composition comprises less than 10%, or less than 8%, or less than 5%, or less than 3%, or less than 1% of the minor enantiomer. If the named compound comprises more than one chiral center, the scope of the disclosure also includes compositions comprising a mixture of the various diastereomers, as well as compositions comprising each diastereomer substantially free of the other diastereomers.

It is well known in the art how to prepare optically active forms (for example, by resolution of the racemic form by recrystallization techniques, by synthesis from optically active starting materials, by chiral synthesis, or by chromatographic separation using a chiral stationary phase) and how to determine the anti cancer activity using the standard tests described herein, or using other similar tests which are well known in the art.

As used herein, "substantially pure" means an object species is the predominant species (i.e., on a molar basis it is more abundant than any other individual species in the composition), and a substantially purified fraction is a composition wherein the object species comprises at least about 50 percent (on a molar basis) of all macromolecular species. Generally, a substantially pure composition will comprise more than about 80 percent of all macromolecular species in the composition, for example, more than about 85%, 90%, 95%, and 99%. The object species may be also purified to essential homogeneity (contaminant species cannot be detected in the composition by conventional detection methods), wherein the composition consists essentially of a single species.

The BINOL-derived monophosphine ligands may be derived from 1,1'-bi-2-naphthol (BINOL). BINOL is often used as a ligand for the transition metal catalyzed asymmetric synthesis. BINOL has axial chirality and the two enantiomers, i.e. (R)-BINOL and (S)-BINOL, which can be readily separated and are stable towards racemization. Axial chirality is a special case of chirality in which a molecule does not possess a stereogenic center but instead, has an axis of chirality. That is, an axis about which a set of substituents is held in a spatial arrangement that is not superposable on its mirror image. Axial chirality is most commonly observed in atropisomeric biaryl compounds wherein the rotation about the aryl-aryl bond is restricted such as in BINOL. The enantiomers of axially chiral compounds are usually given the stereochemical labels $R_a$ and $S_a$. These designations are based on the same Cahn-Ingold-Prelog priority rules used for tetrahedral stereocenters. For convenience, the stereochemical labels R and S will be used herein for (R)- and (S)-BINOL.

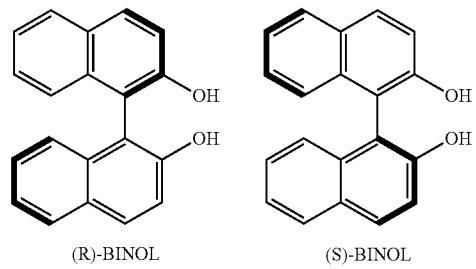

(R)-BINOL          (S)-BINOL

The corresponding (R)—$H_8$-BINOL and (S)—$H_8$-BINOL are shown below:

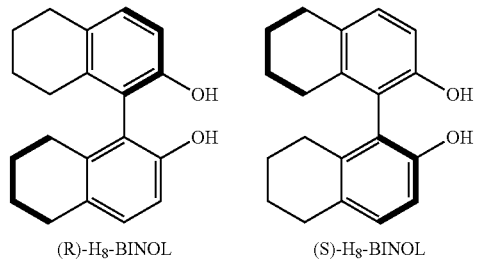

(R)-$H_8$-BINOL          (S)-$H_8$-BINOL

In one embodiment the disclosure provides methods for asymmetrically synthesizing an α-aryl compound of Formula I:

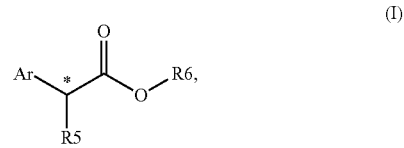

(I)

or a pharmaceutically acceptable salt thereof, the method comprising the step of reacting a compound of Formula II with a compound of Formula III in the presence of a palladium catalyst, an activator, a compound of Formula IV, and optionally a solvent, to produce the asymmetric α-aryl compound of Formula I:

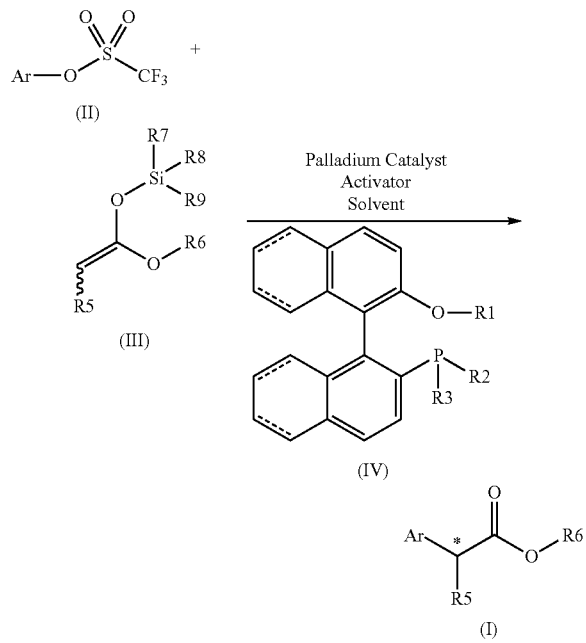

wherein:
* is an asymmetric carbon atom;
the compound of Formula III is the (E)- or (Z)—OSiR$^7$R$^8$R$^9$ isomer;
the palladium catalyst is selected from PdMe$_2$(TMEDA), Pd(dba)$_2$, and Pd(OAc)$_2$;
the solvent is an organic solvent
Ar is a substituted or unsubstituted aryl or substituted or unsubstituted heteroaryl group, which is optionally independently substituted with 1, 2 or 3 R$^4$ groups;

⫽ is a single or double bond, wherein either all of the ⫽ are single bonds or all of the ⫽ are double bonds;
R$^1$ is independently selected from hydrogen, alkyl, aryl, and arylalkyl;
R$^2$ and R$^3$ are each independently selected from alkyl, cycloalkyl, aryl and arylalkyl;
each R$^4$ is independently selected from hydrogen, amino, halogen, hydroxyl, nitro, cyano, alkyl, alkenyl, alkynyl, perfluoroalkyl, cycloalkyl, alkoxy, heterocycloalkyl, aryl, arylalkyl, heteroaryl, heteroarylalkyl, (CH$_2$)$_j$OR$^{11}$, (CH$_2$)$_j$C(O)R$^{11}$, (CH$_2$)$_j$C(O)OR$^{11}$, (CH$_2$)$_j$OC(O)R$^{11}$, (CH$_2$)$_{jNR}$$^{12}$R$^{13}$, (CH$_2$)$_j$C(O)NR$^{12}$R$^{13}$, (CH$_2$)$_j$OC(O)NR$^{12}$R$^{13}$, (CH$_2$)NR$^{14}$C(O)R$^{11}$, (CH$_2$)NR$^{14}$C(O)OR$^{11}$, (CH$_2$)NR$^{14}$C(O)NR$^{12}$R$^{13}$, (CH$_2$)$_j$S(O)$_m$R$^{11}$, and (CH$_2$)$_j$S(O)$_m$NR$^{12}$R$^{13}$, wherein each j is independently an integer selected from 0 to 6, and each m is independently an integer selected from 0 to 2;
R$^5$ is independently selected from substituted or unsubstituted alkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, which is optionally independently substituted with 1, 2 or 3 R$^{10}$ groups;

R$^6$ is independently selected from hydrogen, substituted or unsubstituted alkyl, substituted or unsubstituted cycloalkyl, substituted or unsubstituted aryl, and substituted or unsubstituted arylalkyl, which is optionally independently substituted with 1, 2 or 3 R$^{10}$ groups;
R$^7$, R$^8$ and R$^9$ are each independently selected from alkyl, aryl and arylalkyl;
each R$^{10}$ is independently selected from hydrogen, amino, halogen, hydroxyl, nitro, cyano, alkyl, alkenyl, alkynyl, perfluoroalkyl, cycloalkyl, alkoxy, heterocycloalkyl, aryl, arylalkyl, heteroaryl, heteroarylalkyl, (CH$_2$)$_j$OR$^{11}$, (CH$_2$)$_j$C(O)R$^{11}$, (CH$_2$)$_j$C(O)OR$^{11}$, (CH$_2$)$_j$OC(O)R$^{11}$, (CH$_2$)$_j$NR$^{12}$R$^{13}$, (CH$_2$)$_j$C(O)NR$^{12}$R$^{13}$, (CH$_2$)$_j$OC(O)NR$^{12}$R$^{13}$, (CH$_2$)NR$^{14}$C(O)R$^{11}$, (CH$_2$)NR$^{14}$C(O)OR$^{11}$, (CH$_2$)NR$^{14}$C(O)NR$^{12}$R$^{13}$, (CH$_2$)$_j$S(O)$_m$R$^{11}$, and (CH$_2$)$_j$S(O)$_m$NR$^{12}$R$^{13}$, wherein each j is independently an integer selected from 0 to 6, and each m is independently an integer selected from 0 to 2;
R$^{11}$ is independently selected from hydrogen, alkyl, alkenyl, alkynyl, perfluoroalkyl, cycloalkyl, heterocycloalkyl, aryl, arylalkyl, heteroaryl, and heteroarylalkyl; and
R$^{12}$, R$^{13}$, R$^{14}$ are each independently selected from hydrogen, alkyl, alkenyl, alkynyl, perfluoroalkyl, cycloalkyl, heterocycloalkyl, aryl, arylalkyl, heteroaryl, and heteroarylalkyl, or R$^{14}$ is as described above, and R$^{12}$ and R$^{13}$ are joined together with the nitrogen atom to which they are attached, to form a substituted or unsubstituted 3- to 7-membered hetercycloalkyl or substituted or unsubstituted 5-membered heteroaryl, wherein the 3- to 7-membered hetercycloalkyl is selected from aziridine, azetidine, pyrrolidinyl, pyrazolidinyl, imidazolidinyl, piperidinyl, piperazinyl, morpholinyl, thiomorpholinyl, and azepanyl; and the 5-membered heteroaryl is selected from pyrrolyl, pyrazolyl, imidazolyl, pyridinyl, pyrazinyl, pyrimidinyl, indolyl, purinyl, benzimidazolyl, quinolinyl, and isoquinolinyl.

In embodiments of this method, the organic solvent is selected from benzene, chlorobenzene, fluorobenzene, toluene, trifluorobenzene, dichloromethane, dichloroethane, tetrahydrofuran, and combinations thereof.

In other embodiments of this method the activator is selected from the group consisting of LiOC(O)CH3, LiOC(O)CF3, LiOS(O)2CH3, LiOC(O)C(CH3)3, LiF, NaOC(O)CH3, NaOC(O)CF3, Na2CO3, KOC(O)CH3, CsF, Cs2CO3, CsOC(O)CH3, ZnF2, Zn(OC(O)CH3)2, CuF2, and combinations thereof.

In one aspect the disclosure provides methods for asymmetrically synthesizing an α-aryl compound of Formula I, wherein
* is an R or S asymmetric carbon atom, wherein the asymmetric α-aryl compound of Formula I is at least about 50% to about 60% enantiomeric excess;
the compound of Formula III is the (E)-OSiR$^7$R$^8$R$^9$ isomer;
the palladium catalyst is PdMe$_2$(TMEDA);
the activator is selected from LiOC(O)CH$_3$;
the solvent is selected from benzene, chlorobenzene, fluorobenzene, toluene, trifluorobenzene, dichloromethane, dichloroethane, and tetrahydrofuran;
Ar is a substituted or unsubstituted phenyl, substituted or unsubstituted biphenyl, substituted or unsubstituted naphthalenyl, substituted or unsubstituted benzyl, substituted or unsubstituted CH$_2$(1-naphthalenyl), substituted or unsubstituted CH$_2$(2-naphthalenyl), substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted pyridinyl, substituted or unsubstituted pyrazinyl, substituted or unsubstituted pyrimidinyl, substituted or unsubstituted indolyl, substituted or unsubstituted purinyl, substituted or unsubstituted benzimidazolyl, substituted or unsubstituted benzo[b]thiophenyl, substituted or unsubstituted quinolinyl, and substituted or unsubstituted isoquinolinyl;

$R^1$ is independently selected from hydrogen, $(C_1-C_6)$alkyl, phenyl, biphenyl, naphthalenyl, benzyl, $CH_2$(1-naphthalenyl) and $CH_2$(2-naphthalenyl);

$R^2$ and $R^3$ are each independently selected from $(C_1-C_6)$alkyl, $(C_3-C_6)$cycloalkyl, phenyl, biphenyl, benzyl, and naphthalenyl;

$R^5$ is independently selected from substituted or unsubstituted $(C_{1-12})$alkyl, substituted or unsubstituted phenyl, substituted or unsubstituted biphenyl, substituted or unsubstituted naphthalenyl, substituted or unsubstituted benzyl, substituted or unsubstituted $CH_2$(1-naphthalenyl), substituted or unsubstituted $CH_2$(2-naphthalenyl), substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted pyridinyl, substituted or unsubstituted pyrazinyl, substituted or unsubstituted pyrimidinyl, substituted or unsubstituted indolyl, substituted or unsubstituted purinyl, substituted or unsubstituted benzimidazolyl, substituted or unsubstituted benzo[b]thiophenyl, substituted or unsubstituted quinolinyl, substituted or unsubstituted isoquinolinyl, substituted or unsubstituted aziridine, substituted or unsubstituted oxiranyl, substituted or unsubstituted thiiranyl, substituted or unsubstituted azetidinyl, substituted or unsubstituted oxetanyl, substituted or unsubstituted thietanyl, substituted or unsubstituted pyrrolidinyl, substituted or unsubstituted pyrazolidinyl, substituted or unsubstituted imidazolidinyl, substituted or unsubstituted oxolanyl, substituted or unsubstituted thiolanyl, substituted or unsubstituted piperidinyl, substituted or unsubstituted oxanyl, substituted or unsubstituted thianyl, substituted or unsubstituted piperazinyl, substituted or unsubstituted morpholinyl, substituted or unsubstituted thiomorpholinyl, substituted or unsubstituted azepanyl, substituted or unsubstituted oxepanyl, and substituted or unsubstituted thiepinyl;

$R^6$ is independently selected from hydrogen, substituted or unsubstituted $(C_1-C_6)$alkyl, substituted or unsubstituted $(C_3-C_8)$cycloalkyl, phenyl, substituted or unsubstituted biphenyl, substituted or unsubstituted naphthalenyl, substituted or unsubstituted benzyl, substituted or unsubstituted $CH_2$(1-naphthalenyl), substituted or unsubstituted $CH_2$(2-naphthalenyl); and $R^7$, $R^8$ and $R^9$ are each independently selected from $(C_1-C_6)$alkyl and phenyl.

In another aspect the disclosure provides methods for asymmetrically synthesizing an α-aryl compound of Formula I, wherein:

* is an R or S asymmetric carbon atom, wherein the asymmetric α-aryl compound of Formula I is at least about 60% to about 70% enantiomeric excess;

Ar is selected from substituted or unsubstituted phenyl, substituted or unsubstituted naphthalenyl, substituted or unsubstituted benzyl, substituted or unsubstituted $CH_2$(1-naphthalenyl), substituted or unsubstituted $CH_2$(2-naphthalenyl), substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted pyridinyl, substituted or unsubstituted pyrazinyl, substituted or unsubstituted pyrimidinyl, substituted or unsubstituted indolyl, substituted or unsubstituted benzimidazolyl, substituted or unsubstituted benzo[b]thiophenyl, substituted or unsubstituted quinolinyl, and substituted or unsubstituted isoquinolinyl;

$R^1$ is independently selected from hydrogen, methyl, ethyl, n-propyl, isopropyl, n-butyl, sec-butyl, tert-butyl, phenyl, benzyl, $CH_2$(1-naphthalenyl), and $CH_2$(2-naphthalenyl);

$R^2$ and $R^3$ are each independently selected from $(C_1-C_6)$alkyl and $(C_3-C_6)$cycloalkyl;

$R^5$ is independently selected from substituted or unsubstituted $(C_1-C_{12})$alkyl, substituted or unsubstituted phenyl, substituted or unsubstituted naphthalenyl, substituted or unsubstituted benzyl, substituted or unsubstituted $CH_2$(1-naphthalenyl), and substituted or unsubstituted $CH_2$(2-naphthalenyl);

$R^6$ is independently selected from hydrogen, $(C_1-C_6)$alkyl, $(C_3-C_8)$cycloalkyl, phenyl, naphthalenyl, benzyl, $CH_2$(1-naphthalenyl), and $CH_2$(2-naphthalenyl); and $R^7$, $R^8$ and $R^9$ are each independently selected from $(C_1-C_6)$alkyl.

In another aspect the disclosure provides methods for asymmetrically synthesizing an α-aryl compound of Formula I, wherein:

* is an R or S asymmetric carbon atom, wherein the asymmetric α-aryl compound of Formula I is at least about 70% to about 80% enantiomeric excess; and the compound of Formula IV has Formula IVa or IVb:

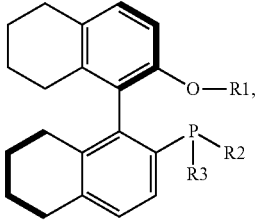

(IVa)

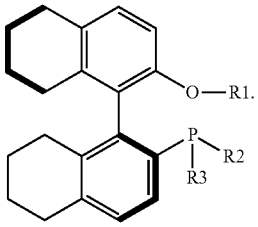

(IVb)

In another aspect the disclosure provides methods for asymmetrically synthesizing an α-aryl compound of Formula I, wherein:

* is an R or S asymmetric carbon atom, wherein the asymmetric α-aryl compound of Formula I is at least about 80% to about 90% enantiomeric excess; and the compound of Formula IV has Formula IVc or IVd:

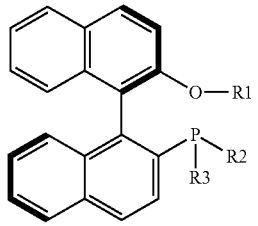

(IVc)

-continued

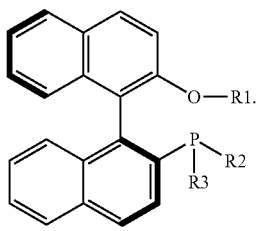
(IVd)

In another aspect the disclosure provides methods for asymmetrically synthesizing an α-aryl compound of Formula I, further comprising heating the compound of Formula II with the compound of Formula III in the presence of the palladium catalyst, the activator, the compound of Formula IV, and the solvent to produce the asymmetric α-aryl compound of Formula I.

In another aspect the disclosure provides methods for asymmetrically synthesizing an α-aryl compound of Formula I, wherein the compound of Formula I, or pharmaceutically acceptable salt thereof, is (S)-Naproxen or the tert-butyl ester thereof:

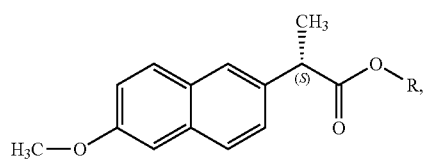

wherein R is H or $C(CH_3)_3$.

In another aspect the disclosure provides a compound of Formula I:

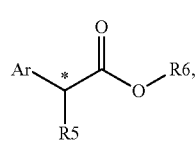
(I)

or a pharmaceutically acceptable salt thereof, prepared by the disclosed methods.

In another aspect the disclosure provides a compound having Formula IV:

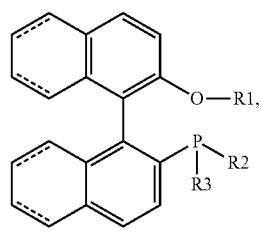
(IV)

or a pharmaceutically acceptable salt thereof, wherein:

⤳ is a single or double bond, wherein either all of the ⤳ are single bonds or all of the ⤳ are double bonds;

$R^1$ is independently selected from hydrogen, alkyl, aryl, and arylalkyl; and $R^2$ and $R^3$ are each independently selected from alkyl, cycloalkyl, aryl and arylalkyl.

In another aspect the disclosure provides a compound having Formula IV, wherein:

$R^1$ is independently selected from hydrogen, $(C_1-C_6)$alkyl, phenyl, biphenyl, naphthalenyl, benzyl, $CH_2$(1-naphthalenyl) and $CH_2$(2-naphthalenyl); and $R^2$ and $R^3$ are each independently selected from $(C_1-C_6)$alkyl, $(C_3-C_6)$cycloalkyl, phenyl, biphenyl, benzyl, and naphthalenyl.

In another aspect the disclosure provides a compound having Formula IV, wherein:

$R^1$ is independently selected from hydrogen, methyl, ethyl, n-propyl, isopropyl, n-butyl, sec-butyl, tert-butyl, phenyl, benzyl, $CH_2$(1-naphthalenyl), and $CH_2$(2-naphthalenyl); and $R^2$ and $R^3$ are each independently selected from $(C_1-C_6)$alkyl and $(C_3-C_6)$cycloalkyl.

In another aspect the disclosure provides a compound having Formula IV, wherein the compound of Formula IV has Formula IVa or IVb:

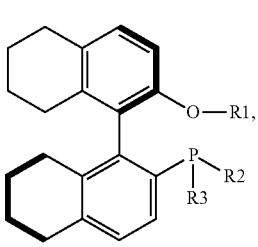
(IVa)

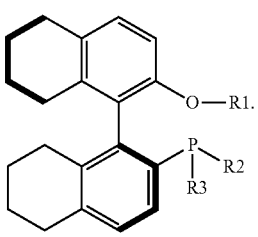
(IVb)

In another aspect the disclosure provides a compound having Formula IV, wherein the compound of Formula IV has Formula IVc or IVd:

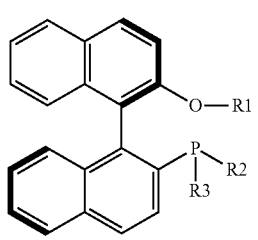
(IVc)

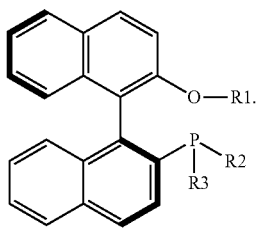

(IVd)

In another aspect the disclosure provides methods for preparing a compound of Formula IV:

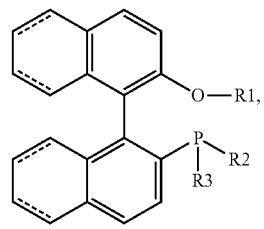

(IV)

or a pharmaceutically acceptable salt thereof, the method comprising the steps of:
a) reacting a compound of Formula V with a compound R—X in the presence of a base to provide a compound of Formula VI

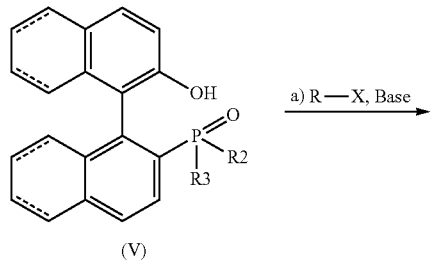

(V)

and
b) reducing the compound of Formula VI with a reducing agent to provide the compound of Formula IV:

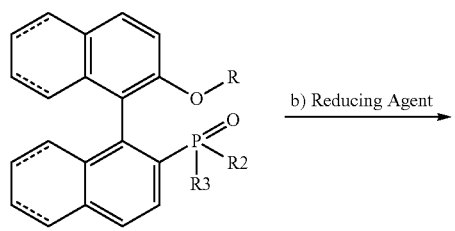

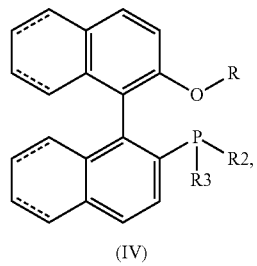

(IV)

wherein:

R is selected from alkyl, cycloalkyl, aryl, and arylalkyl;

⫶⫶ is a single or double bond, wherein either all of the

⫶⫶ are single bonds or all of the ⫶⫶ are double bonds;

$R^1$ is independently selected from hydrogen, alkyl, aryl, and arylalkyl; and $R^2$ and $R^3$ are each independently selected from alkyl, cycloalkyl, aryl and arylalkyl.

In another aspect the disclosure provides methods for preparing a compound of Formula IV, wherein the base is selected from NaH, KH, NaOH, KOH, $Na_2CO_3$, $K_2CO_3$, $Cs_2CO_3$, $KOC(CH_3)_3$, $NH_4OH$, $NH_2(CH_3)$, $NH(CH_3)_2$, $N(CH_3)_3$, $((CH_3)_2CH)_2N(C_2H_5)$, and $C_5H_5N$;

the reducing agent is selected from $HSiCl_3$, $NaBH_4$, and $KBH_4$;

R is selected from methyl, ethyl, n-propyl, isopropyl, n-butyl, sec-butyl, tert-butyl, phenyl, benzyl, $CH_2$(1-naphthalenyl), and $CH_2$(2-naphthalenyl);

$R^1$ is independently selected from hydrogen, $(C_1-C_6)$alkyl, phenyl, biphenyl, naphthalenyl, benzyl, $CH_2$(1-naphthalenyl) and $CH_2$(2-naphthalenyl); and $R^2$ and $R^3$ are each independently selected from $(C_1-C_6)$ alkyl, $(C_3-C_6)$cycloalkyl, phenyl, biphenyl, benzyl, and naphthalenyl.

In another aspect the disclosure provides methods for preparing a compound of Formula IV, wherein:

$R^1$ is independently selected from hydrogen, methyl, ethyl, n-propyl, isopropyl, n-butyl, sec-butyl, tert-butyl, phenyl, benzyl, $CH_2$(1-naphthalenyl), and $CH_2$(2-naphthalenyl); and $R^2$ and $R^3$ are each independently selected from $(C_1-C_6)$ alkyl and $(C_3-C_6)$cycloalkyl.

In another aspect the disclosure provides methods for preparing a compound of Formula IV, wherein the compound of Formula IV has Formula IVa or IVb:

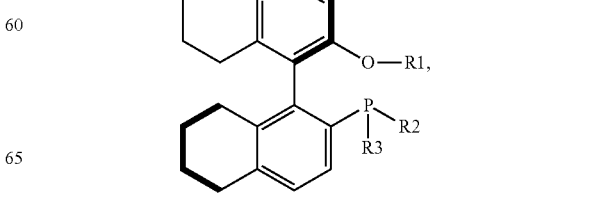

(IVa)

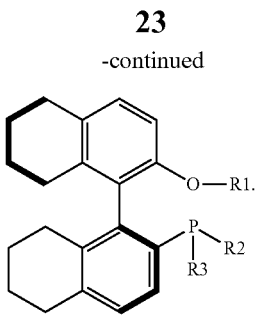
(IVb)

In another aspect the disclosure provides methods for preparing a compound of Formula IV, wherein the compound of Formula IV has Formula IVc or IVd:

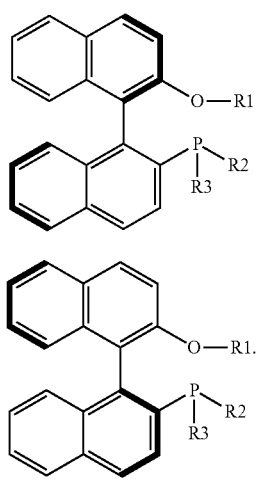
(IVc)

(IVd)

In another aspect the disclosure provides a compound of Formula N:

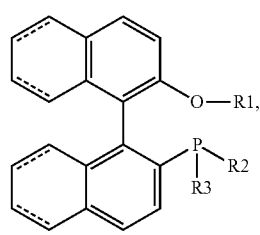
(IV)

or a pharmaceutically acceptable salt thereof, prepared by the methods disclosed herein.

In another aspect the disclosure provides a compound of Formula IV, wherein the compound of Formula IV has Formula Iva, IVb, IVc or IVd:

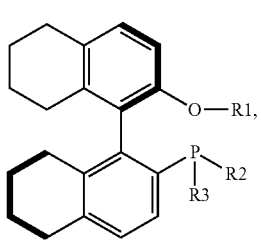
(IVa)

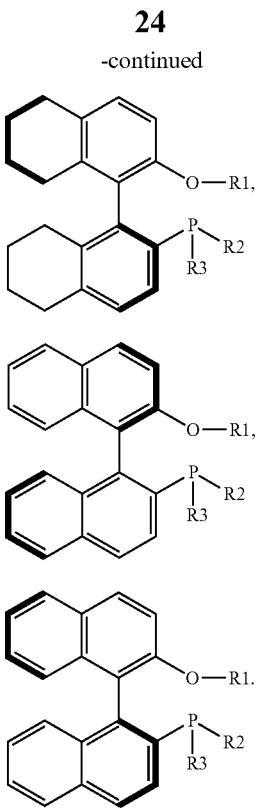
(IVb)

(IVc)

(IVd)

The present invention provides new efficient methods for the α-arylation of ester anions to produce tertiary centers with high ee. Silyl ketene acetals in combination with activators have been studied as equivalent of ester anions in diastereoselective arylations. It has been surprisingly found that if the activators are not basic enough to deprotonate the α-arylesters, asymmetric arylation to form tertiary centers is possible with catalyst control of stereochemistry.

As shown in Scheme I, the model arylation of 1-naphthyl triflate (Naph-OTf) with the PdMe$_2$(TMEDA) catalyst and suitable phosphine ligand of Formula I, along with the use of the activator LiOAc allowed for the efficient coupling of the O-trimethylsilyl ketene acetal derived from tert-butyl propionate.

SCHEME I

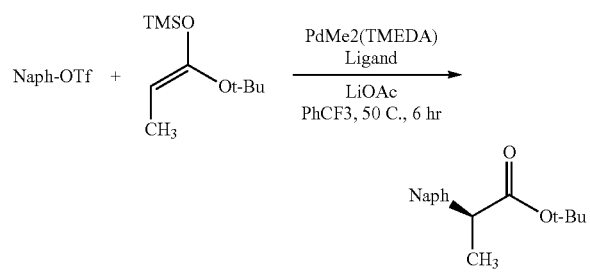

In the presence of a palladium catalyst, for example, from about 1% to about 5% PdMe$_2$(TMEDA), or for example, from about 2% PdMe$_2$(TMEDA), which is supported by a phosphine ligand of Formula I, for example, from about 1% to about 5% ligand L6, or for example, from about 2.4% ligand L6, an activator, for example, from about 1 eq. to about 5 eq. of LiOAc, or for example, from about 2 eq. of LiOAc, and a solvent, for example, PhCF$_3$, α-arylation in about 90% ee may be realized. This reaction was devoid of racemization and double arylation products, while the ee of the monoarylation product remained constant during the course of the reaction.

Among some common palladium complexes, PdMe$_2$(TMEDA) turned out to be optimal in the model reaction. When it was replaced by Pd(dba)$_2$, the coupling became slower, probably due to competitive binding of dba to the active catalyst LPd(0). However, inclusion of about 0.2 equiv of ZnF$_2$ as co-activator, can bring back the activity of the catalyst and afforded the coupling product in 99% yield and 92% ee after 24 h at 50° C.

Besides, the activator LiOAc, other suitable activators include but are not limited to NaOAc, KOAc, CsOAc, CsF, ZnF$_2$, and the like, and combinations thereof.

From an extensive screening of chiral ligands, a series of (R)—H$_8$-BINOL-derived monophosphines emerged to be most promising (Table I).

TABLE I

Effect of Chiral Phosphine Ligands (same conditions as in Scheme I):

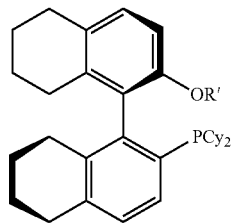

L1 R' = H
L2 Me
L3 i-Pr
L4 Bn
L5 CH$_2$(1-Naph)
L6 CH$_2$(2-Naph)

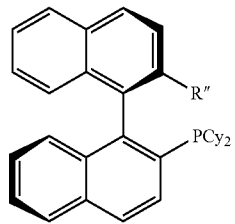

L7 R" = OBn
L8 OCH$_2$(2-Naph)
L9 NMe$_2$ (R)-KenPhos

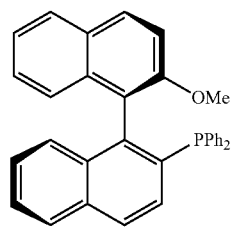

L10 (R)-MOP

| Entry | Ligand | Yield (%) | EE (%) |
|---|---|---|---|
| 1 | L1 | 55 | 68 |
| 2 | L2 | 63 | 81 |
| 3 | L3 | 37 | 72 |
| 4 | L4 | 71 | 86 |
| 5 | L5 | 40 | 85 |
| 6 | L6 | 99 | 90 |
| 7 | L7 | 76 | 67 |
| 8 | L8 | 46 | 70 |
| 9 | L9 | 62 | 12 |
| 10 | L10 | 2 | 26 |

Finetuning of the ligand O-alkyl R' group revealed that 2-naphthylmethyl in L6 may be optimal in terms of both reactivity and stereoinduction (entry 6). Similar (R)-BINOL-derived ligands L7 and L8 showed some selectivity (entries 7-8), while KenPhos L9 containing an NMe$_2$ group and MOP L10 were less satisfactory (entries 9-10). All the ligands can be easily assembled and a typical synthesis of L6 is shown below in Scheme II.

SCHEME II

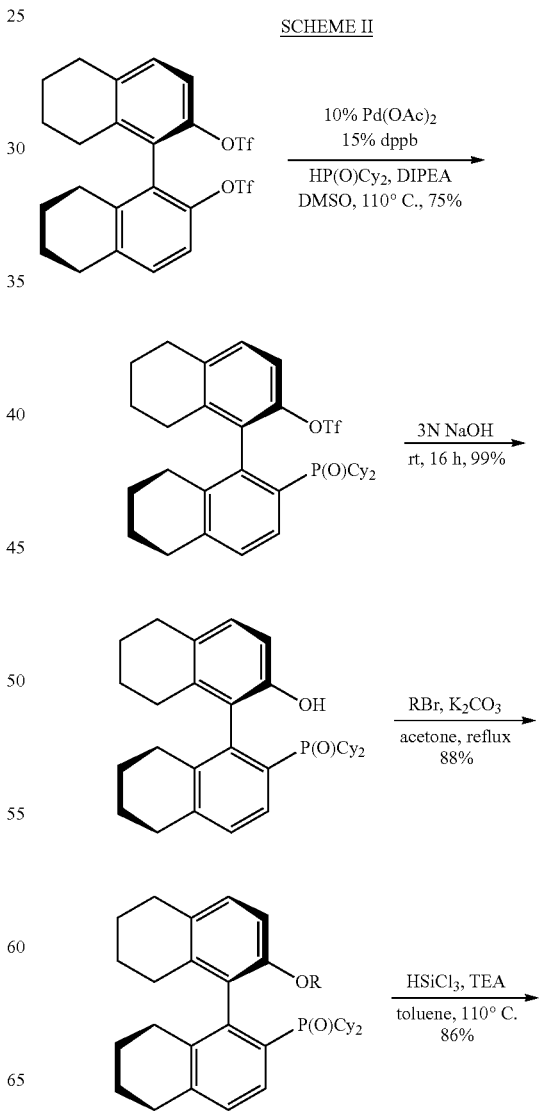

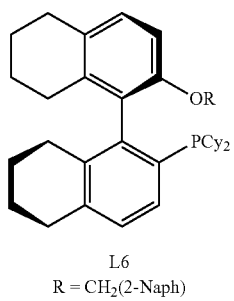

L6
R = CH₂(2-Naph)

The structure of silyl ketene acteals, i.e. (Z)- and (E)-OTMS ketene acetals, also influences the outcome of the asymmetric coupling (Table II).

TABLE II

Effect of Silyl Ketene Acetals

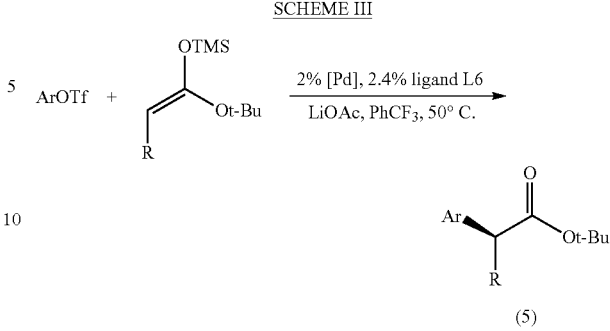

| Entry | R | Yield (%) | EE (%) |
|---|---|---|---|
| 1 | Me | 99 | 5 |
| 2 | Et | 99 | 5 |
| 3 | Cy | 99 | 67 |
| 4 | t-Bu | 99 | 90 |
| 5 | 2-Naph | 99 | 52 |
| 6 | t-Bu[a] | 95 | 50 |

[a](Z)-O-TMS ketene acetal.

As shown in Table II, the size of R groups in the (E)-O-TMS ketene acetals affects the ee significantly (entries 1-5). For instance, <10% ee was observed if R was methyl or ethyl (entries 1-2), while 90% ee was achieved when R was t-butyl (entry 4). In addition, the geometry of the O-TMS ketene acetals is surprisingly very important. For example, the (E)-isomer afforded 90% ee, while the (Z)-isomer only provided a modest 50% ee (entry 4 versus 6). This result may indicate that no free enolate anion is produced from the silyl ketene acetal, since geometric isomers of the former can quickly equilibrate. These results also contradict the common belief that enantiomeric (C)-bound Pd-enolates, after transmetalation, undergo fast equilibration via the (O)-bound form before reductive elimination. Such a fast equilibration does not seem to exist under these conditions. The corresponding C-TMS ketene acetal of t-butyl propionate did not react at all. Finally, the corresponding (E)-O-t-butyldimethylsilyl ketene acetal was completely unreactive.

As shown in Scheme III, the Pd/L6 catalyst can be applied to couplings of various aryl triflates.

SCHEME III

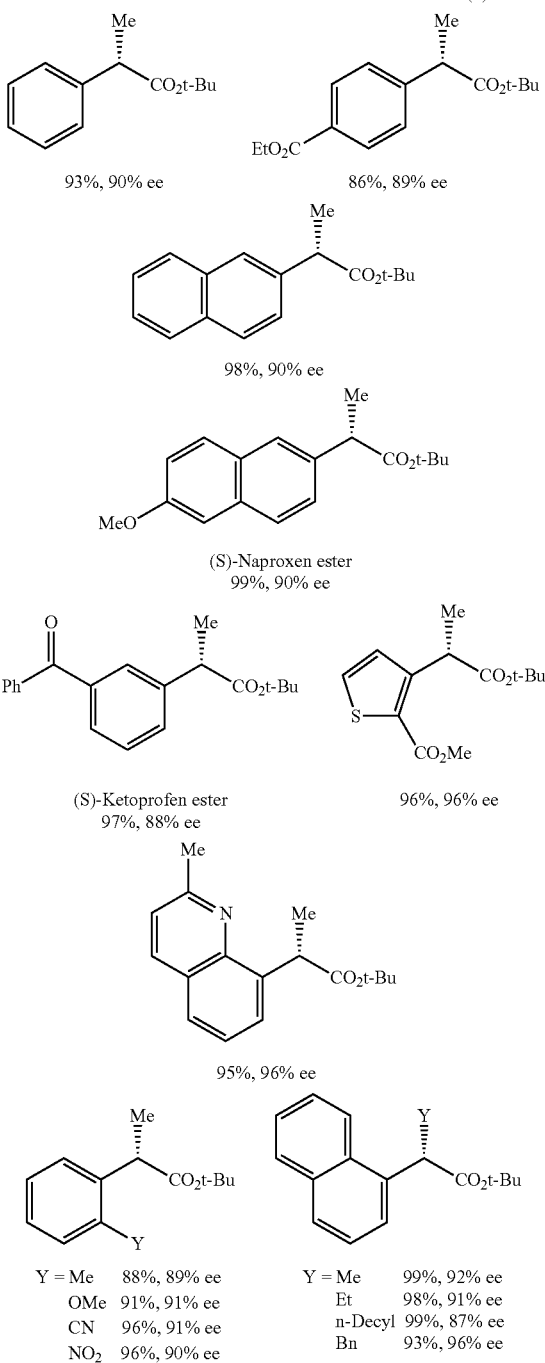

Both electron-donating and -withdrawing groups may be present in aryl group (Ar). These groups may be located on the hindered ortho-position, as well as in the meta- and para-position of the aromatic rings. The conditions are also compatible with sensitive functional groups such as nitro, nitrile, ester and ketone substituents. The aryl group (Ar) may also include heteroaryl groups. Two examples of heteroaryl triflates are included to illustrate the generality of the method. Moreover, three more examples of silyl ketene acetals with α-alkyl substituents can couple efficiently with high ee. The reaction can be easily scaled up to produce 1.2 gram of (S)-Naproxen, after acidic hydrolysis of the tert-butyl ester (eq 6). The product ee can be improved from 92% to 99% after a simple crystallization. The configuration of the new stereocenter was assigned to be (S) by comparison with reported optical rotation of (S)-Naproxen.

The disclosure provides the first examples of α-arylation of esters to form tertiary centers with high ee. The combination of silyl ketene acetals and a mild activator make it possible to avoid racemization and/or double arylation of the resulting monoarylation products. The method is applicable to a gram-scale synthesis of (S)-Naproxen in 92% ee as well as other complex products.

EXAMPLES

The following examples are provided in order to demonstrate and further illustrate certain preferred embodiments and aspects of the present invention and are not to be construed as limiting the scope thereof.

General Information $^1$H NMR spectra were acquired at 0.400 MHz or 300 MHz and chemical shifts were recorded relative to SiMe$_4$ (δ 0.00) or residual protiated solvents (CDCl$_3$: δ7.26; C$_6$D$_6$: δ7.16). Multiplicities were given as: s (singlet), d (doublet), t (triplet), q (quartet) and m (multiplet). The number of protons (n) for a given resonance was indicated by nH. Coupling constants were reported as a J value in Hz. $^{13}$C NMR spectra were obtained at 100 MHz on 400 MHz or 75 MHz on 300 MHz instruments and chemical shifts were recorded relative to solvent resonance (CDCl$_3$: δ 77.23; C$_6$D$_6$: δ 128.0). Proof of purity of new compounds was demonstrated with copies of $^1$H, $^{13}$C, $^{31}$P and $^{19}$F NMR spectra.

Glassware was dried at 120° C. for at least 3 hours before use. Anhydrous α,α,α-trifluorotoluene (Aldrich) was degassed by argon bubbling and then stored over activated 4 Å molecular sieve beads in the glove box before use. Dry benzene (Fluka), dimethyl sulfoxide (DMSO, Fluka), N-methyl-2-pyrrolidone (NMP, Aldrich), and cyclopentyl methyl ether (Aldrich) were used without further purification and were stored in the glove box. Hexamethylphosphoramide (HMPA, Aldrich) was dried over activated 4 Å molecular sieve beads. Dry toluene, hexane, diethyl ether and dichloromethane were collected from a solvent purification system containing a column of activated alumina (1 m×2) under argon. Dry tetrahydrofuran (THF) was freshly distilled from sodium/benzophenone under argon before use. Dry diisopropylethylamine (DIPEA), triethylamine (TEA) and trimethylsilyl chloride (TMSCl) were distilled from CaH$_2$ under argon before use. Diisopropylamine was distilled from anhydrous KOH under argon before use. Xylene (a mixture of isomers) was distilled from sodium under argon before use. All of anhydrous solvents were stored in Schlenk tubes in the glove box.

Unless noted otherwise, commercially available chemicals were used without further purification. PdMe$_2$ (TMEDA) and (R)-KenPhos were prepared according to reported procedures. The GC internal standard, n-dodecane was degassed and dried over activated 4 Å molecular sieve beads before use. Anhydrous lithium acetate (Aldrich) was dissolved in acetic acid, then concentrated and dried in a vacuum oven (−29 in Hg at 120° C.) for 12 hours before use.

Flash chromatography was performed using Merck 40-63D 60 Å silica gel. GC and GC/MS analysis was conducted with Agilent J&W GC column DB-5MS-UI. Chiral HPLC analysis was performed on a Shimadzu LC-20AD instrument using Daicel Chiracel columns at 25° C. Optical rotation was measured using a JASCO P-1030 Polarimeter equipped with a sodium vapor lamp at 589 nm and the concentration of samples was denoted as c. X-ray crystallography analysis of single crystals was performed on a Bruker X8 APEX X-Ray diffractometer.

Synthesis of Chiral Phosphines L1-6

The synthesis of chiral phosphines L1-6 is shown below in Scheme IV.

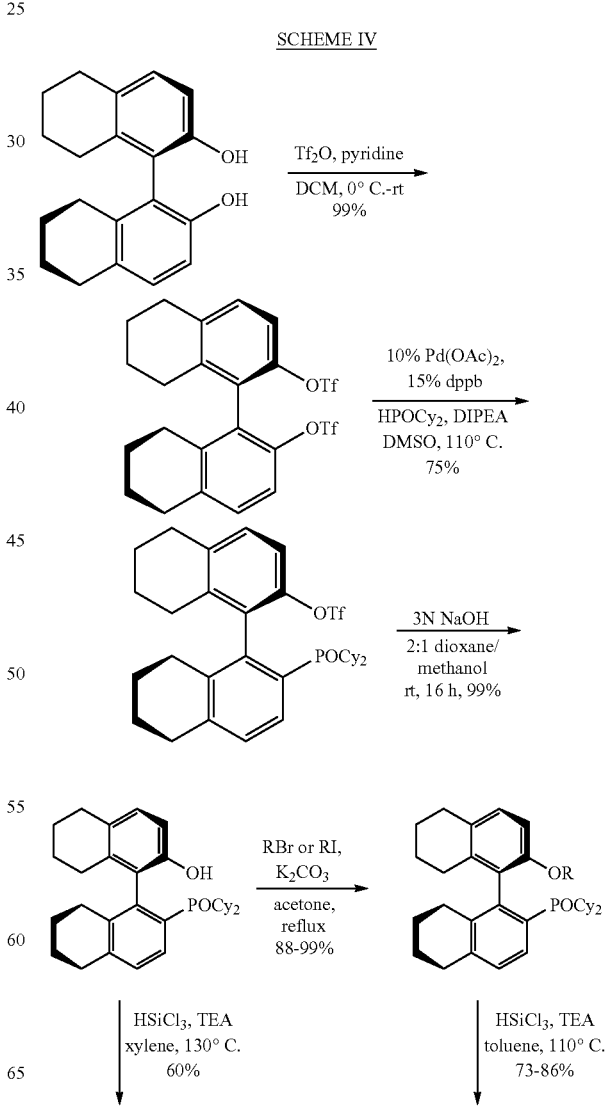

SCHEME IV

-continued

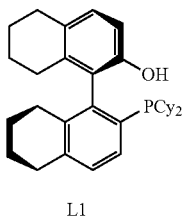

L1

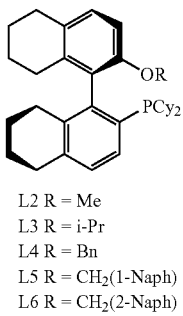

L2 R = Me
L3 R = i-Pr
L4 R = Bn
L5 R = CH₂(1-Naph)
L6 R = CH₂(2-Naph)

Synthesis of Dicyclohexylphosphine Oxide
[14717-29-4]

The compound was prepared according to a reported procedure. Under argon, a 1-liter two-necked round bottom flask (RBF) was charged with magnesium turnings (13.2 g, 550 mmol) and 50 mL of dry diethyl ether. Then a crystal of iodine was added, followed by chlorocyclohexane (7.5 g, 63 mmol) over 5 min without stirring. After addition of another portion of 150 mL of dry diethyl ether, the rest of chlorocyclohexane (51.8 g, 437 mmol) in 25 mL of dry ether was added dropwise over ~30 min in such a rate that a gentle reflux was maintained. After completion of the addition, the reaction mixture was refluxed for another 45 min. Then the mixture was diluted with 500 mL of dry THF, and cooled to 0° C. in an ice bath. A solution of diethyl phosphate (21.0 g, 152 mmol) in 20 mL of dry THF was added into the Grignard reagent dropwise over ~10 min. After the addition, the mixture was stirred at 0° C. for another 30 min and then at 25° C. for 16 h. At the end of the reaction, the mixture was cooled to 0° C. in an ice bath, and quenched with 0.1 N HCl (380 mL). After stirring at 25° C. for 5 min, the organic layer was separated and the insoluble salt was removed by filtering through a pad of CELITE® with ethyl acetate washings (200 mL). The organic layer in the filtrate was separated and combined with the first organic layer, dried over MgSO₄, and concentrated on a rotary evaporator. The residue was purified by Kugelrohr distillation (fraction at ~120° C. at 300 mTorr) to give the target compound (27.6 g, 85%) as white solid. ¹H NMR (400 MHz, CDCl₃): δ 6.31 (dt, $J_{HP}$=433.6 Hz, $J_{HH}$=2.8 Hz, 1H), 2.01-1.22 (m, 22H). ³¹P{1H} NMR (162 MHz, CDCl₃): δ 49.4.

(R)-5,5',6,6',7,7',8,8'-Octahydro-1,1'-binaphthyl-2,2'-diol [65355-14-8]

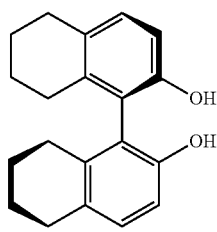

The compound was prepared according to a reported procedure. Acetic acid (145 mL) was added to a 500 mL flask containing (R)-BINOL (5.18 g, 18.1 mmol) and PtO₂ (0.52 g, 2.1 mmol). The flask was evacuated and backfilled with H₂ from an inlet three times. The suspension was stirred with a balloon of H₂ gas on top for 36 h at 25° C. At the end of the reaction, the reaction mixture was filtered through a pad of CELITE® with ethyl acetate washings (150 mL). Concentration of the organic layer yielded pure (R)—H₈-BINOL as a white solid (5.29 g, 18.0 mmol, 99%). ¹H NMR (400 MHz, CDCl₃): δ 7.07 (d, J=8.4 Hz, 2H), 6.83 (d, J=8.4 Hz, 2H), 4.54 (s, 2H), 2.75 (pseudotriplet, J=6.0 Hz, 4H), 2.33-2.26 (m, 2H), 2.20-2.13 (m, 2H), 1.77-1.64 (m, 8H).

(R)-2,2'-Bis(trifluoromethanesulfonate)-5,5',6,6',7,7',8,8'-octahydro-1,1'-binaphthyl [159496-89-6]

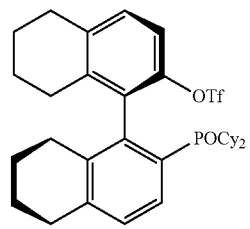

Under argon, (R)—H₈-BINOL (5.88 g, 20 mmol) was dissolved in 100 mL of dry dichloromethane in a 250 mL Schlenk flask. Analytical-grade pyridine (4.2 mL, 52 mmol) was added and the solution was cooled to 0° C. Then triflic anhydride (7.4 mL, 44 mmol) was added slowly via syringe over 5 min. The reaction mixture was allowed to warm up to 25° C. and kept stirred at 25° C. for 12 h. At the conclusion of the reaction, the mixture was passed through a pad of silica gel (~100 g) and washed with 1:30 ethyl acetate/hexane until no more product was eluted out (monitored by TLC). Concentration of the filtrate on a rotary evaporator gave the pure product (11.1 g, 99%) as white solid. ¹H NMR (400 MHz, CDCl₃): δ 7.22 (d, J=8.4 Hz, 2H), 7.15 (d, J=8.4 Hz, 2H), 2.85 (pseudotriplet, J=6.0 Hz, 4H), 2.38-2.46 (m, 2H), 2.25-2.32 (m, 2H), 1.67-1.84 (m, 8H). ¹⁹F NMR (376 MHz, CDCl₃): δ -74.5.

(R)-2-(Dicyclohexylphosphinyl)-2'-trifluoromethanesulfonate-5,5',6,6',7,7',8,8'-octa-hydro-1,1'-binaphthyl In an argon-filled glove box, (R)-2,2'-bis(trifluoromethane-sulfonyloxy)-5,5',6,6',7,7',8,8'-octahydro-1,1'-binaphthyl (3.65 g, 5.84 mmol), dicyclohexyl-phosphine oxide (1.70 g, 7.94 mmol), Pd(OAc)₂ (131 mg, 0.58 mmol) and dppb (374 mg, 0.88 mmol) were added into a dry 100 mL Schlenk tube. Then dry DMSO (30 mL) was added, followed by N,N'-diisopropyl-ethylamine (4.1 mL, 23.4 mmol) via syringe in one portion. The resulting mixture was stirred at 25° C. for 20 min and then heated in a 110° C. oil bath with stirring for 24 hours. At the end of the reaction, the mixture was cooled to 25° C. and DMSO was removed under vacuum. The resulting crude product was diluted with ethyl acetate (200 mL), washed with water, brine and finally filtered through a pad of CELITE®. The filtrate was concentrated under vacuum and the resulting residue was purified by flash chromatography (ethyl acetate/hexane 1:1 to 2:1) to give the target phosphine oxide (3.06 g, 75%) as white foam. $^1$H NMR (300 MHz, CDCl$_3$): δ 7.17-7.14 (m, 2H), 7.09 (d, J=8.6 Hz, 1H), 7.03 (d, J=8.6 Hz, 1H), 2.90-2.76 (m, 4H), 2.51-2.35 (m, 2H), 2.19-2.09 (m, 2H), 1.96-1.64 (m, 20H), 1.35-1.14 (m, 10H). $^{13}$C NMR (75 MHz, CDCl$_3$): δ 145.2, 141.5 (d, J$_{CP}$=2.4 Hz), 140.0 (d, J$_{CP}$=4.2 Hz), 138.6, 138.3 (d, J$_{CP}$=8.7 Hz), 136.7, 132.4 (d, J$_{CP}$=3.0 Hz), 129.7, 128.6 (d, J$_{CP}$=11.8 Hz), 128.0 (d, J$_{CP}$=11.2 Hz), 127.2 (d, J$_{CP}$=83.1 Hz), 118.4 (q, J$_{CF}$=324.0 Hz), 117.5, 38.5 (d, J$_{CP}$=63.6 Hz), 37.7 (d, J$_{CP}$=71.5 Hz), 30.4, 29.6, 28.3, 27.3, 27.1 (d, J$_{CP}$=3.9 Hz), 26.95-26.85 (3 overlapping signals), 26.7 (d, J$_{CP}$=2.5 Hz), 26.33, 26.29, 26.15, 26.12, 25.7 (d, J$_{CP}$=2.7 Hz), 25.5 (d, J$_{CP}$=2.6 Hz), 23.1, 22.8, 22.7, 22.6. Some doublets due to C—P couplings in the aliphatic region cannot be assigned due to complexity of the spectrum and they are listed as singlets. $^{31}$P {1H} NMR (121 MHz, CDCl$_3$): δ 45.6. $^{19}$F NMR (282 MHz, CDCl$_3$): δ −75.6. ESI-MS: Calcd for C$_{33}$H$_{43}$F$_3$O$_4$PS (M+H)$^+$: 623.26. Found: 623.31.

(R)-2-(Dicyclohexylphosphinyl)-2'-hydroxy-5,5',6, 6',7,7',8,8'-octahydro-1,1'-binaphthyl

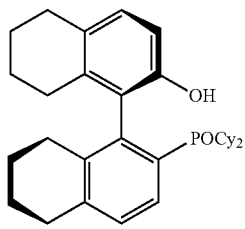

Under argon, (R)-2-(dicyclohexylphosphinyl)-2-(trifluoro-methanesulfonyloxy)-5,5',6,6',7,7',8,8'-octahydro-1,1'-binaphthyl (1.50 g, 2.41 mmol) was dissolved in a 2:1 mixed solvent of dioxane/methanol (20 mL) in a 100 mL RBF. The solution was chilled to 0° C. and then 10 mL of 3.0 N aqueous NaOH solution was added. The resulting mixture was stirred at 25° C. for 12 hours. At the end of the reaction, the mixture was chilled to 0° C. and concentrated HCl (~2.5 mL) was slowly added to adjust pH to ~3. After removal of organic solvents on a rotary evaporator, the residue was diluted with ethyl acetate (150 mL), washed with brine and dried over anhydrous MgSO$_4$. The organic phase was concentrated on a rotary evaporator to afforded the title compound (1.18 g, 99%) as off-white solid. It was directly used in the next step without further purification. $^1$H NMR (400 MHz, CDCl$_3$): δ 7.72 (s, 1H), 7.29 (dd, J$_{PH}$=10.1 Hz, J$_{HH}$=8.0 Hz, 1H), 7.12 (dd, J$_{PH}$=2.5 Hz, J$_{HH}$=8.0 Hz, 1H), 6.99 (d, J=8.4 Hz, 1H), 6.91 (d, J=8.4 Hz, 1H), 2.87-2.68 (m, 4H), 2.22-1.50 (m, 26H), 1.32-0.97 (m, 8H). $^{13}$C NMR (100 MHz, CDCl$_3$): δ 152.1, 142.8 (d, J$_{CP}$=6.0 Hz), 142.1 (d, J$_{CP}$=2.4 Hz), 138.9 (d, J$_{CP}$=9.2 Hz), 135.2, 130.5, 130.1 (d, J$_{CP}$=2.8 Hz), 130.0, 129.0 (d, J$_{CP}$=10.0 Hz), 127.8 (d, J$_{CP}$=11.2 Hz), 127.0 (d, J$_{CP}$=85.3 Hz), 118.9, 37.4 (d, J$_{CP}$=65.7 Hz), 35.4 (d, J$_{CP}$=67.2 Hz), 30.5, 29.7, 28.0, 27.2, 27.1, 26.9, 26.84, 26.80, 26.7, 26.6, 26.4, 26.3 (d, J$_{CP}$=0.8 Hz), 26.13, 26.11, 26.08, 26.0 (d, J$_{CP}$=2.4 Hz), 25.9 (d, J$_{CP}$=3.9 Hz), 25.3, 23.6, 23.4, 23.3, 22.6. Some doublets due to C—P couplings in the aliphatic region cannot be assigned due to complexity of the spectrum and they are listed as singlets. $^{31}$P {1H} NMR (162 MHz, CDCl$_3$): δ 49.1. ESI-MS: Calcd for C$_{32}$H$_{44}$O$_2$P (M+H)$^+$: 491.31. Found: 491.49.

(R)-2-(Dicyclohexylphosphinyl)-2'-methoxy-5,5',6, 6',7,7',8,8'-octahydro-1,1'-binaphthyl

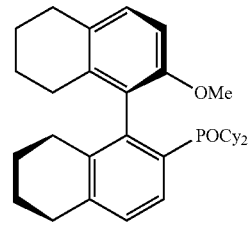

Under argon, to a 25 mL two-necked RBF equipped with a condenser was added (R)-2-(dicyclohexylphosphinyl)-2-hydroxy-5,5',6,6',7,7',8,8'-octahydro-1,1'-binaphthyl (49 mg, 0.10 mmol) and anhydrous K$_2$CO$_3$ (79 mg, 0.50 mmol). Then analytical-grade acetone (5 mL) was added, followed by iodomethane (50 uL, 0.80 mmol). The resulting mixture was refluxed under argon for 24 hours until all the starting material was consumed (monitored by $^{31}$P NMR spectroscopy). After the mixture was cooled to 25° C., it was filtered through CELITE® with ethyl acetate washings (10 mL×2). The filtrate was concentrated on a rotary evaporator and the resulting residue was purified by flash chromatography (ethyl acetate/hexane 2:1) to afford the desired compound (50 mg, 99%) as yellow oil. $^1$H NMR (300 MHz, CDCl$_3$): δ 7.45 (dd, J$_{PH}$=10.6 Hz, J$_{HH}$=8.0 Hz, 1H), 7.11 (dd, J$_{PH}$=2.1 Hz, J$_{HH}$=8.0 Hz, 1H), 7.04 (d, J$_{HH}$=8.4 Hz, 1H), 6.69 (d, J$_{HH}$=8.4 Hz, 1H), 3.64 (s, 3H), 2.85-2.70 (m, 4H), 2.35-1.01 (m, 34H). $^{13}$C NMR (75 MHz, CDCl$_3$): δ 154.0, 142.4 (d, J$_{CP}$=6.4 Hz), 140.7 (d, J$_{CP}$=2.6 Hz), 137.4 (d, J$_{CP}$=9.5 Hz), 136.9, 129.5 (d, J$_{CP}$=9.5 Hz), 129.4, 129.1, 128.2, 127.7, 127.6, 127.5, 127.1, 107.7, 55.1, 38.4 (d, J$_{CP}$=65.4 Hz), 36.8 (d, J$_{CP}$=66.4 Hz), 30.5, 29.4, 28.0, 27.3-26.8 (multiple overlapping signals), 26.2-25.9 (multiple overlapping signals), 23.5, 23.33, 23.30, 22.8. Some doublets due to C—P couplings cannot be assigned due to complexity of the spectrum and they are listed as singlets. $^{31}$P {1H} NMR (121 MHz, CDCl$_3$): δ 45.7. ESI-MS: Calcd for C$_{33}$H$_{45}$O$_2$P (M+H)$^+$: 505.32. Found: 505.51.

(R)-2-(Dicyclohexylphosphinyl)-2'-isopropoxy-5,5', 6,6',7,7',8,8'-octa-hydro-1,1'-binaphthyl

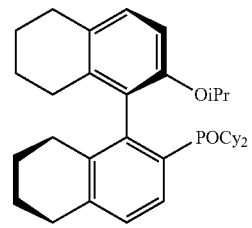

The same procedure as described above was used. (R)-2-(Dicyclo-hexylphosphinyl)-2-hydroxy-5,5',6,6',7,7',8,8'-octahydro-1,1'-binaphthyl (49 mg, 0.10 mmol), 2-iodopropane (79 uL, 0.80 mmol), K$_2$CO$_3$ (79 mg, 0.50 mmol) and acetone (5 mL) were used, and the reaction was finished after refluxing for 2 days. The crude product was purified by flash chromatography (ethyl acetate/hexane 2:1), which afforded the desired compound (50 mg, 94%) as yellow oil. $^1$H NMR (400 MHz, CDCl$_3$): δ 7.43 (dd, J$_{PH}$=10.6 Hz, J$_{HH}$=8.0 Hz, 1H), 7.09 (dd, J$_{PH}$=2.1 Hz, J$_{HH}$=8.0 Hz, 1H), 6.99 (d, J$_{HH}$=8.4 Hz, 1H), 6.68 (d, J$_{HH}$=8.4 Hz, 1H), 4.38 (septet, J=6.0 Hz, 1H), 2.85-2.72 (m, 4H), 2.38-1.02 (m, 40H). $^{13}$C NMR (100 MHz, CDCl$_3$): δ 152.6, 142.7 (d, J$_{CP}$=6.6 Hz), 140.4 (d, J$_{CP}$=2.6 Hz), 137.2, 137.0 (d, J$_{CP}$=9.7 Hz), 129.5 (d, J$_{CP}$=9.5 Hz), 128.90, 128.87, 128.6 (d, J$_{CP}$=2.6 Hz), 127.8 (d, J$_{CP}$=84.4 Hz), 127.2 (d, J$_{CP}$=11.9 Hz), 110.2, 69.6, 38.2 (d, J$_{CP}$=65.4 Hz), 36.6 (d, J$_{CP}$=66.1 Hz), 30.5, 29.4, 28.2, 27.3, 27.1-26.9 (multiple overlapping signals), 26.3, 26.1, 26.0 (d, J$_{CP}$=2.8 Hz), 25.9 (d, J$_{CP}$=2.5 Hz), 23.6, 23.39, 23.38, 23.0, 22.9, 22.4. Some doublets due to C—P couplings in the aliphatic region cannot be assigned due to complexity of the spectrum and they are listed as singlets. $^{31}$P {1H} NMR (162 MHz, CDCl$_3$): δ 45.4. ESI-MS: Calcd for C$_{35}$H$_{49}$O$_2$P (M+H)$^+$: 533.35. Found: 533.48.

(R)-2-(Dicyclohexylphosphinyl)-2'-benzyloxy-5,5',6,6',7,7',8,8'-octahydro-1,1'-binaphthyl

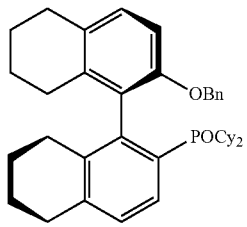

Under argon, to a 25 mL two-necked. RBF equipped with a condenser was added (R)-2-(dicyclohexylphosphinyl)-2-hydroxy-5,5',6,6',7,7',8,8'-octahydro-1,1'-binaphthyl (196 mg, 0.40 mmol) and anhydrous K$_2$CO$_3$ (276 mg, 2.0 mmol). Then analytical-grade acetone (5 mL) was added, followed by benzyl bromide (190 uL, 1.6 mmol). The resulting mixture was refluxed under argon for 3 days until all the starting material was consumed (monitored by $^{31}$P NMR spectroscopy). After the mixture was cooled to 25° C., it was filtered through a pad of CELITE® with ethyl acetate washings (10 mL×2). The filtrate was concentrated on a rotary evaporator and the resulting residue was purified by flash chromatography (ethyl acetate/hexane 3:2), which afforded the desired compound (231 mg, 99%) as white foam. $^1$H NMR (400 MHz, CDCl$_3$): δ 7.38 (dd, J$_{PH}$=10.4 Hz, J$_{HH}$=8.0 Hz, 1H), 7.23-7.17 (m, 3H), 7.14 (dd, J$_{PH}$=2.1 Hz, J$_{HH}$=8.0 Hz, 1H), 7.07-7.05 (m, 2H), 7.02 (d, J=8.4 Hz, 1H), 6.74 (d, J=8.4 Hz, 1H), 4.96 (s, 2H), 2.89-2.74 (m, 4H), 2.48-0.86 (m, 34H). $^{13}$C NMR (100 MHz, CDCl$_3$): δ 153.0, 142.8 (d, J$_{CP}$=5.9 Hz), 140.6 (d, J$_{CP}$=2.5 Hz), 138.1, 137.4 (d, J$_{CP}$=9.4 Hz), 137.2, 129.6, 129.3 (d, J$_{CP}$=10.0 Hz), 129.0, 128.3, 128.25, 127.6 (d, J$_{CP}$=84.3 Hz), 127.4 (d, J$_{CP}$=11.5 Hz), 127.3, 126.3, 109.2, 69.2, 38.3 (d, J$_{CP}$=2.8 Hz), 36.7 (d, J$_{CP}$=2.8 Hz), 30.6, 29.4, 28.2, 27.3, 27.0, 26.95 (d, J$_{CP}$=1.7 Hz), 26.9 (d, J$_{CP}$=1.9 Hz), 26.83-26.76 (3 overlapping signals), 26.1-26.0 (3 overlapping signals), 25.8 (d, J$_{CP}$=2.8 Hz), 25.6 (d, J$_{CP}$=2.6 Hz), 23.6, 23.34, 23.31, 22.9. Some doublets due to C—P couplings in the aliphatic region cannot be assigned due to complexity of the spectrum and they are listed as singlets. $^{31}$P {1H} NMR (162 MHz, CDCl$_3$): δ 45.6. ESI-MS: Calcd for C$_{39}$H$_{49}$O$_2$P (M+H)$^+$: 581.35. Found: 581.47.

(R)-2-(Dicyclohexylphosphinyl)-2'-(1-naphthylmethoxy)-5,5',6,6',7,7',8,8'-octahydro-1,1'-binaphthyl

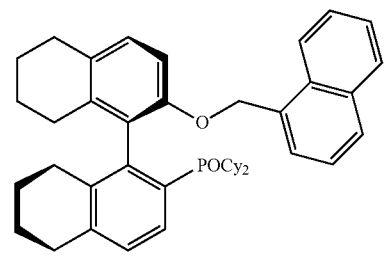

The same procedure as above was used. (R)-2-(Dicyclohexylphosphinyl)-2-hydroxy-5,5',6,6',7,7',8,8'-octahydro-1,1'-binaphthyl (196 mg, 0.40 mmol), 1-(bromomethyl)naphthalene (354 mg, 1.6 mmol), K$_2$CO$_3$ (276 mg, 2.0 mmol) and acetone (5 mL) were used. The reaction was refluxed for 3 days until completion. The crude product was purified by flash chromatography (ethyl acetate/hexane 1:1), which afforded the desired compound (248 mg, 98%) as white foam. $^1$H NMR (400 MHz, CDCl$_3$): δ 7.81 (d, J=8.0 Hz, 1H), 7.77 (d, J=8.4 Hz, 1H), 7.71 (d, J=8.0 Hz, 1H), 7.47-7.38 (m, 2H), 7.35-7.28 (m, 2H), 7.21 (d, J=6.8 Hz, 1H), 7.12 (dd, J$_{PH}$=2.0 Hz, J=8.0 Hz, 1H), 7.06 (d, J=8.4 Hz, 1H), 6.92 (d, J=8.4 Hz, 1H), 5.44-5.36 (m, 2H), 2.87-2.73 (m, 4H), 2.47-0.78 (m, 34H). $^{13}$C NMR (100 MHz, CDCl$_3$): δ 153.2, 143.1 (d, J$_{CP}$=5.8 Hz), 140.7 (d, J$_{CP}$=2.6 Hz), 137.5 (d, J$_{CP}$=9.4 Hz), 137.2, 133.6, 133.3, 131.0, 129.8, 129.2, 129.0, 128.7, 128.6 (d, J$_{CP}$=2.9 Hz), 128.1, 127.6 (d, J$_{CP}$=84.6 Hz), 127.4 (d, J$_{CP}$=11.6 Hz), 126.2, 125.7, 125.5, 125.0, 123.4, 109.5, 68.0, 38.4 (d, J$_{CP}$=65.8 Hz), 36.8 (d, J$_{CP}$=66.4 Hz), 30.6, 29.5, 28.2, 27.4, 27.0 (d, J$_{CP}$=1.8 Hz), 26.9 (d, J$_{CP}$=2.0 Hz), 26.89, 26.8 (d, J$_{CP}$=2.4 Hz), 26.7 (d, J$_{CP}$=2.4 Hz), 26.1-26.0 (3 overlapping signals), 25.8 (d, J$_{CP}$=2.8 Hz), 25.6 (d, J$_{CP}$=2.5 Hz), 23.5, 23.37, 23.35, 22.8. Some doublets due to C—P couplings in the aliphatic region cannot be assigned due to complexity of the spectrum and they are listed as singlets. $^{31}$P {1H} NMR (162 MHz, CDCl$_3$): δ 45.5. ESI-MS: Calcd for C$_{43}$H$_{52}$O$_2$P (M+H)$^+$: 631.37. Found: 631.46.

(R)-2-(Dicyclohexylphosphinyl)-2'-(2-naphthylmethoxy)-5,5',6,6',7,7',8,8'-octahydro-1,1'-binaphthyl

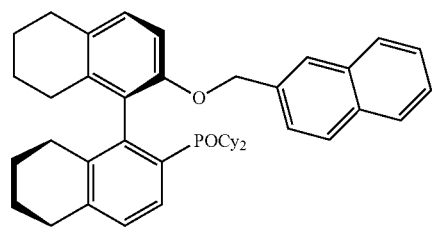

The same procedure as above was used. (R)-2-(Dicyclohexylphosphinyl)-2-hydroxy-5,5',6,6',7,7',8,8'-octahydro-1,1'-binaphthyl (490 mg, 1.0 mmol), 2-(bromomethyl)naphthalene (884 mg, 4.0 mmol), $K_2CO_3$ (690 mg, 5.0 mmol) and acetone (12 mL) were used, and the reaction was finished after refluxing for 3 days. The crude product was purified by flash chromato-graphy (ethyl acetate/hexane 1:1), which afforded the desired compound (554 mg, 88%) as white foam. $^1$H NMR (400 MHz, $CDCl_3$): δ 7.78-7.76 (m, 1H), 7.71 (d, J=8.4 Hz, 1H), 7.62-7.60 (m, 1H), 7.54-7.39 (m, 4H), 7.21 (m, 2H), 7.04 (d, J=8.4 Hz, 1H), 6.79 (d, J=8.4 Hz, 1H), 5.11 (s, 2H), 2.91-2.49 (m, 4H), 2.53-0.80 (m, 34H). $^{13}$C NMR (100 MHz, $CDCl_3$): 153.0, 143.0 (d, $J_{CP}$=5.9 Hz), 140.7 (d, $J_{CP}$=2.7 Hz), 137.5 (d, $J_{CP}$=9.4 Hz), 137.3, 135.6, 133.5, 132.9, 129.7, 129.4 (d, $J_{CP}$=9.9 Hz), 129.1, 128.3 (d, $J_{CP}$=2.9 Hz), 127.92, 127.90, 127.84 (d, $J_{CP}$=75.0 Hz), 127.79, 127.5 (d, $J_{CP}$=11.3 Hz), 126.2, 125.8, 125.0, 124.4, 109.2, 69.2, 38.4 (d, $J_{CP}$=65.6 Hz), 36.7 (d, $J_{CP}$=66.4 Hz), 30.6, 29.5, 28.2, 27.4, 27.0 (d, $J_{CP}$=2.5 Hz), 26.9, 26.8 (d, $J_{CP}$=2.1 Hz), 26.81, 26.78, 26.1, 26.05, 26.02, 25.9 (d, $J_{CP}$=2.7 Hz), 25.6 (d, $J_{CP}$=2.4 Hz), 23.6, 23.38, 23.35, 22.9. Some doublets due to C—P couplings in the aliphatic region cannot be assigned due to complexity of the spectrum and they are listed as singlets. $^{31}$P {1H} NMR (162 MHz, $CDCl_3$): δ 45.5. ESI-MS: Calcd for $C_{43}H_{52}O_2P$ (M+H)$^+$: 631.37. Found: 631.49.

(R)-2-(Dicyclohexylphosphino)-2'-hydroxy-5,5',6,6',7,7',8,8'-octahydro-1,1'-binaphthyl

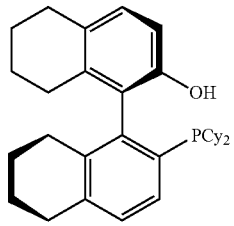

Under argon, to 25 mL Schlenk tube was added the corresponding phosphine oxide (147 mg, 0.3 mmol), triethylamine (1.6 mL, 12.0 mmol) and dry xylene (mixture of isomers, 5.0 mL). After the resulting solution was cooled to 0° C., trichlorosilane (0.30 mL, 3.0 mmol) was added via a syringe. The Schlenk tube was sealed tightly and the reaction mixture was heated in a 130° C. oil bath for 24 hours until all the starting material was consumed (monitored by $^{31}$P NMR spectroscopy). At the end of the reaction, the mixture was cooled to 25° C. in the glove box and diluted with degassed diethyl ether (10 mL). After the resulting suspension was briefly chilled for 5 minutes in a −30° C. fridge of the glove box, a degassed, saturated $Na_2CO_3$ solution (1.0 mL) was added slowly to quench the reaction. The mixture was dried over $MgSO_4$, filtered through pad of CELITE®, and washed with degassed diethyl ether until no more product was washed out (monitored by TLC). The filtrate was concentrated under vacuum and then purified in the glove box by flash chromatography (diethyl ethyl/hexane 1:10), which afforded the desired compound (85.3 mg, 60%) as white foam. $^1$H NMR (300 MHz, $CDCl_3$): δ 7.38 (d, J=7.8 Hz, 1H), 7.13 (d, J=7.8 Hz, 1H), 7.01 (d, J=8.3 Hz, 1H), 6.74 (d, J=8.3 Hz, 1H), 4.14 (s, 1H), 2.85-2.74 (m, 4H), 2.34-1.04 (m, 34H). $^{13}$C NMR (75 MHz, $CDCl_3$): δ 149.9 (d, $J_{CP}$=1.6 Hz), 142.5 (d, $J_{CP}$=31.9 Hz), 139.3, 137.5 (d, $J_{CP}$=6.0 Hz), 135.6 (d, $J_{CP}$=2.0 Hz), 134.3 (d, $J_{CP}$=18.4 Hz), 130.7 (d, $J_{CP}$=3.7 Hz), 129.8, 129.1, 129.0, 126.7 (d, $J_{CP}$=7.1 Hz), 112.4, 34.9 (d, $J_{CP}$=15.2 Hz), 34.6 (d, $J_{CP}$=14.5 Hz), 30.8, 30.6, 30.5, 30.3, 30.1, 30.0, 29.9, 29.5, 28.5 (d, $J_{CP}$=3.0 Hz), 27.9 (d, $J_{CP}$=2.0 Hz), 27.7, 27.6-27.5 (3 overlapping signals), 26.7 (d, $J_{CP}$=7.7 Hz), 23.5, 23.4, 23.3, 22.9. Some doublets due to C—P couplings in the aliphatic region cannot be assigned due to complexity of the spectrum and they are listed as singlets. $^{31}$P {1H} NMR (121 MHz, $CDCl_3$): δ −9.6. [a]$^{20}_D$=+27.8° (c=1.4, $CH_2Cl_2$). HRMS: Calcd for $C_{32}H_{44}OP$ (M+H)$^+$: 475.31. Found: 475.47.

(R)-2-(Dicyclohexylphosphino)-2'-methoxy-5,5',6,6',7,7',8,8'-octahydro-1,1'-binaphthyl

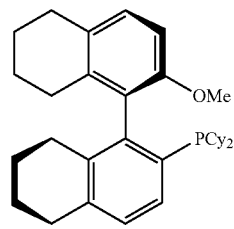

Under argon, a 25 mL Schlenk tube was charged with the corresponding phosphine oxide (50.0 mg, 0.1 mmol), triethylamine (0.50 mL, 4.0 mmol) and dry toluene (2.0 mL). After the resulting solution was cooled to 0° C., trichlorosilane (0.1 mL, 1.0 mmol) was added by syringe. The resulting mixture was heated with stirring in a 110° C. oil bath for 12 hours, until all the starting material was consumed (monitored by $^{31}$P NMR spectroscopy). At the conclusion of the reaction, the mixture was cooled to 25° C. in the glove box and diluted with degassed diethyl ether (10 mL). After the resulting suspension was briefly chilled for 5 minutes in a −30° C. fridge of the glove box, a degassed, saturated $Na_2CO_3$ solution (1.0 mL) was added to quench the reaction. The mixture was dried over $MgSO_4$, filtered through pad of CELITE®, and washed with degassed diethyl ether until no more product was washed out (monitored by TLC). The filtrate was concentrated under vacuum, and the resulting residue was purified in the glove box by flash chromatography (diethyl ethyl/hexane 1:10), which afforded the desired compound (37.1 mg, 76%) as white foam. $^1$H NMR (300 MHz, $CDCl_3$): δ 7.32 (d, J=7.8 Hz, 1H), 7.09-7.05 (m, 2H), 6.69 (d, J=8.4 Hz, 1H), 3.63 (s, 3H), 2.85-2.72 (m, 4H), 2.32-0.87 (m, 34H). $^{13}$C NMR (75 MHz, $CDCl_3$): δ 154.5 (d, $J_{CP}$=1.6 Hz), 145.6 (d, $J_{CP}$=31.2 Hz), 137.9, 136.1 (d, $J_{CP}$=4.0 Hz), 136.08, 132.4 (d, $J_{CP}$=15.4 Hz), 129.6 (d, $J_{CP}$=2.8 Hz), 129.1 (d, $J_{CP}$=7.3 Hz), 129.0, 128.9, 127.6, 107.2, 54.8, 35.5 (d, $J_{CP}$=15.6 Hz), 33.3 (d, $J_{CP}$=13.5 Hz), 30.5 (d, $J_{CP}$=2.2 Hz), 30.4-30.3 (4 overlapping signals), 30.1, 29.9, 29.6, 29.5, 29.4, 28.3 (d, $J_{CP}$=3.4 Hz), 28.2, 28.0 (d, $J_{CP}$=2.0 Hz), 27.6 (d, $J_{CP}$=1.2 Hz), 27.5 (d, $J_{CP}$=2.6 Hz), 27.4 (d, $J_{CP}$=4.1 Hz), 26.8 (d, $J_{CP}$=5.1 Hz), 23.7, 23.4, 23.38, 23.0. Some doublets due to C—P couplings in the aliphatic region cannot be assigned due to complexity of the spectrum and they are listed as singlets. $^{31}$P NMR (121 MHz, $CDCl_3$): δ −9.0. [a]$^{20}_D$=+34.2° (c=2.4, $CH_2Cl_2$). HRMS: Calcd for $C_{33}H_{46}OP$ (M+H)$^+$: 489.33. Found: 489.49.

(R)-2-(Dicyclohexylphosphino)-2'-isopropoxy-5,5',6,6',7,7',8,8'-octa-hydro-1,1'-binaphthyl

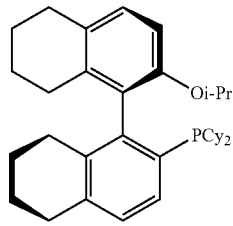

The same procedure as described above was used. The corresponding phosphine oxide (50 mg, 0.09 mmol), truethylamine (0.50 mL, 4.0 mmol), trichlorosilane (0.10 mL, 1.0 mmol) and dry toluene (2 mL) were used. The reaction was finished after heating at 110° C. for 12 hours. The resulting residue was purified by flash chromatography (diethyl ethyl/hexane 1:10), which afforded the desired compound (34 mg, 73%) as white foam. $^1$H NMR (400 MHz, CDCl$_3$): δ 7.29 (d, J=7.6 Hz, 1H), 7.05-7.01 (m, 2H), 6.67 (d, J=8.4 Hz, 1H), 4.40 (septet, J=6.0 Hz, 1H), 2.82-2.70 (m, 4H), 2.33-1.01 (m, 40H). $^{13}$C NMR (100 MHz, CDCl$_3$): δ 153.0 (d, J$_{CP}$=1.1 Hz), 145.9 (d, J$_{CP}$=31.1 Hz), 137.6, 136.4 (d, J$_{CP}$=2.0 Hz), 135.9 (d, J$_{CP}$=6.4 Hz), 132.4 (d, J$_{CP}$=14.9 Hz), 129.9 (d, J$_{CP}$=7.0 Hz), 129.5 (d, J$_{CP}$=2.7 Hz), 128.7, 128.4, 127.2, 109.3, 68.9, 35.5 (d, J$_{CP}$=15.5 Hz), 33.6 (d, J$_{CP}$=13.7 Hz), 30.7, 30.6, 30.5, 30.4, 30.2 (d, J$_{CP}$=10.2 Hz), 29.7, 29.6, 29.5, 28.6 (d, J$_{CP}$=3.9 Hz), 28.0, 27.9, 27.8 (d, J$_{CP}$=1.7 Hz), 27.64, 27.56 (d, J$_{CP}$=2.4 Hz), 27.46, 26.8 (d, J$_{CP}$=5.1 Hz), 23.8, 23.45, 23.44, 23.2, 22.9, 22.4. Some doublets due to C—P couplings in the aliphatic region cannot be assigned due to complexity of the spectrum and they are listed as singlets. $^{31}$P {1H} NMR (162 MHz, CDCl$_3$): δ -9.8. [a]$^{20}$$_D$=+41.0° (c=2.3, CH$_2$Cl$_2$). FIRMS: Calcd for C$_{35}$H$_{50}$OP (M+H)$^+$: 517.36. Found: 517.53.

(R)-2-(Dicyclohexylphosphino)-2'-benzyloxy-5,5',6,6',7,7',8,8'-octa-hydro-1,1'-binaphthyl

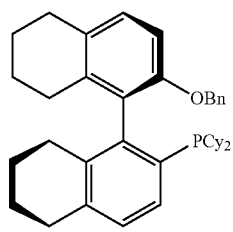

The same procedure as described above was used. The corresponding phosphine oxide (200 mg, 0.34 mmol), triethylamine (1.7 mL, 13.6 mmol), trichlorosilane (0.34 mL, 3.4 mmol) and dry toluene (6 mL) were used. The reaction was finished after heating at 110° C. for 16 hours. The resulting residue was purified by flash chromatography (diethyl ethyl/hexane 1:10), which afforded the desired compound (153 mg, 80%) as white foam. $^1$H NMR (400 MHz, CDCl$_3$): δ 7.30 (d, J=7.6 Hz, 1H), 7.25-7.15 (m, 3H), 7.10-7.06 (m, 2H), 7.03 (d, J=8.4 Hz, 1H), 6.70 (d, J=8.4 Hz, 1H), 4.97 (d, J=12.4 Hz, 1H), 4.90 (d, J=12.4 Hz, 1H), 2.85-2.73 (m, 4H), 2.36-0.75 (m, 34H). $^{13}$C NMR (100 MHz, CDCl$_3$): δ 153.5, 145.5 (d, J$_{CP}$=31.1 Hz), 138.2, 137.9, 136.4 (d, J$_{CP}$=2.1 Hz), 136.0 (d, J$_{CP}$=6.2 Hz), 132.4, 132.2, 129.7 (d, J$_{CP}$=2.8 Hz), 129.4, 128.9, 128.3, 127.5, 127.2, 126.3, 108.7, 68.9, 35.5 (d, J$_{CP}$=15.5 Hz), 33.3 (d, J$_{CP}$=13.2 Hz), 30.6, 30.48, 30.42, 30.3, 30.0 (d, J$_{CP}$=9.2 Hz), 29.6, 29.4, 28.5 (d, J$_{CP}$=3.7 Hz), 27.9, 27.8, 27.5 (d, J$_{CP}$=5.0 Hz), 27.4 (d, J$_{CP}$=6.4 Hz), 26.8, 26.5, 23.8, 23.41, 23.37, 23.2. Some doublets due to C—P couplings in the aliphatic region cannot be assigned due to complexity of the spectrum and they are listed as singlets. $^{31}$P {1H} NMR (162 MHz, CDCl$_3$): δ -9.1. [a]$^{20}$$_D$=+26.3° (c=1.5, CH$_2$Cl$_2$). HRMS: Calcd for C$_{39}$H$_{50}$OP (M+H)$^+$: 565.36. Found: 565.46.

(R)-2-(Dicyclohexylphosphino)-2'-(1-naphthyl-methoxy)-5,5',6,6',7,7',8,8'-octahydro-1,1'-binaphthyl

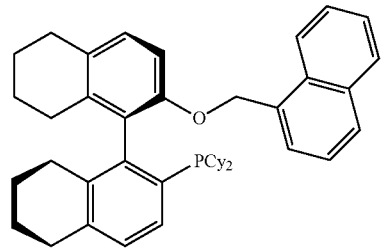

The same procedure as described above was used. The corresponding phosphine oxide (100 mg, 0.16 mmol), triethylamine (0.80 mL, 6.4 mmol), trichlorosilane (0.16 mL, 1.6 mmol) and dry toluene (4 mL) were used. The reaction was finished after heating at 110° C. for 16 hours. The resulting residue was purified in the glove box by flash chromatography (diethyl ethyl/hexane 1:10), which afforded the desired compound (81 mg, 82%) as white foam. $^1$H NMR (300 MHz, CDCl$_3$): δ 7.84-7.80 (m, 2H), 7.72 (d, J=8.8 Hz, 1H), 7.48-7.40 (m, 2H), 7.34-7.29 (m, 2H), 7.24 (d, J=6.8 Hz, 1H), 7.11-7.06 (m, 2H), 6.90 (d, J=8.4 Hz, 1H), 5.45 (d, J=12.8 Hz, 1H), 5.33 (d, J=12.8 Hz, 1H), 2.88-2.71 (m, 4H), 2.39-0.69 (m, 34H). $^{13}$C NMR (100 MHz, CDCl$_3$): δ 153.7 (d, J$_{CP}$=1.21 Hz), 145.5 (d, J$_{CP}$=31.1 Hz), 138.0, 136.5 (d, J$_{CP}$=2.0 Hz), 136.0 (d, J$_{CP}$=6.5 Hz), 133.6, 133.3, 132.4 (d, J$_{CP}$=15.3 Hz), 130.9, 130.0 (d, J$_{CP}$=7.2 Hz), 129.8 (d, J$_{CP}$=2.7 Hz), 129.6, 129.0, 128.8, 128.0, 127.5, 126.2, 125.7, 125.6, 124.9, 123.3, 109.0, 67.7, 35.4 (d, J$_{CP}$=15.4 Hz), 33.4 (d, J$_{CP}$=13.3 Hz), 30.6, 30.5 (d, J$_{CP}$=1.3 Hz), 30.4, 30.3, 30.0 (d, J$_{CP}$=9.7 Hz), 29.6, 29.4, 28.5 (d, J$_{CP}$=3.5 Hz), 27.9, 27.8 (d, J$_{CP}$=2.0 Hz), 27.6 (d, J$_{CP}$=5.2 Hz), 27.5 (d, J$_{CP}$=6.6 Hz), 26.8, 26.5, 23.7, 23.41, 23.36, 23.1. Some doublets due to C—P couplings in the aliphatic region cannot be assigned due to complexity of the spectrum and they are listed as singlets. $^{31}$P NMR (121 MHz, CDCl$_3$): δ -9.6. [a]$^{20}$$_D$=+10.1° (c=1.1, CH$_2$Cl$_2$). HRMS: Calcd for C$_{43}$H$_{52}$OP (M+H)$^+$: 615.38. Found: 615.45.

(R)-2-(Dicyclohexylphosphino)-2'-(2-naphthyl-methoxy)-5,5',6,6',7,7',8,8'-octahydro-1,1'-binaphthyl

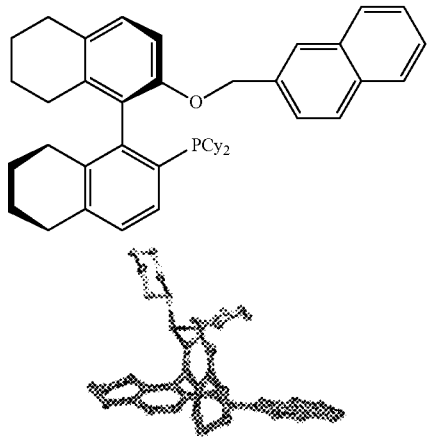

The same procedure as described above was used. The corresponding phosphine oxide (501 mg, 0.79 mmol), triethylamine (3.9 mL, 31.6 mmol), trichlorosilane (0.80 mL, 7.9 mmol) and dry toluene (10 mL) were used. The reaction was finished after heating at 110° C. for 16 hours. The resulting residue was purified in the glove box by flash chromatography (diethyl ethyl/hexane 1:10), which afforded the desired compound (417 mg, 86%) as white foam. Single crystal of the phosphine was obtained by vapor diffusion of n-pentane into a concentrated solution in diethyl ether in a −30° C. fridge. $^1$H NMR (400 MHz, CDCl$_3$): δ 7.78-7.76 (m, 1H), 7.71 (d, J=8.4 Hz, 1H), 7.63-7.61 (m, 1H), 7.46-7.39 (m, 3H), 7.34 (d, J=7.8 Hz, 1H), 7.23 (d, J=9.1 Hz, 1H), 7.13 (d, J=7.8 Hz, 1H), 7.05 (d, J=8.4 Hz, 1H), 6.75 (d, J=8.4 Hz, 1H), 5.11 (d, J=12.8 Hz, 1H), 5.04 (d, J=12.8 Hz, 1H), 2.85-2.74 (m, 4H), 2.43-0.64 (m, 34H). $^{13}$C NMR (100 MHz, CDCl$_3$): δ 153.5, 145.6 (d, J$_{CP}$=31.0 Hz), 138.0, 136.4, 136.2 (d, J$_{CP}$=6.3 Hz), 135.7, 133.5, 132.9, 132.4 (d, J$_{CP}$=15.4 Hz), 129.85, 129.83, 129.76, 129.5, 129.0, 127.97, 127.92, 127.8, 126.2, 125.8, 125.0, 124.4, 108.7, 68.8, 35.5 (d, J$_{CP}$=15.5 Hz), 33.3 (d, J$_{CP}$=13.2 Hz), 30.6, 30.52, 30.48, 30.3, 30.0 (d, J$_{CP}$=9.3 Hz), 29.6, 29.5 (d, J$_{CP}$=12.7 Hz), 28.5 (d, J$_{CP}$=3.9 Hz), 27.9, 27.8 (d, J$_{CP}$=3.1 Hz), 27.5 (d, J$_{CP}$=5.7 Hz), 27.4 (d, J$_{CP}$=7.0 Hz), 26.8, 26.5, 23.8, 23.42, 23.37, 23.2. Some doublets due to C—P couplings in the aliphatic region cannot be assigned due to complexity of the spectrum and they are listed as singlets. $^{31}$P {1H} NMR (162 MHz, CDCl$_3$): δ −9.5. [a]$^{20}_D$=+19.2° (c=1.1, CH$_2$Cl$_2$). HRMS: Calcd for C$_{43}$H$_{52}$OP (M+H)$^+$: 615.38. Found: 615.45.

Synthesis of Ligands L7-8

The synthesis of chiral phosphines L7-8 is shown below in Scheme V.

SCHEME V

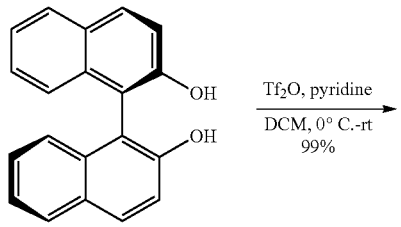

Tf$_2$O, pyridine
DCM, 0° C.-rt
99%

-continued

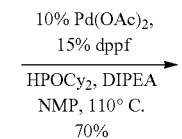

10% Pd(OAc)$_2$,
15% dppf
HPOCy$_2$, DIPEA
NMP, 110° C.
70%

3N NaOH
2:1 dioxane/methanol
rt, 16 h, 99%

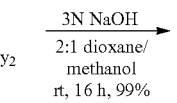

RBr, K$_2$CO$_3$
acetone,
reflux

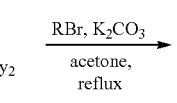

HSiCl$_3$, TEA
toluene, 110° C.

R = Bn 90%
R = CH$_2$(2-Naph) 93%

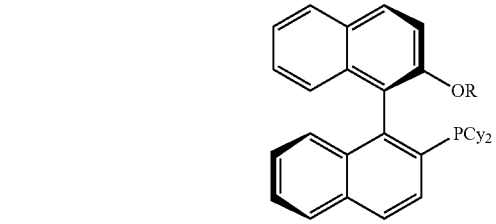

L7 R = Bn 80%
L8 R = CH$_2$(2-Naph) 82%

(R)-2,2'-Bis(trifluoromethanesulfonate)-1,1'-binaphthyl [126613-06-7]

Under argon, (R)-BINOL (5.73 g, 20 mmol) was dissolved in 100 mL of dry dichloromethane in a 250 mL Schlenk flask. Analytical-grade pyridine (4.2 mL, 52 mmol) was added and the solution was cooled to 0° C. Then triflic anhydride (7.4 mL, 44 mmol) was added slowly via a syringe over 5 min. The reaction mixture was allowed to warm up to 25° C. and kept stirred at 25° C. for 12 h. At the conclusion of the reaction, the mixture was passed through a pad of silica gel (~100 g) and washed with 1:30 ethyl acetate/hexane until no more product was eluted out (monitored by TLC). Concentration of the filtrate on a rotary evaporator gave the pure product (11.1 g, 95%) as white solid. $^1$H NMR (400 MHz, CDCl$_3$): δ 8.14 (d, J=9.2 Hz, 2H), 8.01 (d, J=8.4 Hz, 2H), 7.62 (d, J=9.2 Hz, 2H), 7.61-7.57 (m, 2H) 7.43-7.39 (m, 2H), 7.26 (d, J=8.4 Hz, 2H). $^{19}$F NMR (376 MHz, CDCl$_3$): δ −74.6.

(R)-2-(Dicyclohexylphosphinyl)-2'-trifluoromethanesulfonate-1,1'-binaphthyl

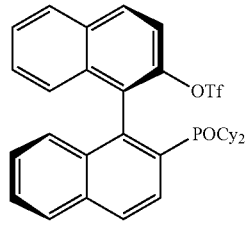

The procedure was a modification of a reported procedure. In an argon-filled glove box, Pd(OAc)$_2$ (131 mg, 0.58 mmol) and dppf (485 mg, 0.88 mmol) were added into a dry 100 mL Schlenk tube, followed by dry NMP (10 mL). After the resulting mixture was stirred at 25° C. for 30 minutes, a solution of (R)-2,2'-bis(trifluoromethane-sulfonyloxy)-1,1'-binaphthyl (3.0 g, 5.45 mmol) and dicyclohexylphosphine oxide (1.5 g, 7.0 mmol) in NMP (10 mL) was added, followed by N,N'-diisopropylethylamine (4.0 mL, 23.3 mmol) via a syringe in one portion. The resulting mixture was heated at 110° C. with stirring for 24 hours. At the end of the reaction, the mixture was cooled to 25° C. and NMP was removed under vacuum. The resulting residue was purified by flash chromatography (ethyl acetate/hexane 1:1 to 2:1) to give the target phosphine oxide (2.3 g, 70%) as off-white foam. $^1$H NMR (400 MHz, CDCl$_3$): δ 8.07-8.01 (m, 2H), 7.96-7.94 (m, 2H), 7.59-7.51 (m, 3H), 7.49-7.45 (m, 1H), 7.35-7.31 (m, 1H), 7.28-7.24 (m, 2H), 7.12 (d, J=8.4 Hz, 1H), 2.10-1.01 (m, 22H). $^{13}$C NMR (100 MHz, CDCl$_3$): δ 145.8, 138.8 (d, J$_{CP}$=3.4 Hz), 134.3, 134.2, 133.8 (d, J$_{CP}$=9.5 Hz), 132.2, 130.7, 129.4, 129.1 (d, J$_{CP}$=3.4 Hz), 128.8 (d, J$_{CP}$=22.3 Hz), 128.6, 128.2, 128.0, 127.57, 127.51, 127.2, 126.6, 126.5, 125.9 (d, J$_{CP}$=11.6 Hz), 119.5, 118.3 (q, J$_{CF}$=318.0 Hz), 38.6 (d, J$_{CP}$=66.2 Hz), 37.3 (d, J$_{CP}$=66.9 Hz), 26.9 (d, J$_{CP}$=4.4 Hz), 26.8-26.7 (3 overlapping signals), 26.8, 26.6, 26.5, 26.4, 26.0-25.8 (5 overlapping signals), 25.2 (d, J$_{CP}$=2.7 Hz). Some doublets due to C—P couplings in the aliphatic region cannot be assigned due to complexity of the spectrum and they are listed as singlets. $^{31}$P {1H} NMR (162 MHz, CDCl$_3$): δ 46.4. $^{19}$F NMR (376 MHz, CDCl$_3$): δ −75.2. ESI-MS: Calcd for C$_{33}$H$_{35}$F$_3$O$_4$PS (M+H)$^+$: 615.19. Found: 615.21.

(R)-2-(Dicyclohexylphosphinyl)-2'-hydroxy-1,1'-binaphthyl

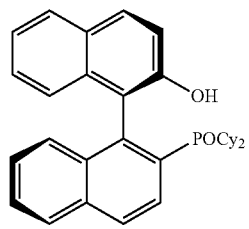

Under argon, (R)-2-(dicyclohexylphosphinyl)-2-(trifluoromethanesulfonyloxy)-1,1'-binaphthyl (3.5 g, 5.7 mmol) was dissolved in a 2:1 mixed solvent of dioxane/methanol (30 mL) in a 100 mL RBF. The solution was chilled to 0° C. and then 15 mL of 3.0 N aqueous NaOH solution was added. The resulting mixture was stirred at 25° C. for 12 hours. At the end of the reaction, the mixture was chilled to 0° C. and concentrated HCl (2.5 mL) was slowly added to adjust pH to ~3. After removal of organic solvents on a rotary evaporator, the residue was diluted with ethyl acetate (200 mL). The organic phase was washed with brine, dried over anhydrous MgSO$_4$ and finally concentrated under vacuum to afforded the title compound (2.75 g, 99%) as off-white solid. It was directly used in the next step without further purification. $^1$H NMR (400 MHz, CDCl$_3$): δ 8.33 (br s, 1H), 8.00 (d, J=8.4 Hz, 1H), 7.91-7.88 (m, 2H), 7.84 (d, J=8.0 Hz, 1H), 7.77 (pseudotriplet, J=8.8 Hz, 1H), 7.50 (pseudotriplet, J=7.6 Hz, 1H), 7.40 (d, J=8.8 Hz, 1H), 7.28-7.18 (m, 2H), 7.11-7.06 (m, 2H), 6.57 (d, J=8.4 Hz, 1H), 2.08-0.52 (m, 22H). $^{13}$C NMR (100 MHz, CDCl$_3$): δ 153.6, 140.9 (d, J$_{CP}$=6.0 Hz), 135.0, 134.8 (d, J$_{CP}$=2.0 Hz), 134.5 (d, J$_{CP}$=10.3 Hz), 130.3, 129.6 (d, J$_{CP}$=83.0 Hz), 129.5, 128.3, 128.1, 127.9, 127.8, 127.6, 127.3, 127.2, 126.3, 125.4, 123.4, 122.2, 121.9, 37.7 (d, J$_{CP}$=65.3 Hz), 35.8 (d, J$_{CP}$=66.5 Hz), 26.8, 26.7, 26.5-26.3 (3 overlapping signals), 26.07-25.99 (3 overlapping signals), 25.6. Some doublets due to C—P couplings in the aliphatic region cannot be assigned due to complexity of the spectrum and they are listed as singlets. $^{31}$P {1H} NMR (162 MHz, CDCl$_3$): δ 49.7. ESI-MS: Calcd for C$_{32}$H$_{36}$O$_2$P (M+H)$^+$: 483.25. Found: 483.40.

(R)-2-(Dicyclohexylphosphinyl)-2'-benzyloxy-1,1'-binaphthyl

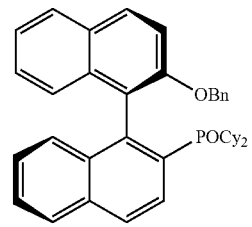

Under argon, to a 25 mL two-necked RBF equipped with a condenser was added (R)-2-(dicyclohexylphosphinyl)-2-hydroxy-binaphthyl (300 mg, 0.62 mmol) and anhydrous K$_2$CO$_3$ (350 mg, 2.5 mmol). Then analytical-grade acetone (12 mL) was added, followed by benzyl bromide (0.30 mL, 2.5 mmol). The resulting mixture was refluxed under argon for 2 days until all the starting material was consumed (monitored by $^{31}$P NMR spectroscopy). After the mixture was cooled to 25° C., it was filtered through a pad of CELITE® with ethyl acetate washings (15 mL×2). The filtrate was concentrated on a rotary evaporator and the resulting residue was purified by flash chromatography (ethyl acetate/hexane 2:1), which afforded the desired compound (320 mg, 90%) as white foam. $^1$H NMR (300 MHz, CDCl$_3$): δ 8.05-7.94 (m, 4H), 7.85 (d, J=8.1 Hz, 1H), 7.56-7.51 (m, 1H), 7.41 (d, J=9.0 Hz, 1H), 7.33-7.04 (m, 7H), 6.96 (d, J=8.4 Hz, 1H), 6.84-6.81 (m, 2H), 5.08 (d, J=13.2 Hz, 1H), 5.01 (d, J=13.2 Hz, 1H), 1.88-0.50 (m, 22H). $^{13}$C NMR (100 MHz, CDCl$_3$): δ 154.2, 140.2 (d, J$_{CP}$=6.4 Hz), 137.3, 134.8, 134.6 (d, J$_{CP}$=2.2 Hz), 133.8 (d, $J_{CP}$=10.5 Hz), 130.4 (d, $J_{CP}$=82.6 Hz), 130.1, 129.2, 128.4, 128.3, 128.2, 128.1, 127.6, 127.4, 127.2, 126.9, 126.7, 126.4, 126.0, 123.9, 122.6 (d, $J_{CP}$=3.3 Hz), 115.2, 71.0, 37.8 (d, $J_{CP}$=65.6 Hz), 37.6 (d, $J_{CP}$=65.8 Hz), 27.0, 26.8-26.6 (7 overlapping signals), 26.36-26.06 (6 overlapping signals), 26.0, 25.9. Some doublets due to C—P couplings cannot be assigned due to complexity of the spectrum and they are listed as singlets. $^{31}$P {1H} NMR (162 MHz, CDCl$_3$): δ 47.5 ESI-MS: Calcd for C$_{39}$H$_{42}$O$_2$P (M+H)$^+$: 573.29. Found: 573.43.

(R)-2-(Dicyclohexylphosphinyl)-2'-(2-naphthyl-methoxy)-1,1'-binaphthyl

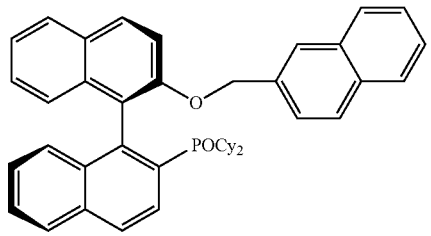

The same procedure as above was used. (R)-2-(Dicyclohexylphosphinyl)-2-hydroxy-1,1'-binaphthyl (150 mg, 0.31 mmol), 2-(bromomethyl)naphthalene (276 mg, 1.25 mmol), K$_2$CO$_3$ (173 mg, 1.25 mmol) and acetone (6 mL) were used. The reaction was finished after refluxing for 3 days. The crude product was purified by flash chromatography (ethyl acetate/hexane 1:1), which afforded the desired compound (179 mg, 93%) as white foam. $^1$H NMR (400 MHz, CDCl$_3$): δ 8.08-7.96 (m, 4H), 7.86 (d, J=8.0 Hz, 1H), 7.72-7.69 (m, 1H), 7.57-7.53 (m, 2H), 7.50-7.46 (m, 2H), 7.41-7.37 (m, 2H), 7.31 (pseudotriplet, J=7.6 Hz, 1H), 7.24-7.23 (m, 3H), 7.20-7.16 (m, 1H), 7.00 (d, J=8.4 Hz, 1H), 6.95 (dd, J=8.4, 1.2 Hz, 1H), 5.24 (d, J=12.8 Hz, 1H), 5.20 (d, J=12.8 Hz, 1H), 1.82-0.48 (m, 221-1). $^{13}$C NMR (100 MHz, CDCl$_3$): δ 154.1, 140.2 (d, $J_{CP}$=6.4 Hz), 134.73, 134.68, 134.6 (d, $J_{CP}$=2.0 Hz), 133.8 (d, $J_{CP}$=10.4 Hz), 133.2, 132.9, 130.4 (d, $J_{CP}$=81.6 Hz), 130.2, 129.2, 128.4 (d, $J_{CP}$=9.1 Hz), 128.2, 128.1, 127.93, 127.91, 127.7, 127.6, 127.3 (d, $J_{CP}$=10.5 Hz), 127.2, 126.7, 126.4, 126.1, 126.0, 125.9, 125.7, 124.8, 123.9, 122.5 (d, $J_{CP}$=3.3 Hz), 115.0, 70.9, 38.0 (d, $J_{CP}$=21.0 Hz), 37.4 (d, $J_{CP}$=21.4 Hz), 26.9, 26.8 (d, $J_{CP}$=5.3 Hz), 26.7-26.5 (6 overlapping signals), 26.27-25.96 (6 overlapping signals), 25.8. Some doublets due to C—P couplings in the aliphatic region cannot be assigned due to complexity of the spectrum and they are listed as singlets. $^{31}$P NMR (162 MHz, CDCl$_3$): δ 46.9 ESI-MS: Calcd for C$_{43}$H$_{44}$O$_2$P (M+H)$^+$: 623.31. Found: 623.40.

(R)-2-(Dicyclohexylphosphino)-2'-benzyloxy-1,1'-binaphthyl (L7)

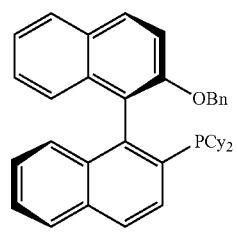

Under argon, a 25 mL Schlenk tube was charged with the corresponding phosphine oxide (138 mg, 0.24 mmol), triethylamine (1.3 mL, 9.6 mmol) and dry toluene (4.0 mL). After the resulting solution was cooled to 0° C., trichlorosilane (0.20 mL, 2.1 mmol) was added by syringe. The resulting mixture was heated with stirring in a 110° C. oil bath for 12 hours, until all the starting material was consumed (monitored by $^{31}$P NMR spectroscopy). At the conclusion of the reaction, the mixture was cooled to 25° C. in the glove box and diluted with degassed diethyl ether (10 mL). After the resulting suspension was briefly chilled for 5 minutes in a −30° C. fridge of the glove box, a degassed, saturated Na$_2$CO$_3$ solution (1.0 mL) was added to quench the reaction. The mixture was dried over MgSO$_4$, filtered through a pad of CELITE®, and washed with degassed diethyl ether until no more product was washed out (monitored by TLC). The filtrate was concentrated under vacuum, and the resulting residue was purified in the glove box by flash chromato-graphy (diethyl ethyl/hexane 1:10), which afforded the desired compound (107 mg, 80%) as white foam. $^1$H NMR (400 MHz, CDCl$_3$): δ 7.94-7.91 (m, 3H), 7.83 (d, J=8.4 Hz, 1H), 7.77 (dd, J=8.4, 1.2 Hz, 1H), 7.48-7.44 (m, 1H), 7.37 (d, J=9.2 Hz, 1H), 7.31-7.10 (m, 7H), 7.01 (d, J=8.4 Hz, 1H), 6.94-6.91 (m, 2H), 5.08-5.01 (m, 2H), 1.87-0.88 (m, 22H). $^{13}$C NMR (100 MHz, CDCl$_3$): δ 153.8 (d, $J_{CP}$=1.5 Hz), 143.6 (d, $J_{CP}$=32.0 Hz), 137.8, 135.6, 135.5, 134.6 (d, $J_{CP}$=2.1 Hz), 133.8, 133.6 (d, $J_{CP}$=7.2 Hz), 129.7, 129.4 (d, $J_{CP}$=2.8 Hz), 129.0, 128.29, 128.09, 127.95, 127.37, 127.2 (d, $J_{CP}$=2.1 Hz), 126.9, 126.5, 126.4, 126.08, 126.02, 123.9 (d, $J_{CP}$=8.4 Hz), 123.7, 114.5, 70.3, 35.5 (d, $J_{CP}$=14.9 Hz), 34.7 (d, $J_{CP}$=14.2 Hz), 30.8 (d, $J_{CP}$=7.0 Hz), 30.64-30.57 (3 overlapping signals), 30.3 (d, $J_{CP}$=11.2 Hz), 30.1 (d, $J_{CP}$=9.6 Hz), 29.9, 27.7-27.5 (5 overlapping signals), 27.4, 26.6. Some doublets due to C—P couplings in the aliphatic region cannot be assigned due to complexity of the spectrum and they are listed as singlets. $^{31}$P {1H} NMR (121 MHz, CDCl$_3$): δ −9.0. [α]$^{20}_D$=+67.9° (c=0.8, CH$_2$Cl$_2$). HRMS: Calcd for C$_{39}$H$_{42}$OP (M+H)$^+$: 557.30. Found: 557.39.

(R)-2-(Dicyclohexylphosphino)-2'-(2-naphthyl-methoxy)-1,1'-binaphthyl

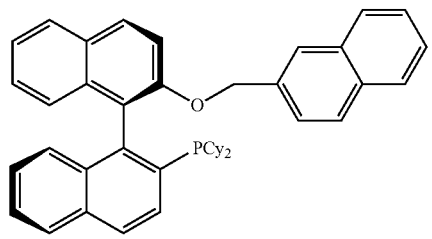

The same procedure as described above was used. The corresponding phosphine oxide (150 mg, 0.24 mmol), triethylamine (1.3 mL, 9.6 mmol), trichlorosilane (0.20 mL, 2.4 mmol) and dry toluene (4 mL) were used. The reaction was finished after heating at 110° C. for 16 hours. The resulting residue was purified in the glove box by flash chromatography (diethyl ethyl/hexane 1:10), which afforded the desired compound (119 mg, 82%) as white foam. $^1$H NMR (400 MHz, CDCl$_3$): δ 7.97-7.90 (m, 3H), 7.84 (d, J=8.4 Hz, 1H), 7.79 (dd, J=8.8, 1.2 Hz, 1H), 7.74-7.70 (m, 1H), 7.60 (d, J=8.8 Hz, 1H), 7.54-7.46 (m, 2H), 7.42-7.37 (m, 3H), 7.31-7.24 (m, 4H), 7.23-7.17 (m, 1H), 7.06-7.04

(m, 2H), 5.23 (d, J=13.0 Hz, 1H), 5.18 (d, J=13.0 Hz, 1H), 1.90-0.80 (m, 22H). $^{13}$C NMR (75 MHz, CDCl$_3$): δ 153.7, 143.6 (d, $J_{CP}$=32.0 Hz), 135.7, 135.5, 135.2, 134.6 (d, $J_{CP}$=2.2 Hz), 133.9, 133.7, 133.6, 133.4, 132.9, 129.8, 129.4 (d, $J_{CP}$=2.8 Hz), 129.0, 128.1, 127.99, 127.95, 127.8, 127.2 (d, $J_{CP}$=2.1 Hz), 126.9, 126.54, 126.48, 126.2, 126.1 (2 overlapping signals), 125.8, 125.3, 124.6, 124.0 (d, $J_{CP}$=8.2 Hz), 123.7, 114.4, 70.2, 35.5 (d, $J_{CP}$=15.0 Hz), 34.8 (d, $J_{CP}$=14.3 Hz), 30.8 (d, $J_{CP}$=5.9 Hz), 30.6 (d, $J_{CP}$=5.3 Hz), 30.3 (d, $J_{CP}$=12.2 Hz), 30.1 (d, $J_{CP}$=9.6 Hz), 27.7-27.5 (5 overlapping signals), 27.4, 26.6 (d, $J_{CP}$=6.2 Hz). Some doublets due to C—P couplings in the aliphatic region cannot be assigned due to complexity of the spectrum and they are listed as singlets. $^{31}$P {1H} NMR (162 MHz, CDCl$_3$): δ −8.9. [a]$^{20}_D$=+29.1° (c=1.1, CH$_2$Cl$_2$). HRMS: Calcd for C$_{43}$H$_{44}$OP (M+H)$^+$: 607.32. Found: 607.36.

III. Synthesis of Aryl and Heteroaryl Triflates.

General Procedure: Under argon, a 100 mL Schlenk flask was charged successively with phenol (10.0 mmol), dry dichloromethane (30 mL) and analytical-grade pyridine (1.2 mL, 15.0 mmol). The solution was cooled to 0° C. in an ice bath, and treated with dropwise addition of triflic anhydride (2.0 mL, 12.0 mmol). The resulting mixture was slowly warmed up to 25° C. and kept stirred for additional 5 hours. At the end of the reaction (monitored by TLC), the mixture was passed through a pad of silica gel (~80 g) with 1:30 Ethyl acetate/hexane washings, until no more aryl triflate was eluted out. The filtrate was concentrated on a rotary evaporator and the residue was subjected to flash silica gel chromatography to afford the desired aryl triflate.

1-Naphthyl trifluoromethanesulfonate [99747-74-7]

Flash chromatography (60:1 hexane/EtOAc) yielded the target compound as colorless oil (95%). $^1$H NMR (300 MHz, CDCl$_3$): δ 8.09 (d, J=8.3 Hz, 1H), 7.94-7.85 (m, 2H), 7.69-7.58 (m, 2H), 7.53-7.46 (m, 2H).

2-Naphthyl trifluoromethanesulfonate [3857-83-8]

Flash chromatography (50:1 hexane/EtOAc) yielded the target compound as white solid (96%). $^1$H NMR (400 MHz, CDCl$_3$): δ 7.94-7.87 (m, 3H), 7.76 (d, J=2.4 Hz, 1H), 7.61-7.55 (m, 2H), 7.38 (dd, J=9.0, 2.4 Hz, 1H).

6-Methoxyl-2-naphthyl trifluoromethanesulfonate [129731-74-4]

Flash chromatography (40:1 hexane/EtOAc) yielded the target compound as white solid (98%). $^1$H NMR (400 MHz, CDCl$_3$): δ 7.79 (d, J=9.0 Hz, 1H), 7.75 (d, J=9.0 Hz, 1H), 7.66 (d, J=2.4 Hz, 1H), 7.33 (dd, J=9.0, 2.4 Hz, 1H), 7.23 (dd, J=9.0, 2.4 Hz, 1H), 7.16 (d, J=2.4 Hz, 1H), 3.93 (s, 3H).

3-Benzoylphenyl trifluoromethanesulfonate [209917-31-7]

Flash chromatography (30:1 hexane/EtOAc) yielded the target compound as white solid (93%). $^1$H NMR (400 MHz, CDCl$_3$): δ 7.85-7.79 (m, 3H), 7.71 (pseudotriplet, J=1.7 Hz, 1H), 7.66-7.58 (m, 2H), 7.54-7.50 (m, 3H).

Phenyl trifluoromethanesulfonate [17763-67-6]

Flash chromatography (40:1 pentane/diethyl ether) yielded the target compound as colorless oil (90%). $^1$H NMR (400 MHz, CDCl$_3$): δ 7.49-7.43 (m, 2H), 7.41-7.37 (m, 1H), 7.29-7.26 (m, 2H).

o-Anisyl trifluoromethanesulfonate [59099-58-0]

Flash chromatography (40:1 pentane/diethyl ether) yielded the target compound as colorless oil (95%). $^1$H NMR (400 MHz, CDCl$_3$): δ 7.33 (ddd, J=8.4, 8.0, 1.6 Hz, 1H), 7.22 (dd, J=8.0, 1.6 Hz, 1H), 7.04 (dd, J=8.4, 1.4 Hz, 1H), 6.98 (pseudotriplet of doublet, J=8.0, 1.4 Hz, 1H), 3.92 (s, 3H).

o-Tolyl trifluoromethanesulfonate [66107-34-4]

Flash chromatography (30:1 pentane/diethyl ether) yielded the target compound as colorless oil (95%). $^1$H NMR (400 MHz, CDCl$_3$): δ 7.32-7.23 (m, 4H), 2.39 (s, 3H).

2-Cynaophenyl trifluoromethanesulfonate [138313-23-2]

Flash chromatography (30:1 hexane/EtOAc) yielded the target compound as colorless oil (97%). $^1$H NMR (400 MHz, CDCl$_3$): δ 7.78 (dd, J=7.8, 1.6 Hz, 1H), 7.76-7.72 (m, 1H), 7.54 (dd, J=7.6, 1.6 Hz, 1H), 7.52-7.50 (m, 1H).

2-Nitrophenyl trifluoromethanesulfonate [132993-22-7]

Flash chromatography (30:1 hexane/EtOAc) yielded the target compound as yellow oil (97%). $^1$H NMR (400 MHz, CDCl$_3$): δ 8.18 (dd, J=8.2, 1.6 Hz, 114), 7.76 (pseudotriplet of doublet, J=7.8, 1.6 Hz, 1H), 7.59 (ddd, J=8.2, 7.8, 1.6 Hz, 1H), 7.48 (dd, J=8.2, 1.2 Hz, 1H).

4-(Ethoxycarbonyl)phenyl trifluoromethanesulfonate [125261-30-5]

Flash chromatography (30:1 hexane/EtOAc) yielded the target compound as colorless oil (93%). $^1$H NMR (400 MHz, CDCl$_3$): δ 8.17-8.13 (m, 2H), 7.37-7.33 (m, 2H), 4.40 (q, J=7.1 Hz, 2H), 1.40 (t, J=7.1 Hz, 3H).

2-(Methoxycarbonyl)thiophene-3-trifluoromethanesulfonate [313697-13-1]

Flash chromatography (30:1 hexane/EtOAc) yielded the target compound as colorless oil (93%). $^1$H NMR (400 MHz, CDCl$_3$): δ 7.55 (d, J=5.5 Hz, 1H), 7.01 (d, J=5.5 Hz, 1H), 3.93 (s, 3H).

2-Methyl-8-quinolinyl trifluoromethanesulfonate [256652-07-0]

Flash chromatography (30:1 hexane/EtOAc) yielded the target compound as yellowish solid (98%). $^1$H NMR (400 MHz, CDCl$_3$): δ 8.08 (d, J=8.4 Hz, 1H), 7.79 (dd, J=8.2, 1.1 Hz, 1H), 7.57 (dd, J=7.7, 1.1 Hz, 1H), 7.48 (dd, J=8.2, 7.7 Hz, 1H), 7.39 (d, J=8.4 Hz, 1H), 2.80 (s, 3H).

IV. Synthesis of Silyl Ketene Acetals.

(1E)-1-Methoxy-1-(trimethylsiloxy)propene [72658-09-4]

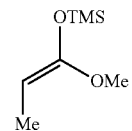

The compound was prepared according to a reported procedure. Under argon, a 2.0 M n-BuLi solution in cyclohexane (62.5 mL, 125.0 mmol) in an addition funnel was slowly added to a stirred solution of i-Pr$_2$NH (19.1 mL, 136.3 mmol) in dry THF (200 mL) at 0° C. over 20 min. The mixture was stirred at 0° C. for 30 minutes and then it was cooled to −78° C. in a cooling bath. A solution of methyl propionate (10.0 g, 113.6 mmol) and TMSCl (17.2 mL, 136.3 mmol) in dry THF (100 mL) was added slowly over 1.5 hours from the addition funnel. After stirring at −78° C. for additional 30 minutes, the mixture was slowly warmed up to 25° C. and kept stirred for 12 hours. At the end of the reaction, most of THF was removed by distillation under one atmosphere of argon. The residue was diluted with 200 mL of pentane and the resulting suspension was filtered through a fritted funnel (medium porosity) with pentane washings, to remove LiCl. The filtrate was concentrated and the crude product was purified by distillation under vacuum (49° C. at 20 mbar), which afforded the desired silyl ketene acetal as colorless oil (10.9 g, 60% yield). The E/Z ratio of the purified product was determined to be 8:1 by $^1$H NMR spectroscopy. $^1$H NMR (300 MHz, C$_6$D$_6$): o 3.82 (q, J=6.6 Hz, 1H), 3.36 (s, 3H), 1.73 (d, J=6.6 Hz, 3H), 0.13 (s, 9H).

(1E)-1-Ethoxy-1-(trimethylsiloxy)propene
[73967-97-2]

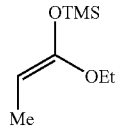

The same procedure as (1E)-1-methoxy-1-(trimethylsiloxy)propene was used. Reaction scale: ethyl propionate (4.0 g, 39.2 mmol). The product was purified by bulb-to-bulb distillation (70° C. at 5 mbar), which afforded the desired silyl ketene acetal as colorless oil (5.5 g, 82% yield). The E/Z ratio of the purified product was determined to be 9:1 by $^1$H NMR spectroscopy. $^1$H NMR (300 MHz, CDCl$_3$): δ 3.83 (q, J=7.2 Hz, 2H), 3.73 (q, J=6.6 Hz, 1H), 1.50 (d, J=6.6 Hz, 3H), 1.23 (t, J=7.2 Hz, 3H), 0.21 (s, 9H).

(1E)-1-Cyclohexoxy-1-(trimethylsiloxy)propene
[1239020-67-7]

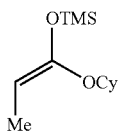

Under argon, a 2.0 M n-BuLi solution in cyclohexane (4.5 mL, 9.0 mmol) was slowly added to a stirred solution of i-Pr$_2$NH (1.32 mL, 9.4 mmol) in dry THF (10 mL) at 0° C. The mixture was stirred at 0° C. for 30 minutes. After the LDA solution was cooled to −78° C. in a dry ice/acetone bath, a solution of cyclohexyl propionate (1.3 g, 8.5 mmol) in dry THF (2.0 mL) was slowly added over 5 minutes. After stirring at −78° C. for 30 minutes, TMSCl (1.3 mL, 10.2 mmol) was added over 1 minute. After stirring for additional 2 hours at −78° C., the mixture was warmed up to 25° C. and poured into a mixture of ice water and hexane. The organic layer was separated and the aqueous layer was extracted with hexane (10 mL×2). The combined organic layer was washed with brine, dried over anhydrous Na$_2$SO$_4$ and concentrated on a rotary evaporator. The crude product was purified by bulb-to-bulb distillation (110° C. at 19 mbar), which afforded the desired silyl ketene acetal as colorless oil (1.58 g, 82% yield). The E/Z ratio of the purified product was determined to be 9:1 by $^1$H NMR spectroscopy. $^1$H NMR (300 MHz, C$_6$D$_6$): o 4.23-4.15 (m, 1H), 3.96 (q, J=6.6 Hz, 1H), 1.84-1.08 (m, 13H), 0.18 (s, 9H).

(1E)-1-(2'-Naphthyloxy)-1-(trimethylsiloxy)propene
[1239020-67-7]

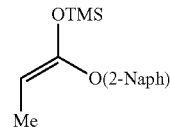

The same procedure as (1E)-1-cyclohexoxy-1-(trimethylsiloxy)propene was used. Reaction scale: 2-naphthyl propionate (2.0 g, 10.0 mmol). The product was purified by bulb-to-bulb distillation (90° C. at 250 mTorr), which afforded the desired silyl ketene acetal as colorless oil (2.2 g, 80% yield). The E/Z ratio of the purified product was determined to be 25:1 by $^1$H NMR spectroscopy. $^1$H NMR (300 MHz, C$_6$D$_6$): o 7.57-7.51 (m, 4H), 7.30 (dd, J=9.0, 2.4 Hz, 1H), 7.23-7.12 (m, 2H), 4.46 (q, J=6.8 Hz, 1H), 1.61 (d, J=6.8 Hz, 3H), 0.10 (s, 9H).

(1E)-1-tert-Butoxy-1-(trimethylsiloxy)propene
[72658-10-7]

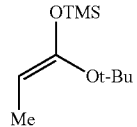

The compound was prepared according to a reported procedure. Under argon, a 2.0 M n-BuLi solution in cyclohexane (44.0 mL, 88.0 mmol) was slowly added to a stirred solution of i-Pr$_2$NH (13.5 mL, 96.0 mmol) in dry cyclopentyl methyl ether (60 mL) at 0° C. After stirring at 0° C. for 30 minutes, the solution was treated with slow addition of a solution of tert-butyl propionate (10.4 g, 80.0 mmol) in dry cyclopentyl methyl ether (20 mL) from an addition funnel over 20 minutes. After stirring at 0° C. for 30 minutes, TMSCl (12.2 mL, 96.0 mmol) was added over 5 minutes. After stirring at 0° C. for additional 2.5 h, the reaction mixture was poured into a mixture of ice water and hexane. The organic layer was separated and the aqueous layer was extracted with hexane (30 mL×2). The combined organic layer was washed with brine, dried over anhydrous Na$_2$SO$_4$ and concentrated on a rotary evaporator. The crude product was purified by bulb-to-bulb distillation (60° C. at 16 mbar), which afforded the desired silyl ketene acetal as colorless oil (11.3 g, 70% yield). The E/Z ratio of the purified product was determined to be 99:1 by $^1$H NMR spectroscopy. $^1$H NMR (400 MHz, CDCl$_3$): δ 3.90 (q, J=6.6 Hz, 1H), 1.49 (d, J=6.6 Hz, 3H), 1.32 (s, 9H), 0.20 (s, 9H). $^1$H NMR (400

MHz, C₆D₆): o 4.05 (q, J=6.6 Hz, 1H), 1.66 (d, J=6.6 Hz, 3H), 1.33 (s, 9H), 0.17 (s, 9H).

(1E)-1-tert-Butoxy-1-(trimethylsiloxy)butene

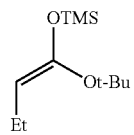

The same procedure as (1E)-1-tert-butoxy-1-(trimethylsiloxy)propene was used. Reaction scale: tert-butyl butanoate (0.86 g, 6.0 mmol). The crude product was purified by bulb-to-bulb distillation (90° C. at 11 mbar), which afforded the desired silyl ketene acetal as colorless oil (0.87 g, 67% yield). The E/Z ratio of the purified product was determined to be 99:1 by $^1$H NMR spectroscopy. $^1$H NMR (CDCl₃, 400 MHz): o 3.85 (t, J=7.1 Hz, 1H), 1.96 (tt, J=7.4, 7.1 Hz, 2H), 1.31 (s, 9H), 0.91 (t, J=7.4 Hz, 3H), 0.20 (s, 9H). $^{13}$C. NMR (100 MHz, CDCl₃): δ 151.2, 93.8, 78.1, 29.3, 19.2, 15.3, 0.11. GCMS (EI): calcd for $C_{11}H_{24}O_2Si$ M: 216.15. Found: 216.11.

(1E)-1-tert-Butoxy-1-(trimethylsiloxy)dodecene

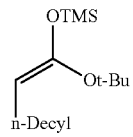

The same procedure as (1E)-1-tert-butoxy-1-(trimethylsiloxy)propene was used. Tert-Butyl dodecanoate (1.28 g, 5.0 mmol) and TMSCl (0.9 mL, 7.0 mmol) were used. The crude product was purified by bulb-to-bulb distillation (90° C. at 70 mTorr), which afforded the desired silyl ketene acetal as colorless oil (1.44 g, 88% yield). The E/Z ratio of the purified product was determined to be 99:1 by $^1$H NMR spectroscopy. The compound is unstable under GCMS and ESI conditions. $^1$H NMR (400 MHz, CDCl₃): δ 3.85 (t, J=7.2 Hz, 1H), 1.94-1.90 (m, 2H), 1.31 (s, 9H), 1.26 (br s, 16H), 0.88 (t, J=6.6 Hz, 3H), 0.21 (s, 9H). $^{13}$C NMR (100 MHz, CDCl₃): δ 151.6, 92.0, 78.1, 32.2, 30.7, 29.92, 29.89, 29.8, 29.6 (2 overlapping signals), 29.3, 25.8, 22.9, 14.4, 0.13.

(E)-1-tert-Butoxy-1-(trimethylsiloxy)-3-phenylpropene

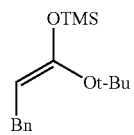

The same procedure as (1E)-1-tert-butoxy-1-(trimethylsiloxy)propene was used. Reaction scale: tert-butyl 1-phenyl propionate (1.09 g, 5.0 mmol). The product was purified by bulb-to-bulb distillation (80° C. at 180 mTorr), which afforded the desired silyl ketene acetal as colorless oil (1.21 g, 87% yield), as a 2.1:1 mixture of both O- and C-silylated enolates (based on H NMR spectroscopy). The E/Z ratio of the O-silylated product was determined to be 18:1 by $^1$H NMR spectroscopy. $^1$H NMR of (E)-O-TMS enolate (400 MHz, CDCl₃): δ 7.28-7.13 (m, 5H), 4.05 (t, J=7.2 Hz, 1H), 3.56 (d, J=7.2 Hz, 2H), 1.34 (s, 9H), 0.23 (s, 9H).

(1Z)-1-tert-Butoxy-1-(trimethylsiloxy)propene [72658-04-9]

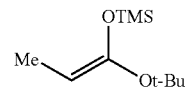

The procedure was based on a modification of a reported procedure. Under argon, a 2.0 M n-BuLi solution in cyclohexane (2.3 mL, 4.6 mmol) was slowly added to a stirred solution of i-Pr₂NH (0.65 mL, 4.7 mmol) in dry THF (4 mL) maintained at 0° C. After stirring at 0° C. for 30 min, the LDA solution was cooled to -78° C. in a dry ice/acetone bath, dry HMPA (1.5 mL) was added dropwise over 1 min. After stirring at -78° C. for 5 min, a solution of tert-butyl propionate (1.0 mL, 6.7 mmol) in a mixed solvent of HMPA (1.5 mL) and dry THF (5.0 mL) was added dropwise over 5 min. After stirring for 15 min, a solution of TMSCl (0.68 mL, 5.4 mmol) in a mixed solvent of HMPA (1.5 mL) and dry hexane (3.5 mL) was added over 5 min. After the addition, the mixture was stirred at -78° C. for 5 min. Then the cooling bath was removed, and the resulting mixture was allowed to warm up to 25° C. and kept stirred at 25° C. for 1 hour. At the conclusion of the reaction, the mixture was quenched with a saturated NaHCO₃ solution (5 mL), and then diluted with pentane (60 mL). The organic layer was successively washed with cold water (3×10 mL) and brine (10 mL), dried over MgSO₄ and concentrated on a rotary evaporator. The resulting residue was purified by bulb-to-bulb distillation (80° C. at 28 mbar), which afforded the title compound as colorless oil (400 mg, 44% yield), as a 1:0.9 mixture of both O- and C-silylated enolates (based on H NMR spectroscopy). The E/Z ratio of the O-TMS product was determined to be 1:33 by $^1$H NMR spectroscopy. $^1$H NMR of (Z)—O-TMS enolate (300 MHz, C₆D₆): o 4.14 (q, J=6.6 Hz, 1H), 1.63 (d, J=6.6 Hz, 3H), 1.25 (s, 9H), 0.24 (s, 9H).

tert-Butyl 2-(trimethylsilyl)propionate

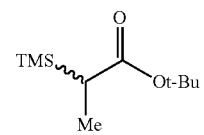 [SMILES: CC(C(=O)OC(C)(C)C)[Si](C)(C)C]

A similar procedure as above was followed and tert-butyl propionate (2.0 mL, 13.4 mmol) was used. After the workup and before distillation, the crude product was dissolved in 5 mL of analytical grade dichloromethane and stirred with silica gel (Merck, 600 mg) at 25° C. for 30 min to selectively hydrolyze the O-TMS enolate. Then silica gel was filtered off with dichloromethane washings (5 mL). The filtrate was concentrated on a rotary evaporator. The resulting residue was purified by bulb-to-bulb distillation (20 mbar at 80° C.), which afforded the title compound as colorless oil (372 mg, 20% yield). $^1$H NMR (400 MHz, CDCl$_3$): δ 1.93 (q, J=7.2 Hz, 1H), 1.43 (s, 9H), 1.11 (d, J=7.2 Hz, 3H), 0.07 (s, 9H). $^{13}$C NMR (100 MHz, CDCl$_3$): δ 175.8, 79.5, 31.2, 28.5, 11.2, −2.6. GCMS (EI): calcd for C$_{10}$H$_{23}$O$_2$Si (M+H)$^+$: 203.15. Found: 202.97.

(1E)-1-tert-Butoxy-1-(tert-butyldimethylsiloxy)propene [89043-58-3]

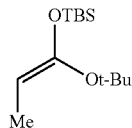

The compound was prepared according to a reported procedure. Under argon, a 2.0 M n-BuLi solution in cyclohexane (3.7 mL, 7.4 mmol) was slowly added to a stirred solution of i-Pr$_2$NH (1.1 mL, 7.4 mmol) in dry THF (10 mL) at 0° C. After stirring at 0° C. for 30 minutes, the LDA solution was cooled to −78° C. in a dry-ice/acetone bath, and treated with slow addition of a solution of tert-butyl propionate (1.0 mL, 6.7 mmol) in dry THF (1 mL) over 3 minutes. After stirring at −78° C. for additional 30 minutes, a solution of TBSCl (1.1 g, 7.4 mmol) in 1:1 THF/HMPA (6 mL) was added over 5 minutes. After the addition, the mixture was stirred at −78° C. for 5 minutes, warmed up to 25° C. and then stirred at 25° C. for 1 hour. The reaction mixture was diluted with pentane (20 mL) and washed with cold water (3×10 mL) and brine (10 mL) successively. The organic layer was dried over MgSO$_4$ and concentrated on a rotary evaporator. The resulting residue was purified by bulb-to-bulb distillation (100° C. at 3 mbar), which afforded the title compound as colorless oil (1.4 g, 90% yield). The E/Z ratio of the purified product was determined to be 13:1 by $^1$H NMR spectroscopy. $^1$H NMR (300 MHz, C$_6$D$_6$): o 4.11 (q, J=6.6 Hz, 1H), 1.64 (d, J=6.6 Hz, 3H), 1.33 (s, 9H), 0.98 (s, 9H), 0.17 (s, 6H).

Typical procedure for the asymmetric arylation of silyl ketene acetals using PdMe$_2$(TMEDA)

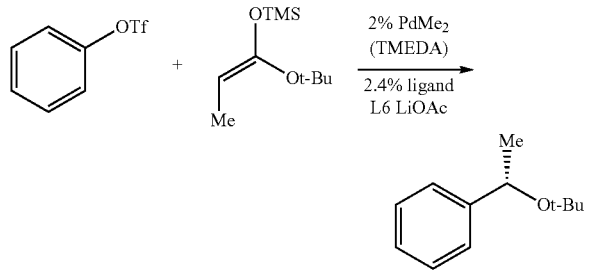

Synthesis of (S)-tell-butyl 2-phenylpropionate [59415-37-1]. In an argon-filled glove box, a dry 4 mL vial was charged with PdMe$_2$(TMEDA) (2.5 mg, 0.010 mmol), (R)-2-(dicyclohexylphosphino)-2'-(2-naphthylmethoxy)-5,5',6,6',7,7',8,8'-octahydro-1,1'-binaphthyl L6 (7.4 mg, 0.012 mmol) and 1.0 mL of dry α,α,α-trifluorotoluene. After stirring at 25° C. for 30 minutes, the mixture was treated successively with anhydrous LiOAc (66 mg, 1.0 mmol), phenyl trifluoromethanesulfonate (113 mg, 0.50 mmol), (1E)-1-tert-butoxy-1-(trimethylsiloxy)propene (152 mg, 0.75 mmol) and GC standard n-dodecane (50 μL). The vial was capped tightly and the mixture was heated with stirring in a 50° C. (internal temperature) heating block. After aryl triflate was fully consumed within 18 hours at 50° C. (monitored by OC and TLC), the reaction mixture was cooled to 25° C. and filtered through a pad of silica gel with diethyl ether washings (20 mL), The filtrate was concentrated and the residue was purified by flash silica gel chromatography with ethyl acetate/hexane (1:40) as eluent to give the title compound as colorless oil (96 mg, 93% yield).

The ee of the purified products was determined to be 90% based on chiral HPLC analysis (Deicel CHIRALCEL OJ-H; hexanes: i-PrOH=99.5:0.5; detection wavelengths=254 nm and 227 nm; flow rate=0.5 mL/min). T$_R$=17.0 min (minor) and 18.7 min (major). [α]$^{20}$$_D$=+24.3° (c=3.3, CHCl$_3$). $^1$H NMR (400 MHz, CDCl$_3$): δ 7.33-7.21 (m, 5H), 3.61 (q, I=7.1, 1H), 1.45 (d, J=7.1 Hz, 3H), 1.39 (s, 9H). $^{13}$C NMR (100 MHz, CDCl$_3$): δ 174.1, 141.4, 128.7, 127.6, 127.0, 80.7, 46.7, 28.2, 18.8. OCMS (EI): calcd for C$_{13}$H$_{16}$O$_2$ M: 206.13. Found: 205.96.

Typical procedure of the asymmetric arylation of silyl ketene acetals using Pd(dba)$_2$

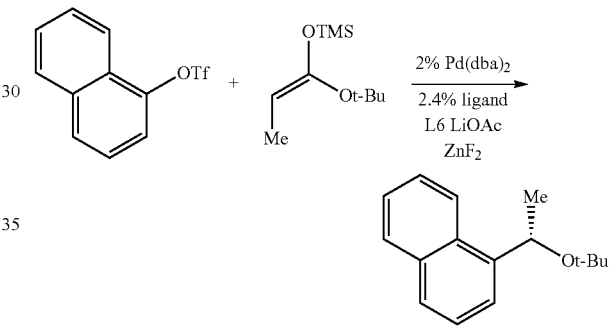

Synthesis of (S)-tert-butyl 2-(1'-naphthyl)propionate. In an argon-filled glove box, a dry 4 mL vial was charged with Pd(dba)$_2$ (5.8 mg, 0.010 mmol), (R)-2-(dicyclohexylphosphino)-2'-(2-naphthylmethoxy)-5,5',6,6',7,7',8,8'-octahydro-1,1'-binaphthyl L6 (7.4 mg, 0.012 mmol) and 1.0 mL of dry α,α,α-trifluorotoluene. After stirring at 25° C. for 30 minutes, the mixture was treated successively with anhydrous LiOAc (66 mg, 1.0 mmol), ZnF$_2$ co-activator (10 mg, 0.10 mmol), 1-naphthyl trifluoromethanesulfonate (138 mg, 0.50 mmol), (1E)-1-tert-butoxy-1-(trimethylsiloxy)propene (152 mg, 0.75 mmol) and GC standard n-dodecane (50 uL). The vial was capped tightly and the mixture was heated with stirring in a 50° C. (internal temperature) heating block. After aryl triflate was fully consumed within 24 hours at 50° C. (monitored by GC and TLC), the reaction mixture was cooled to 25° C. and filtered through a pad of silica gel with diethyl ether washings (20 mL). The filtrate was concentrated and the residue was purified by flash silica gel chromatography with ethyl acetate/hexane (1:50) as eluent to give the title compound as colorless oil (127 mg, 99% yield). The ee of the purified products was determined to be 92% by chiral HPLC analysis (Daicel CHIRALCEL OJ-H; hexanes: i-PrOH=98:2; detection wavelengths=254 nm and 227 nm; flow rate=0.5 mL/min). T$_R$=13.2 min (major) and 15.8 min (minor). [α]$^{20}$$_D$=+95.5° (c=2.2, CHCl$_3$). $^1$H NMR (400 MHz, CDCl3): δ 8.11 (d, J=8.4 Hz, 1H), 7.87 (dd, J=7.8, 1.8 Hz, 1H), 7.78-7.75 (m, 1H), 7.56-7.42 (m, 4H), 4.42 (q, J=7.2 Hz, 1H), 1.61 (d, J=7.2 Hz, 3H), 1.42 (s, 9H). $^{13}$C NMR (100 MHz, CDCl3): δ 174.4, 137.7, 134.2, 131.7, 129.1, 127.6, 126.2, 125.77, 125.69, 124.4, 123.6, 80.9, 42.5, 28.1, 18.3. GCMS (EI): calcd for $C_{17}H_{20}O_2$ M: 256.15. Found: 256.07.

VI Condition Optimization of Asymmetric Arylation (Table III and IV).

Typical procedure: In an argon-filled glove box, a dry 4 mL vial was charged with PdMe$_2$ (TMEDA) (0.5 mg, 0.002 mmol), ligand L6 (1.5 mg, 0.0024 mmol) and 0.2 mL of dry α,α,α-trifluorotoluene. After stirring at 25° C. for 30 minutes, the mixture was treated successively with anhydrous lithium acetate (13 mg, 0.20 mmol), 1-naphthyl trifluoromethanesulfonate (28 mg, 0.10 mmol), (1E)-1-tert-butoxy-1-(trimethylsiloxy)propene (30 mg, 0.15 mmol) and n-dodecane (10 uL). The vial was capped tightly and the mixture was heated with stirring in a 50° C. (internal temperature) aluminum heating block for 6 h, until aryl triflate was fully consumed. At intervals, an aliquot of the reaction mixture was taken inside the glove box and passed through a silica gel plug with diethyl ether washing (1.5 mL). The filtrate was used to determine the GC conversion of aryl triflate. At the end of the reaction, some crude sample was loaded onto a silica gel plug and eluted with 1.5 mL of 9:1 hexane/isopropanol mixed solvent for chiral HPLC analysis of ee.

For determination of GC yield and ee of the enantioenriched product, the racemic coupling product was prepared using a similar procedure with SPhos as ligand instead of L6.

TABLE III

Effect of Solvents

| Entry | Solvent | Time (h) | Conv (%) | GC Yield (%) | EE (%) |
|---|---|---|---|---|---|
| 1 | PhCF$_3$ | 3 h | 95 | 94 | 90 |
|   |   | 6 h | 100 | 99 | 90 |
| 2 | Toluene | 3 h | 88 | 82 |   |
|   |   | 6 h | 100 | 98 | 83 |
| 3 | PhCl | 3 h | 50 | 37 |   |
|   |   | 6 h | 60 | 48 |   |
|   |   | 24 h | 65 | 55 | 88 |
| 4 | PhF | 3 h | 99 | 86 |   |
|   |   | 6 h | 100 | 90 | 89 |
| 5 | Benzene | 3 h | 91 | 77 |   |
|   |   | 6 h | 100 | 89 | 83 |
| 6 | DCM | 3 h | 14 | 3 |   |
|   |   | 6 h | 20 | 9 |   |
|   |   | 24 h | 52 | 40 | 85 |
| 7 | DCE | 3 h | 17 | 6 |   |
|   |   | 6 h | 32 | 20 |   |
|   |   | 24 h | 83 | 72 | 83 |
| 8 | THF | 3 h | 19 | 7 |   |
|   |   | 6 h | 33 | 19 |   |
|   |   | 24 h | 80 | 70 | 86 |

TABLE IV

Effect of Activators

| Entry | Activator | Time (h) | Conv (%) | GC yield (%) | EE (%) |
|---|---|---|---|---|---|
| 1 | LiOAc | 3 h | 95 | 94 | 90 |
|   |   | 6 h | 100 | 99 | 90 |
| 2 | LiTFA | 3 h | 4 | 3 |   |
|   |   | 6 h | 12 | 7 |   |
|   |   | 24 h | 43 | 35 | 90 |
| 3 | LiOTf | 3 h | 1 | 1 |   |
|   |   | 6 h | 5 | 1 |   |
|   |   | 24 h | 5 | 1 |   |
| 4 | LiOPiv | 3 h | 11 | 2 |   |
|   |   | 6 h | 19 | 2 |   |
|   |   | 24 h | 23 | 2 |   |
| 5 | LiF | 3 h | 3 | 1 |   |
|   |   | 6 h | 3 | 1 |   |
|   |   | 24 h | 4 | 1 |   |
| 6 | NaOAc | 3 h | 19 | 13 |   |
|   |   | 6 h | 39 | 32 |   |
|   |   | 24 h | 89 | 83 | 90 |
| 7 | NaTFA | 3 h | 2 | 1 |   |
|   |   | 6 h | 6 | 3 |   |
|   |   | 24 h | 14 | 10 |   |
| 8 | Na$_2$CO$_3$ | 3h | 8 | 4 |   |
|   |   | 6 h | 13 | 8 |   |
|   |   | 24 h | 36 | 32 | 38 |
| 9 | KOAc | 3 h | 0 | 0 |   |
|   |   | 6 h | 3 | 1 |   |
|   |   | 24 h | 12 | 7 |   |
| 10 | CsF | 3 h | 2 | 2 |   |
|   |   | 6 h | 6 | 2 |   |
|   |   | 24 h | 31 | 7 |   |
| 11 | Cs$_2$CO$_3$ | 3h | 1 | 0 |   |
|   |   | 6 h | 2 | 0 |   |
|   |   | 24 h | 8 | 1 |   |
| 12 | CsOAc | 3 h | 0 | 0 |   |
|   |   | 6 h | 0 | 0 |   |
|   |   | 24 h | 1 | 1 |   |
| 13 | ZnF$_2$ | 3 h | 5 | 2 |   |
|   |   | 6 h | 7 | 2 |   |
|   |   | 24 h | 7 | 2 |   |
| 14 | Zn(OAc)$_2$ | 3h | 45 | 37 |   |
|   |   | 6 h | 54 | 43 |   |
|   |   | 24 h | 55 | 43 | 25 |
| 15 | CuF$_2$ | 3 h | 9 | 4 |   |
|   |   | 6 h | 10 | 4 |   |
|   |   | 24 h | 10 | 4 |   |
| 16 | None | 3 h | 4 | 2 |   |
|   |   | 6 h | 4 | 2 |   |
|   |   | 24 h | 5 | 2 |   |

(S)-tert-Butyl 2-(1'-naphthyl)propionate

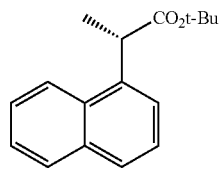 [SMILES: C[C@H](C(=O)OC(C)(C)C)c1cccc2ccccc12]

Conversion: 3 h, 95%; 6 h, 100%. The coupling product was produced in 99% GC yield. Ee of the product was determined to be 90% by chiral HPLC analysis. When Pd(dba)$_2$ (1.2 mg, 0.002 mmol) was used in place of PdMe$_2$ (TMEDA), ZnF$_2$ (2 mg, 0.02 mmol) was needed together with LiOAc (13 mg, 0.20 mmol). Conversion: 3 h, 10%; 24 h, 100%. The coupling product was produced in 99% GC yield. Ee of the product was determined to be 92% by chiral HPLC analysis. $^1$H NMR (400 MHz, CDCl$_3$): δ 8.11 (d, J=8.4 Hz, 1H), 7.87 (dd, J 7.8, 1.8 Hz, 1H), 7.78-7.75 (m, 1H), 7.56-7.42 (m, 4H), 4.42 (q, J=7.2 Hz, 1H), 1.61 (d, J=7.2 Hz, 3H), 1.42 (s, 9H). $^{13}$C NMR (100 MHz, CDCl$_3$): δ 174.4, 137.7, 134.2, 131.7, 129.1, 127.6, 126.2, 125.77, 125.69, 124.4, 123.6, 80.9, 42.5, 28.1, 18.3. GCMS (EI): calcd for C$_{17}$H$_{20}$O$_2$ M: 256.15. Found: 256.07.

(S)-Methyl 2-(1'-naphthyl)propionate [22561-78-0]

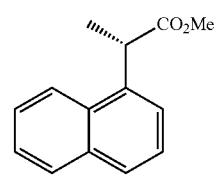 [SMILES: COC(=O)[C@@H](C)c1cccc2ccccc12]

The reaction was finished within 3 hours at 50° C. The coupling product was produced in 99% GC yield. The ee of the product was determined to be 5% by chiral HPLC analysis (Daicel CHIRALCEL OJ-H; hexanes: i-PrOH=98:2; detection wavelengths=254 nm and 227 nm; flow rate=1.0 mL/min). T$_R$=14.7 min (major) and 18.0 min (minor). $^1$H NMR (400 MHz, CDCl$_3$): δ 8.08 (d, J=8.4 Hz, 1H), 7.88 (d, J=7.8 Hz, 1H), 7.79-7.77 (m, 1H), 7.57-7.45 (m, 4H), 4.52 (q, J=7.1 Hz, 1H), 3.66 (s, 3H), 1.67 (d, J=7.1 Hz, 3H). GCMS (EI): calcd for C$_{14}$H$_{14}$O$_2$ M: 214.10. Found: 214.02.

(S)-Ethyl 2-(1'-naphthyl)propionate

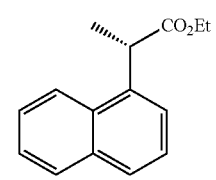 [SMILES: CCOC(=O)[C@@H](C)c1cccc2ccccc12]

The reaction was finished within 3 hours at 50° C. The coupling product was produced in 99% GC yield. The ee of the product was determined to be 5% by chiral HPLC analysis (Daicel CHIRALCEL OJ-H; hexanes: i-PrOH=98:2; detection wavelengths=254 nm and 227 nm; flow rate=1.0 mL/min). T$_R$=11.1 min (major) and 16.5 min (minor). $^1$H NMR (400 MHz, CDCl$_3$): δ 8.11 (d, J=8.4 Hz, 1H), 7.88 (d, J=8.0 Hz, 1H), 7.79-7.76 (m, 1H), 7.57-7.44 (m, 4H), 4.51 (q, J=7.1 Hz, 1H), 4.21-4.09 (m, 2H), 1.66 (d, J=7.1 Hz, 3H), 1.18 (t, J=7.1 Hz, 3H). $^{13}$C NMR (100 MHz, CDCl$_3$): δ 175.1, 137.2, 134.2, 131.6, 129.2, 127.9, 126.4, 125.8 (2 overlapping signals), 124.6, 123.4, 61.0, 41.7, 18.4, 14.3. GCMS (EI): calcd for C$_{15}$H$_{16}$O$_2$ M: 228.12. Found: 228.03.

(S)-Cyclohexyl 2-(1'-naphthyl)propionate

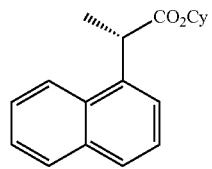

The reaction was finished within 3 hours at 50° C. The coupling product was produced in 99% GC yield. The ee of the product was determined to be 67% based on chiral HPLC analysis (Daicel CHIRALCEL OJ-H; hexanes: i-PrOH=98:2; detection wavelengths=254 nm and 227 nm; flow rate=0.5 mL/min). T$_R$=15.0 min (major) and 19.1 min (minor). $^1$H NMR (400 MHz, CDCl$_3$): δ 8.12 (d, J=8.4 Hz, 1H), 7.87 (d, J=8.0 Hz, 1H), 7.76 (d, J=6.9 Hz, 1H), 7.55-7.42 (m, 4H), 4.82-4.79 (m, 1H), 4.52-4.46 (m, 1H), 1.77-1.16 (m, 13H); $^{13}$C NMR (100 MHz, CDCl$_3$): δ 174.6, 137.4, 134.2, 131.7, 129.1, 127.8, 126.3, 125.77, 125.74, 124.5, 123.5, 73.0, 41.8, 31.6, 31.4, 25.5, 23.71, 23.58, 18.3. GCMS (EI): calcd for C$_{19}$H$_{22}$O$_2$ M: 282.16. Found: 282.14.

(S)-T-Naphthyl 2-(1'-naphthyl)propionate

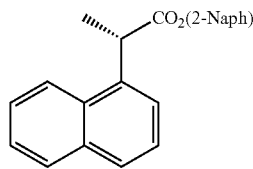

The reaction was finished within 3 hours at 50° C. The coupling product was produced in 99% GC yield. The ee of the product was determined to be 52% based on chiral HPLC analysis (Daicel CHIRALCEL OD-H; hexanes: i-PrOH=98:2; detection wavelengths=254 nm and 227 nm; flow rate=1.0 mL/min). T$_R$=10.1 min (major) and 13.1 min (minor). $^1$H NMR (400 MHz, CDCl$_3$): δ 8.26 (d, J=8.4 Hz, 1H), 7.94 (d, J=8.0 Hz, 1H), 7.86 (d, J=8.2 Hz, 1H), 7.82-7.74 (m, 3H), 7.65-7.61 (m, 2H), 7.58-7.53 (m, 2H), 7.49-7.42 (m, 3H), 7.11 (dd, J=8.4, 2.4 Hz, 1H), 4.82 (q, J=7.2 Hz, 1H), 1.83 (d, J=7.2 Hz, 3H). $^{13}$C NMR (100 MHz, CDCl$_3$): δ 173.9, 148.7, 136.6, 134.4, 133.9, 131.64, 131.55, 129.5, 129.4, 128.3, 127.94, 127.81, 126.76, 126.70, 126.0, 125.90, 125.85, 124.9, 123.3, 121.2, 118.6, 42.0, 18.4. GCMS (EI): calcd for C$_{23}$H$_{18}$O$_2$ M: 326.13. Found: 326.09.

VI. Isolation of Arylation Products

General procedure for asymmetric arylation: In an argon-filled glove box, a dry 4 mL vial was charged with PdMe$_2$ (TMEDA) (2.5 mg, 0.010 mmol), ligand L6 (7.4 mg, 0.012 mmol) and 1.0 mL of dry α,α,α-trifluorotoluene. After stirring at 25° C. for 30 minutes, the mixture was treated successively with anhydrous LiOAc (66 mg, 1.0 mmol), aryl triflate (0.50 mmol), (E)-O-trimethylsilyl ketene acetal (0.75 mmol) and GC standard n-dodecane (50 uL). The vial was capped tightly and the mixture was heated with stirring in a 50° C. (internal temperature) heating block. After aryl triflate was fully consumed (monitored by GC and TLC), the reaction mixture was cooled to 25° C. and filtered through a pad of silica gel with diethyl ether washings (20 mL). The filtrate was concentrated and the residue was purified by flash silica gel chromatography. The general procedure was used for all the isolation of the coupling products on the 0.50 mmol scale (aryl triflate), unless stated otherwise.

For chiral HPLC analysis of the enantioenriched coupling products, the racemic products were prepared using a similar procedure with SPhos as ligand instead of L6.

(S)-tert-Butyl 2-phenylpropionate [59415-37-1]

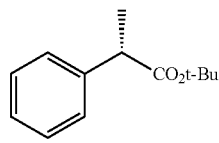

The reaction was finished within 18 hours at 50° C. The title compound was obtained as colorless oil (96 mg, 93% yield) by flash chromatography using ethyl acetate/hexane (1:40) as eluent. The ee of the purified products was determined to be 90% based on chiral HPLC analysis (Daicel CHIRALCEL OJ-H; hexanes: i-PrOH=99.5:0.5; detection wave-lengths=254 nm and 227 nm; flow rate=0.5 mL/min). $T_R$=17.0 min (minor) and 18.7 min (major). $[a]^{20}_D$=D+24.3° (c=3.3, CHCl$_3$). $^1$H NMR (400 MHz, CDCl$_3$): δ 7.33-7.21 (m, 5H), 3.61 (q, J=7.1, 1H), 1.45 (d, J=7.1 Hz, 3H), 1.39 (s, 9H). $^{13}$C NMR (100 MHz, CDCl$_3$): δ 174.1, 141.4, 128.7, 127.6, 127.0, 80.7, 46.7, 28.2, 18.8. GCMS (EI): calcd for $C_{13}H_{18}O_2$ M: 206.13. Found: 205.96.

(S)-tert-Butyl 2-(4'-ethylbenzoate)propionate

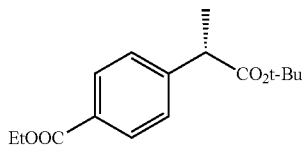 [SMILES: CCOC(=O)c1ccc([C@H](C)C(=O)OC(C)(C)C)cc1]

The reaction was finished within 9 hours at 50° C. The title compound was obtained as colorless oil (1.20 mg, 86% yield) by flash chromatography using ethyl acetate/hexane (1:30) as eluent. The ee of the purified products was determined to be 89% based on chiral HPLC analysis (Daicel CHIRALCEL 03-H; hexanes: i-PrOH=98:2; detection wave-lengths=254 nm and 227 nm; flow rate=0.4 mL/min). $T_R$=15.3 min (minor) and 16.1 min (major). $[a]^{20}_D$=+23.0° (c=2.4, CHCl$_3$). $^1$H NMR (300 MHz, CDCl$_3$): δ 8.00-7.97 (m, 2H), 7.36-7.33 (m, 2H), 4.36 (q, J=7.1 Hz, 2H), 3.65 (q, J=7.1 Hz, 1H), 1.45 (d, J=7.2 Hz, 1H), 1.44-1.35 (m, 12H). $^{13}$C NMR (75 MHz, CDCl$_3$): δ 173.3, 166.7, 146.4, 130.0, 129.4, 127.6, 81.0, 61.0, 46.7, 28.1, 18.5, 14.5. GCMS (EI): calcd for $C_{16}H_{23}O_4$ (M+H)$^+$: 279.16. Found: 279.18.

(S)-tert-Butyl-2-(2'-methylphenyl)propionate

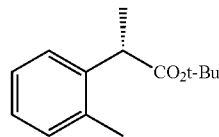 [SMILES: Cc1ccccc1[C@H](C)C(=O)OC(C)(C)C]

LiOAc (66 mg, 1.0 mmol), ZnF$_2$ co-activator (10 mg, 0.10 mmol) and silyl ketene acetal (202 mg, 1.0 mmol) were used. The reaction was finished within 24 hours at 50° C. The title compound was obtained as colorless oil (97 mg, 88% yield) by flash chromatography using ethyl acetate/hexane (1:50) as eluent. The ee of the purified products was determined to be 89% based on chiral HPLC analysis (Daicel CHIRALCEL OJ-H; hexanes: i-PrOH=99.5:0.5; detection wavelengths=254 nm and 227 nm; flow rate=0.4 mL/min). $T_R$=13.0 min (minor) and 13.8 min (major). $[a]^{20}_D$=+48.6° (c=3.1, CHCl$_3$). $^1$H NMR (300 MHz, CDCl$_3$): δ 7.27-7.25 (m, 1H), 7.20-7.12 (m, 3H), 3.85 (q, J=7.1 Hz, 1H), 2.36 (s, 3H), 1.42 (d, J=7.1 Hz, 3H), 1.38 (s, 9H). $^{13}$C NMR (75 MHz, CDCl$_3$): δ 174.3, 139.9, 135.9, 130.5, 126.8, 126.50, 126.46, 80.6, 42.4, 28.2, 19.8, 17.9. GCMS (EI): calcd for $C_{14}H_{20}O_2$ M: 220.15. Found: 220.11.

(S)-tert-Butyl 2-(2'-anisyl)propionate

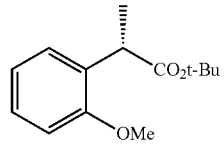 [SMILES: COc1ccccc1[C@H](C)C(=O)OC(C)(C)C]

LiOAc (99 mg, 0.15 mmol), ZnF$_2$ co-activator (10 mg, 0.10 mmol) and silyl ketene acetal (303 mg, 1.5 mmol) were used. The reaction was finished within 36 hours. The title compound was obtained as colorless oil (107 mg, 91% yield) by flash chromatography using ethyl acetate/hexane (1:40) as eluent. The ee of the purified products was determined to be 91% based on chiral HPLC analysis (Daicel CHIRALCEL OJ-H; hexanes: i-PrOH=98:2; detection wavelengths=254 nm and 227 nm; flow rate=0.5 mL/min). $T_R$=11.0 min (major) and 12.0 min (minor). $[a]^{20}_D$=+34.5° (c=3.7, CHCl$_3$). $^1$H NMR (400 MHz, CDCl$_3$): δ 7.24-7.20 (m, 2H), 6.92 (dd, J=7.5, 7.4 Hz, 1H), 6.86 (d, J=8.4 Hz, 1H), 3.93 (q, J=7.2 Hz, 1H), 3.82 (s, 3H), 1.42-1.40 (m, 12H). $^{13}$C NMR (100 MHz, CDCl$_3$): δ 174.6, 156.9, 130.4, 127.99, 127.94, 120.8, 110.6, 80.2, 55.5, 40.5, 28.2, 17.4. GCMS (EI): calcd for $C_{14}H_{20}O_3$ M: 236.14. Found: 236.12.

(S)-tert-Butyl 2-(2'-cyanophenyl) propionate

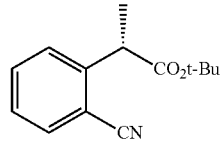 [SMILES: C[C@H](C(=O)OC(C)(C)C)c1ccccc1C#N]

The reaction was finished within 18 hours. The title compound was obtained as colorless oil (111 mg, 96% yield) by flash chromatography using ethyl acetate/hexane (1:30) as eluent.

The ee of the purified products was determined to be 91% based on chiral HPLC analysis (Daicel CHIRALCEL OD-H; hexanes: i-PrOH=99:1; detection wavelengths=254 nm and 227 nm; flow rate=0.5 mL/min). $T_R$=13.1 min (minor) and 14.1 min (major). $[a]^{20}{}_D$=+95.8° (c=2.6, CHCl$_3$). $^1$H NMR (300 MHz, CDCl$_3$): δ 7.63 (dd, J=7.8, 1.0 Hz, 1H), 7.55 (ddd, J=7.8, 7.6, 1.2 Hz, 1H), 7.44 (dd, J=7.8, 1.0 Hz, 1H), 7.33 (ddd, J=7.8, 7.6, 1.2 Hz, 1H), 4.08 (q, J=7.2, 1H), 1.50 (d, J=7.2 Hz, 3H), 1.39 (s, 9H). $^{13}$C NMR (75 MHz, CDCl$_3$): δ 172.3, 145.12, 133.2, 133.1, 127.6, 127.5, 117.9, 112.9, 81.6, 44.6, 28.1, 18.2. GCMS (EI): calcd for C$_{14}$H$_{18}$NO$_2$ (M+H)$^+$: 232.14. Found: 232.09.

(S)-tert-Butyl 2-(2'-nitrophenyl)propionate

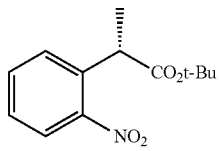

Pd(dba)$_2$ (5.8 mg, 0.010 mmol), ZnF$_2$ co-activator (10 mg, 0.10 mmol), LiOAc (66 mg, 1.0 mmol), and silyl ketene acetal (152 mg, 0.75 mmol) were used. The reaction was finished within 24 hours at 50° C. The title compound was obtained as yellow oil (121 mg, 96% yield) by flash chromatography using ethyl acetate/hexane (1:30) as eluent. The ee of the purified products was determined to be 90% based on chiral HPLC analysis (Daicel CHIRALCEL AD-H; hexanes: i-PrOH=99:1; detection wavelengths=254 nm and 227 nm; flow rate=0.5 mL/min). $T_R$=12.7 min (major) and 13.6 min (minor). $[a]^{20}{}_D$=+136.4° (c=2.5, CHCl$_3$). $^1$H NMR (400 MHz, CDCl$_3$): δ 7.90 (dd, J=8.1, 1.2 Hz, 1H), 7.60-7.56 (m, 1H), 7.48 (dd, J=7.8, 1.1 Hz, 1H), 7.42-7.38 (m, 1H), 4.21 (q, J=7.2 Hz, 1H), 1.56 (d, J=7.2 Hz, 3H), 1.38 (s, 9H). $^{13}$C NMR (100 MHz, CDCl$_3$): δ 172.5, 149.4, 135.9, 133.2, 129.7, 127.9, 124.9, 81.6, 42.3, 28.0, 17.8. GCMS (EI): calcd for C$_{13}$H$_{17}$NO$_4$ M: 251.12. Found: 251.13.

(S)-tert-Butyl 2-(2'-naphthyl) propionate

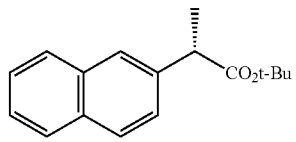 [SMILES: C[C@H](C(=O)OC(C)(C)C)c1ccc2ccccc2c1]

Pd(dba)$_2$ (5.8 mg, 0.010 mmol), ZnF$_2$ co-activator (10 mg, 0.10 mmol), LiOAc (66 mg, 1.0 mmol) and silyl ketene acetal (152 mg, 0.75 mmol) were used. The reaction was finished within 24 hours at 50° C. The title compound was obtained as white solid (125 mg, 98% yield) by flash chromatography using ethyl acetate/hexane (1:50) as eluent. The ee of the purified products was determined to be 90% based on chiral HPLC analysis (Daicel CHIRALCEL OJ-H; hexanes: i-PrOH=98:2; detection wavelengths=254 nm and 227 nm; flow rate=0.5 mL/min). $T_R$=14.3 min (minor) and 16.2 min (major). $[a]^{20}{}_D$=+28.6° (c=2.9, CHCl$_3$). $^1$H NMR (400 MHz, CDCl$_3$): δ 7.84-7.80 (m, 3H), 7.74 (s, 1H), 7.48-7.45 (m, 3H), 3.80 (q, J=7.2 Hz, 1H), 1.56 (d, J=7.2 Hz, 3H), 1.41 (s, 9H). $^{13}$C NMR (100 MHz, CDCl$_3$): δ 174.0, 138.9, 133.7, 132.7, 128.3, 128.0, 127.8, 126.20, 126.18, 126.07, 125.8, 80.8, 46.8, 28.2, 18.8. GCMS (EI): calcd for C$_{17}$H$_{20}$O$_2$ M: 256.15. Found: 256.10.

(S)-tert-Butyl 2-(6'-methoxy-2'-naphthyl)propionate [92455-03-3]

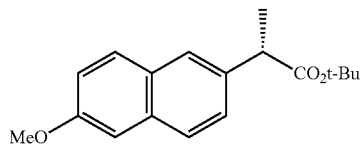 [SMILES: COc1ccc2cc([C@H](C)C(=O)OC(C)(C)C)ccc2c1]

Silyl ketene acetal (303 mg, 1.5 mmol) and LiOAc (99 mg, 1.5 mmol) were used. The reaction was finished within 36 hours at 50° C. The title compound was obtained as white solid (142 mg, 99% yield) by flash chromatography using ethyl acetate/hexane (1:30) as eluent. The ee of the purified products was determined to be 90% based on chiral HPLC analysis (Daicel CHIRALCEL AS-H; hexanes: i-PrOH=98:2; detection wavelengths=254 nm and 227 nm; flow rate=0.4 mL/min). $T_R$=12.3 min (minor) and 12.9 min (major). $[a]^{20}{}_D$=+21.3° (c=2.3, CHCl$_3$). $^1$H NMR (300 MHz, CDCl$_3$): δ 7.73-7.66 (m, 3H), 7.42 (dd, =8.5, 1.8 Hz, 1H), 7.16-7.13 (m, 2H), 3.92 (s, 3H), 3.75 (q, J=7.1 Hz, 1H), 1.53 (d, J=7.1 Hz, 3H), 1.40 (s, 9H). $^{13}$C NMR (75 MHz, CDCl$_3$): δ 174.2, 157.8, 136.6, 133.8, 129.5, 129.2, 127.1, 126.6, 126.0, 119.0, 105.8, 80.7, 55.5, 46.6, 28.2, 18.8. GCMS (EI): calcd for C$_{18}$H$_{22}$O$_3$ M: 286.16. Found: 286.07.

(S)-tert-Butyl 2-(3'-benzoylphenyl)propionate

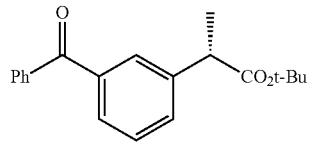 [SMILES: C[C@H](C(=O)OC(C)(C)C)c1cccc(C(=O)c2ccccc2)c1]

The reaction was finished within 12 hours at 50° C. The title compound was obtained as colorless oil (150 mg, 97% yield) by flash chromatography using ethyl acetate/hexane (1:30) as eluent. The ee of the purified products was determined to be 88% based on chiral HPLC analysis (Daicel CHIRALCEL AD-H; hexanes: i-PrOH=99:1; detection wavelengths=254 nm and 227 nm; flow rate=0.5 mL/min). $T_R$=25.4 min (minor) and 28.4 min (major). $[a]^{20}{}_D$=D+26.4° (c=2.5, CHCl$_3$). $^1$H NMR (400 MHz, CDCl$_3$): δ 7.79 (d, J=7.3 Hz, 2H), 7.73 (s, 1H), 7.67 (d, J=7.6, Hz, 1H), 7.58 (dd, 0.1=7.8, 7.6 Hz, 1H), 7.53 (d, J=7.8 Hz, 1H), 7.49-7.41 (m, 3H), 3.68 (q, J=7.2 Hz, 1H), 1.47 (d, J=7.2 Hz, 3H), 1.40 (s, 9H). $^{13}$C NMR (100 MHz, CDCl$_3$): δ 196.8, 173.5, 141.6, 138.0, 137.8, 132.6, 131.7, 130.2, 129.4, 128.9, 128.64, 128.47, 81.0, 46.6, 28.1, 18.7. GCMS (EI): calcd for C$_{20}$H$_{22}$O$_3$ M: 310.16. Found: 310.16.

(S)-tert-Butyl 2-(2'-methoxycarbonyl-3'-thienyl)propionate

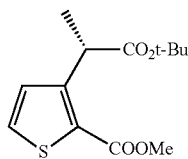 [SMILES: COC(=O)c1sccc1[C@H](C)C(=O)OC(C)(C)C]

Pd(dba)$_2$ (5.8 mg, 0.010 mmol) was used as palladium source. The reaction was finished within 4 hours at 50° C. The title compound was obtained as colorless oil (130 mg, 96% yield) by flash chromatography using ethyl acetate/hexane (1:30) as eluent. The ee of the purified products was determined to be 96% based on chiral HPLC analysis (Daicel CHIRALCEL AD-H; hexanes: i-PrOH=99:1; detection wavelengths=254 nm and 227 nm; flow rate=0.5 mL/min). $T_R$=12.5 min (major) and 14.0 min (minor). $[a]^{20}{}_D$=+80.3° (c=3.2, CHCl$_3$). $^1$H NMR (400 MHz, CDCl$_3$): δ 7.42 (d, J=5.2 Hz, 1H), 7.10 (d, J=5.2 Hz, 1H), 4.71 (q, J=7.2 Hz, 1H), 3.86 (s, 3H), 1.44 (d, J=7.2 Hz, 3H), 1.40 (s, 9H). $^{13}$C NMR (100 MHz, CDCl$_3$): δ 173.4, 162.9, 149.0, 130.6, 128.6, 127.3, 80.8, 52.1, 40.3, 28.2, 18.4. GCMS (EI): calcd for C$_{13}$H$_{18}$O$_4$S M: 270.09. Found: 270.07.

(S)-tert-Butyl 2-(2'-methyl-8'-quinolinyl)propionate

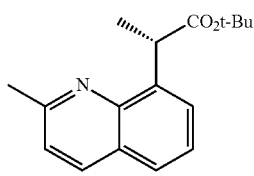 [SMILES: Cc1ccc2cccc([C@H](C)C(=O)OC(C)(C)C)c2n1]

Pd(dba)$_2$ (5.8 mg, 0.010 mmol), ZnF$_2$ co-activator (10 mg, 0.10 mmol), LiOAc (66 mg, 1.0 mmol) and silyl ketene acetal (152 mg, 0.75 mmol) were used. The reaction was finished within 24 hours at 50° C. The title compound was obtained as colorless oil (129 mg, 95% yield) by flash chromatography using ethyl acetate/hexane (1:30) as eluent. The ee of the purified products was determined to be 96% by chiral HPLC analysis (Daicel CHIRALCEL OJ-H; hexanes: i-PrOH=98:2; detection wavelengths=254 nm and 227 nm; flow rate=0.5 mL/min). $T_R$=9.9 min (major) and 11.3 min (minor). $[a]^{20}{}_D$=+68.5° (c=2.0, CHCl$_3$). $^1$H NMR (400 MHz, CDCl$_3$): δ 7.99 (d, J=8.4 Hz, 1H), 7.65 (dd, J=8.0, 1.2 Hz, 1H), 7.59 (dd, J=7.2, 1.2 Hz, 1H), 7.42 (dd, J=8.0, 7.2 Hz, 1H), 7.25 (d, J=8.4 Hz, 1H), 4.86 (q, J=7.2 Hz, 1H), 2.72 (s, 3H), 1.60 (d, J=7.2 Hz, 3H), 1.40 (s, 9H). $^{13}$C NMR (100 MHz, CDCl$_3$): δ 175.3, 157.9, 145.8, 140.0, 136.3, 127.1, 126.6, 126.5, 125.5, 121.9, 80.0, 41.4, 28.2, 25.7, 18.2. GCMS (EI): calcd for C$_{17}$H$_{21}$NO$_2$ M: 271.16. Found: 270.99.

(S)-tert-Butyl 2-(1'-naphthyl)propionate

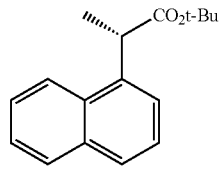

Pd(dba)$_2$ (5.8 mg, 0.010 mmol), ZnF$_2$ co-activator (10 mg, 0.10 mmol), LiOAc (66 mg, 1.0 mmol) and silyl ketene acetal (152 mg, 0.75 mmol) were used. The reaction was finished within 24 hours at 50° C. The title compound was obtained as colorless oil (127 mg, 99% yield) by flash chromatography using ethyl acetate/hexane (1:50) as eluent. The ee of the purified products was determined to be 92% by chiral HPLC analysis (Daicel CHIRALCEL OJ-H; hexanes: i-PrOH=98:2; detection wavelengths=254 nm and 227 nm; flow rate=0.5 mL/min). $T_R$=13.2 min (major) and 15.8 min (minor). $[a]^{20}{}_D$=+95.5° (c=2.2, CHCl$_3$). $^1$H NMR (400 MHz, CDCl$_3$): δ 8.11 (d, J=8.4 Hz, 1H), 7.87 (dd, J=7.8, 1.8 Hz, 1H), 7.78-7.75 (m, 1H), 7.56-7.42 (m, 4H), 4.42 (q, J=7.2 Hz, 1H), 1.61 (d, J=7.2 Hz, 3H), 1.42 (s, 9H). $^{13}$C NMR (100 MHz, CDCl$_3$): δ 174.4, 137.7, 134.2, 131.7, 129.1, 127.6, 126.2, 125.77, 125.69, 124.4, 123.6, 80.9, 42.5, 28.1, 18.3. GCMS (EI): calcd for C$_{17}$H$_{20}$O$_2$ M: 256.15. Found: 256.07.

(S)-tert-Butyl 2-(1'-naphthyl)butyrate

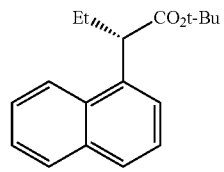

The reaction was finished within 6 hours at 50° C. The title compound was obtained as colorless oil (134 mg, 98% yield) by flash chromatography using ethyl acetate/hexane (1:50) as eluent. The ee of the purified products was determined to be 91% by chiral HPLC analysis (Daicel CHIRALCEL OJ-H; hexanes: i-PrOH=98:2; detection wavelengths=254 nm and 227 nm; flow rate=0.5 mL/min). $T_R$=9.7 min (minor) and 11.4 min (major). $[a]^{20}{}_D$=+110.8° (c=2.5, CHCl$_3$). $^1$H NMR (400 MHz, CDCl$_3$): δ 8.18 (d, J=8.4 Hz, 1H), 7.87 (d, J=8.0 Hz, 1H), 7.77 (d, J=8.0 Hz, 1H), 7.56-7.44 (m, 4H), 4.21 (dd, J=8.6, 6.3 Hz, 1H), 2.32-2.21 (m, 1H), 1.98-1.87 (m, 1H), 1.39 (s, 9H), 1.02 (t, J=7.4 Hz, 3H). $^{13}$C NMR (100 MHz, CDCl$_3$): δ 173.7, 136.3, 134.2, 132.0, 129.0, 127.6, 126.2, 125.72, 125.62, 124.7, 123.6, 80.8, 49.7, 28.2, 26.6, 12.8. GCMS (EI): calcd for C$_{18}$H$_{22}$O$_2$ M: 270.16. Found: 270.12.

(S)-tert-Butyl 2-(1'-naphthyl)dodecanoate

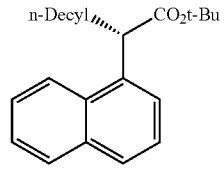

The reaction was finished within 6 hours at 50° C. The title compound was obtained as colorless oil (189 mg, 99% yield) by flash chromatography using ethyl acetate/hexane (1:50) as eluent. The ee of the purified products was determined to be 87% by chiral HPLC analysis (Daicel CHIRALCEL OD-H; hexanes: i-PrOH=98:2; detection wavelengths=254 nm and 227 nm; flow rate=0.5 mL/min). $T_R$=8.4 min (minor) and 9.9 min (major). $[a]^{20}{}_D$=+55.3

(c=2.8, CHCl$_3$). $^1$H NMR (400 MHz, CDCl$_3$): δ 8.16 (d, J=8.4 Hz, 1H), 7.86 (dd, J=7.9, 1.5 Hz, 1H), 7.75 (d, J=8.4 Hz, 1H), 7.55-7.43 (m, 4H), 4.27 (dd, J=8.7, 6.2 Hz, 1H), 2.26-2.17 (m, 1H), 1.89-1.81 (m, 1H), 1.37-1.25 (m, 25H), 0.88 (t, J=7.0 Hz, 3H). $^{13}$C NMR (100 MHz, CDCl$_3$): δ 173.8, 136.5, 134.2, 132.0, 129.1, 127.6, 126.2, 125.76, 125.63, 124.7, 123.6, 80.8, 48.0, 33.5, 32.1, 29.80 (2 overlapping signals), 29.77, 29.69, 29.5, 28.28, 28.18, 22.9, 14.3. GCMS (EI): calcd for C$_{26}$H$_{38}$O$_2$ M: 382.29. Found: 382.22.

(S)-tert-Butyl 2-(1'-naphthyl)-3-phenylpropionate

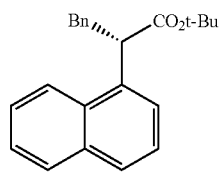 [SMILES: CC(C)(C)OC(=O)[C@@H](Cc1ccccc1)c1cccc2ccccc12]

Pd(dba)$_2$ (5.8 mg, 0.010 mmol), ZnF$_2$ co-activator (10 mg, 0.10 mmol), LiOAc (66 mg, 1.0 mmol) and silyl ketene acetal (152 mg, 0.75 mmol) were used. The reaction was finished within 20 hours at 50° C. The title compound was obtained as white solid (156 mg, 93% yield) by flash chromatography using ethyl acetate/hexane (1:50) as eluent, followed by bulb-to-bulb distillation (90° C., 50 mTorr) to remove the tert-butyl 3-phenylpro-pionate and C-TMS ester. The ee of the purified products was determined to be 96% by chiral. HPLC analysis (Daicel CHIRALCEL OJ-H; hexanes: i-PrOH=98:2; detection wavelengths=254 nm and 227 nm; flow rate=0.5 mL/min). T$_R$=12.0 min (major) and 16.7 min (minor). [a]$^{20}_D$=+96.8° (c=3.0, CHCl$_3$). $^1$H NMR (400 MHz, CDCl$_3$): δ 8.03 (d, J=8.4 Hz, 1H), 7.72 (d, J=8.4 Hz, 1H), 7.63 (d, J=8.2 Hz, 1H), 7.45 (d, J=7.2 Hz, 1H), 7.41-7.30 (m, 3H), 7.14-7.03 (m, 5H), 4.46 (dd, J=9.8, 5.2 Hz, 1H), 3.41 (dd, J=13.8, 9.8 Hz, 1H), 2.97 (dd, J=13.8, 5.2 Hz, 1H), 1.14 (s, 9H). $^{13}$C NMR (100 MHz, CDCl$_3$): δ 173.0, 140.0, 135.9, 134.2, 131.7, 129.2, 129.1, 128.5, 127.9, 126.5, 126.4, 125.8, 125.7, 124.9, 123.5, 81.2, 49.9, 39.6, 28.1. GCMS (EI): calcd for C$_{23}$H$_{24}$O$_2$ M: 332.18. Found: 332.10.

VII. Gram-Scale Synthesis of (S)-Naproxen

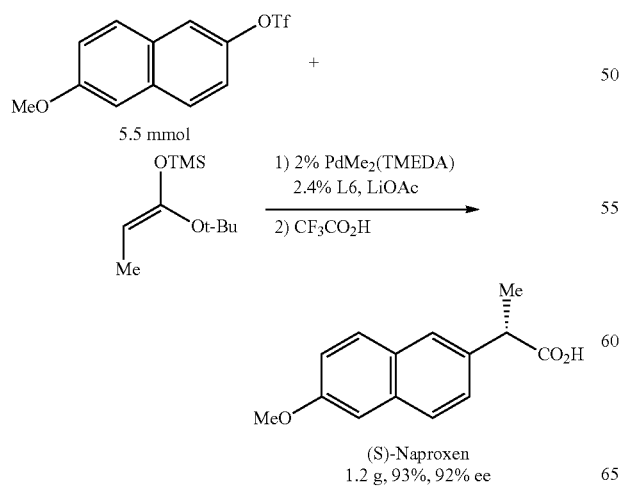

(S)-Naproxen
1.2 g, 93%, 92% ee

Procedure using standard Schlenk technique: Under argon, a 50 mL dry Schlenk tube was charged with PdMe$_2$(TMEDA) (28 mg, 0.11 mmol), ligand L6 (81 mg, 0.13 mmol) and dry α,α,α-trifluorotoluene (10 mL). After the resulting mixture was stirred at 25° C. for 30 minutes, anhydrous lithium acetate (1.10 g, 16.5 mmol), 6-methoxyl-2-naphthyl trifluoromethanesulfonate (1.68 g, 5.5 mmol) and (1E)-1-tert-butoxy-1-(trimethylsiloxy)propene (3.30 g, 16.5 mmol) were added into the Schlenk tube against sufficient argon flow, followed by dry n-dodecane (550 uL). The Schlenk tube was tightly capped and the reaction mixture was heated with vigorous stirring in a 50° C. (external temperature) oil bath. After stirring at 50° C. for 60 hours, the reaction reached completion. The conversion of aryl triflate was monitored by GC (24 h, 82% conversion; 48 h, 94% conversion; 60 h, 100% conversion). At the end of the reaction, the mixture was cooled to 25° C., and filtered through a pad of silica gel (~20 g) with washings of 1:20 ethyl acetate/hexane (300 mL). The filtrate was concentrated on a rotary evaporator. The resulting residue was directly dissolved in analytical-grade dichloromethane (10 mL) under argon, followed by the addition of trifluoroacetic acid (10 mL). The hydrolysis was carried out at 25° C. with stirring for 4 hours. At the end of the reaction, the solvent and trifluoroacetic acid was concentrated on a rotary evaporator. The residue was directly purified by flash chromatography (1:3 ethyl acetate/hexane), which afforded (S)-Naproxen (1.17 g, 93% yield over two steps) as off-white solid. The ee of the purified (S)-Naproxen was determined to be 92% by chiral HPLC analysis (Daicel CHIRALCEL AS-ft hexanes: i-PrOH=90:10; detection wavelengths=254 nm and 227 nm; flow rate=0.5 mL/min). T$_R$=19.8 min (minor) and 23.0 min (major). The ee was slightly higher than that of the 0.5 mmol scale reaction because the temperature was slightly lower. The ee of (S)-Naproxen was improved to 99% after a single crystallization from a 1:2 mixed solvent of hot acetone/hexane (713 mg, 61% yield, colorless needle). A second crop of crystals were obtained from the mother liquor with 95% ee, which was improved to 99% ee after recrystallization (136 mg, 12% yield). For a sample with 99% ee, [a]$^{20}_D$=+66.7° (c=1.1, CHCl$_3$), which is close to the reported value ([a]$^{25}$D=+66° for pure (S)-Naproxen). $^1$H NMR (400 MHz, CDCl$_3$): δ 11.3 (br, 1H), 7.71-7.68 (m, 3H), 7.41 (dd, J=8.4, 1.6 Hz, 1H), 7.15-7.10 (m, 2H), 3.91 (s, 3H), 3.87 (q, J=7.2 Hz, 1H), 1.59 (d, J=7.2 Hz, 3H).

Although the disclosure has been described with reference to the above examples, it will be understood that modifications and variations are encompassed within the spirit and scope of the disclosure. Accordingly, the disclosure is limited only by the following claims.

What is claimed is:

1. A method of asymmetrically synthesizing an α-aryl compound of Formula I:

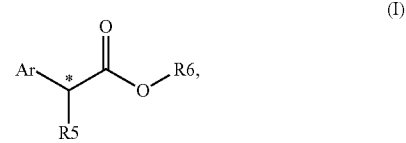

(I)

or a pharmaceutically acceptable salt thereof, the method comprising the step of reacting a compound of Formula II with a compound of Formula III in the presence of a palladium catalyst, an activator, a compound of Formula IV, and optionally a solvent, to produce the asymmetric α-aryl compound of Formula I:

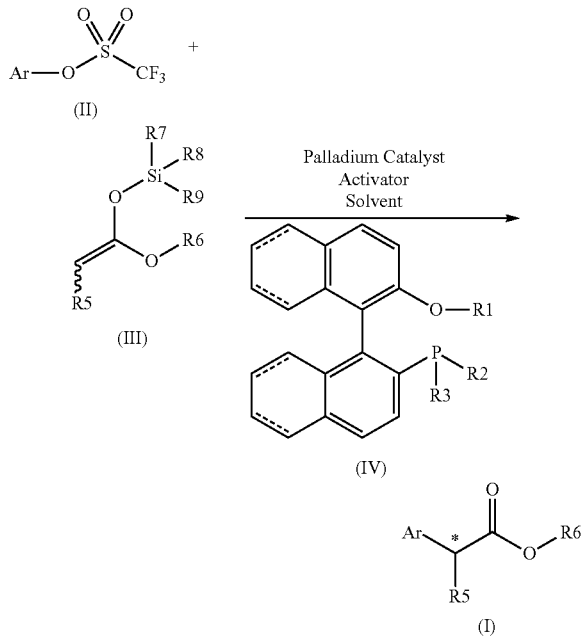

wherein:
* is an asymmetric carbon atom;
the compound of Formula III is the (E)- or (Z)—OSiR$^7$R$^8$R$^9$ isomer;
the palladium catalyst is selected from PdMe$_2$(TMEDA), Pd(dba)$_7$, and Pd(OAc)$_2$;
the solvent is an aromatic solvent;
Ar is a substituted or unsubstituted aryl or substituted or unsubstituted heteroaryl group, which is optionally independently substituted with 1, 2 or 3 R$^4$ groups;
⋰ is a single or double bond, wherein either all of the ⋰ are single bonds or all of the ⋰ are double bonds;
R$^1$ is independently selected from hydrogen, alkyl, aryl, and arylalkyl;
R$^2$ and R$^3$ are each independently selected from alkyl, cycloalkyl, aryl and arylalkyl;
each R$^4$ is independently selected from hydrogen, amino, halogen, hydroxyl, nitro, cyano, alkyl, alkenyl, alkynyl, perfluoroalkyl, cycloalkyl, alkoxy, heterocycloalkyl, aryl, arylalkyl, heteroaryl, heteroarylalkyl, (CH$_2$)$_j$OR$^{11}$, (CH$_2$)$_j$C(O)R$^{11}$, (CH$_2$)$_j$C(O)OR$^{11}$, (CH$_2$)$_j$OC(O)R$^{11}$, (CH$_2$)$_j$NR$^{12}$R$^{13}$, (CH$_2$)$_j$C(O)NR$^{12}$R$^{13}$, (CH$_2$)$_j$OC(O)NR$^{12}$R$^{13}$, (CH$_2$)$_j$NR$^{14}$C(O)R$^{11}$, (CH$_2$)$_j$NR$^{14}$C(O)OR$^{11}$, (CH$_2$)$_j$NR$^{14}$C(O)NR$^{12}$R$^{13}$, (CH$_2$)$_j$S(O)$_m$R$^{11}$, and (CH$_2$)$_j$S(O)$_m$NR$^{12}$R$^{13}$, wherein each j is independently an integer selected from 0 to 6, and each m is independently an integer selected from 0 to 2;
R$^5$ is independently selected from substituted or unsubstituted alkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, which is optionally independently substituted with 1, 2 or 3 R$^{10}$ groups;

R$^6$ is independently selected from hydrogen, substituted or unsubstituted alkyl, substituted or unsubstituted cycloalkyl, substituted or unsubstituted aryl, and substituted or unsubstituted arylalkyl, which is optionally independently substituted with 1, 2 or 3 R$^{10}$ groups;
R$^7$, R$^8$ and R$^9$ are each independently selected from alkyl, aryl and arylalkyl;
each R$^{10}$ is independently selected from hydrogen, amino, halogen, hydroxyl, nitro, cyano, alkyl, alkenyl, alkynyl, perfluoroalkyl, cycloalkyl, alkoxy, heterocycloalkyl, aryl, arylalkyl, heteroaryl, heteroarylalkyl, (CH$_2$)$_j$OR$^{11}$, (CH$_2$)$_j$C(O)R$^{11}$, (CH$_2$)$_j$C(O)OR$^{11}$, (CH$_2$)$_j$OC(O)R$^{11}$, (CH$_2$)$_j$NR$^{12}$R$^{13}$, (CH$_2$)$_j$C(O)NR$^{12}$R$^{13}$, (CH$_2$)$_j$OC(O)NR$^{12}$R$^{13}$, (CH$_2$)$_j$NR$^{14}$C(O)R$^{11}$, (CH$_2$)$_j$NR$^{14}$C(O)OR$^{11}$, (CH$_2$)$_j$NR$^{14}$C(O)NR$^{12}$R$^{13}$, (CH$_2$)$_j$S(O)$_m$R$^{11}$, and (CH$_2$)$_j$S(O)$_m$NR$^{12}$R$^{13}$, wherein each j is independently an integer selected from 0 to 6, and each m is independently an integer selected from 0 to 2;
R$^{11}$ is independently selected from hydrogen, alkyl, alkenyl, alkynyl, perfluoroalkyl, cycloalkyl, heterocycloalkyl, aryl, arylalkyl, heteroaryl, and heteroarylalkyl; and
R$^{12}$, R$^{13}$, R$^{14}$ are each independently selected from hydrogen, alkyl, alkenyl, alkynyl, perfluoroalkyl, cycloalkyl, heterocycloalkyl, aryl, arylalkyl, heteroaryl, and heteroarylalkyl, or R$^{14}$ is as described above, and R$^{12}$ and R$^{13}$ are joined together with the nitrogen atom to which they are attached, to form a substituted or unsubstituted 3- to 7-membered hetercycloalkyl or substituted or unsubstituted 5-membered heteroaryl, wherein the 3- to 7-membered hetercycloalkyl is selected from aziridine, azetidine, pyrrolidinyl, pyrazolidinyl, imidazolidinyl, piperidinyl, piperazinyl, morpholinyl, thiomorpholinyl, and azepanyl; and the 5-membered heteroaryl is selected from pyrrolyl, pyrazolyl, imidazolyl, pyridinyl, pyrazinyl, pyrimidinyl, indolyl, purinyl, benzimidazolyl, quinolinyl, and isoquinolinyl.

2. The method of claim 1, wherein:
* is an R or S asymmetric carbon atom, wherein the asymmetric α-aryl compound of Formula I is at least about 50% to about 60% enantiomeric excess;
the compound of Formula III is the (E)-OSiR$^7$R$^8$R$^9$ isomer;
the palladium catalyst is PdMe$_2$(TMEDA);
the activator is LiOC(O)CH$_3$;
the aromatic solvent is selected from benzene, chlorobenzene, fluorobenzene, toluene, trifluorobenzene, dichloromethane, dichloroethane, tetrahydrofuran and mixtures thereof;
Ar is a substituted or unsubstituted phenyl, substituted or unsubstituted biphenyl, substituted or unsubstituted naphthalenyl, substituted or unsubstituted benzyl, substituted or unsubstituted CH$_2$(1-naphthalenyl), substituted or unsubstituted CH$_2$(2-naphthalenyl), substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted pyridinyl, substituted or unsubstituted pyrazinyl, substituted or unsubstituted pyrimidinyl, substituted or unsubstituted indolyl, substituted or unsubstituted purinyl, substituted or unsubstituted benzimidazolyl, substituted or unsubstituted benzo[b]thiophenyl, substituted or unsubstituted quinolinyl, and substituted or unsubstituted isoquinolinyl;

R¹ is independently selected from hydrogen, (C₁-C₆) alkyl, phenyl, biphenyl, naphthalenyl, benzyl, CH₂(1-naphthalenyl) and CH₂(2-naphthalenyl);

R² and R³ are each independently selected from (C₁-C₆) alkyl, (C₃-C₆)cycloalkyl, phenyl, biphenyl, benzyl, and naphthalenyl;

R⁵ is independently selected from substituted or unsubstituted (C₁₋₁₂)alkyl, substituted or unsubstituted phenyl, substituted or unsubstituted biphenyl, substituted or unsubstituted naphthalenyl, substituted or unsubstituted benzyl, substituted or unsubstituted CH₂(1-naphthalenyl), substituted or unsubstituted CH₂(2-naphthalenyl), substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted pyridinyl, substituted or unsubstituted pyrazinyl, substituted or unsubstituted pyrimidinyl, substituted or unsubstituted indolyl, substituted or unsubstituted purinyl, substituted or unsubstituted benzimidazolyl, substituted or unsubstituted benzo[b]thiophenyl, substituted or unsubstituted quinolinyl, substituted or unsubstituted isoquinolinyl, substituted or unsubstituted aziridine, substituted or unsubstituted oxiranyl, substituted or unsubstituted thiiranyl, substituted or unsubstituted azetidinyl, substituted or unsubstituted oxetanyl, substituted or unsubstituted thietanyl, substituted or unsubstituted pyrrolidinyl, substituted or unsubstituted pyrazolidinyl, substituted or unsubstituted imidazolidinyl, substituted or unsubstituted oxolanyl, substituted or unsubstituted thiolanyl, substituted or unsubstituted piperidinyl, substituted or unsubstituted oxanyl, substituted or unsubstituted thianyl, substituted or unsubstituted piperazinyl, substituted or unsubstituted morpholinyl, substituted or unsubstituted thiomorpholinyl, substituted or unsubstituted azepanyl, substituted or unsubstituted oxepanyl, and substituted or unsubstituted thiepinyl;

R⁶ is independently selected from hydrogen, substituted or unsubstituted (C₁-C₆)alkyl, substituted or unsubstituted (C₃-C₈)cycloalkyl, phenyl, substituted or unsubstituted biphenyl, substituted or unsubstituted naphthalenyl, substituted or unsubstituted benzyl, substituted or unsubstituted CH₂(1-naphthalenyl), substituted or unsubstituted CH₂(2-naphthalenyl); and R⁷, R⁸ and R⁹ are each independently selected from (C₁-C₆)alkyl and phenyl.

3. The method of claim 2, wherein:

* is an R or S asymmetric carbon atom, wherein the asymmetric α-aryl compound of Formula I is at least about 60% to about 70% enantiomeric excess;

Ar is selected from substituted or unsubstituted phenyl, substituted or unsubstituted naphthalenyl, substituted or unsubstituted benzyl, substituted or unsubstituted CH₂(1-naphthalenyl), substituted or unsubstituted CH₂(2-naphthalenyl), substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted pyridinyl, substituted or unsubstituted pyrazinyl, substituted or unsubstituted pyrimidinyl, substituted or unsubstituted indolyl, substituted or unsubstituted benzimidazolyl, substituted or unsubstituted benzo[b]thiophenyl, substituted or unsubstituted quinolinyl, and substituted or unsubstituted isoquinolinyl;

R¹ is independently selected from hydrogen, methyl, ethyl, n-propyl, isopropyl, n-butyl, sec-butyl, tert-butyl, phenyl, benzyl, CH₂(1-naphthalenyl), and CH₂(2-naphthalenyl);

R² and R³ are each independently selected from (C₁-C₆) alkyl and (C₃-C₆)cycloalkyl;

R⁵ is independently selected from substituted or unsubstituted (C₁-C₁₂)alkyl, substituted or unsubstituted phenyl, substituted or unsubstituted naphthalenyl, substituted or unsubstituted benzyl, substituted or unsubstituted CH₂(1-naphthalenyl), and substituted or unsubstituted CH₂(2-naphthalenyl);

R⁶ is independently selected from hydrogen, (C₁-C₆) alkyl, (C₃-C₈)cycloalkyl, phenyl, naphthalenyl, benzyl, CH₂(1-naphthalenyl), and CH₂(2-naphthalenyl); and R⁷, R⁸ and R⁹ are each independently selected from (C₁-C₆)alkyl.

4. The method of claim 3, wherein:

* is an R or S asymmetric carbon atom, wherein the asymmetric α-aryl compound of Formula I is at least about 70% to about 80% enantiomeric excess; and the compound of Formula IV has Formula IVa or IVb:

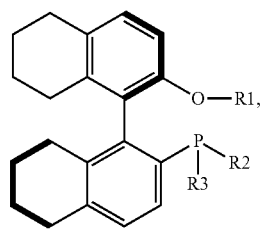

(IVa)

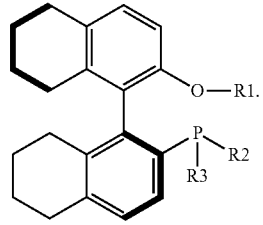

(IVb)

5. The method of claim 3, wherein:

* is an R or S asymmetric carbon atom, wherein the asymmetric α-aryl compound of Formula I is at least about 80% to about 90% enantiomeric excess; and the compound of Formula IV has Formula IVc or IVd:

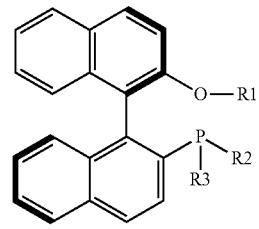

(IVc)

-continued (IVd)

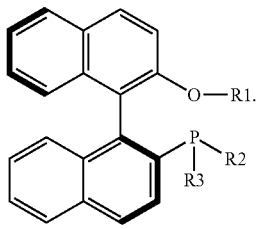

6. The method of claim 1, further comprising heating the compound of Formula II with the compound of Formula III in the presence of the palladium catalyst, the activator, the compound of Formula IV, and the solvent to produce the asymmetric α-aryl compound of Formula I.

7. The method of claim 1, wherein the compound of Formula I, or pharmaceutically acceptable salt thereof, is (S)-Naproxen or the tert-butyl ester thereof:

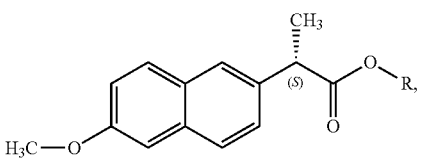

wherein R is H or C(CH$_3$)$_3$.

8. The method of claim 1, wherein the aromatic solvent is selected from the group consisting of benzene, chlorobenzene, fluorobenzene, toluene, trifluorobenzene, dichloromethane, dichloroethane, tetrahydrofuran, and combinations thereof.

9. The method of claim 1, wherein the activator is selected from LiOC(O)CH3, LiOC(O)CF3, LiOS(O)2CH3, LiOC(O)C(CH3)3, LiF, NaOC(O)CH3, NaOC(O)CF3, Na2CO3, KOC(O)CH3, CsF, Cs2CO3, CsOC(O)CH3, ZnF2, Zn(OC(O)CH3)2, CuF2, and combinations thereof.

* * * * *